United States Patent
Howard et al.

(10) Patent No.: US 8,829,184 B2
(45) Date of Patent: Sep. 9, 2014

(54) INTERMEDIATES USEFUL FOR THE SYNTHESIS OF PYRROLOBENZODIAZEPINES

(75) Inventors: Philip Wilson Howard, London (GB); Luke Masterson, London (GB); Arnaud Tiberghien, London (GB)

(73) Assignee: Spirogen SARL, St-Legier-la Chiesaz (CH)

( * ) Notice: Subject to any disclaimer, the term of this patent is extended or adjusted under 35 U.S.C. 154(b) by 32 days.

(21) Appl. No.: 13/641,237

(22) PCT Filed: Apr. 15, 2011

(86) PCT No.: PCT/GB2011/000588
§ 371 (c)(1),
(2), (4) Date: Oct. 15, 2012

(87) PCT Pub. No.: WO2011/128650
PCT Pub. Date: Oct. 20, 2011

(65) Prior Publication Data
US 2013/0035484 A1    Feb. 7, 2013

(30) Foreign Application Priority Data
Apr. 15, 2010    (GB) .................................. 1006340.2

(51) Int. Cl.
| C07D 207/20 | (2006.01) |
| C07D 207/22 | (2006.01) |
| C07D 207/24 | (2006.01) |
| C07D 487/04 | (2006.01) |

(52) U.S. Cl.
USPC ......................................... 540/496; 548/539

(58) Field of Classification Search
USPC ......................................... 540/496; 548/539
See application file for complete search history.

(56) References Cited

U.S. PATENT DOCUMENTS

| 3,523,941 | A  | 8/1970  | Leimgruber et al. |
| 3,524,849 | A  | 8/1970  | Batcho et al. |
| 3,619,374 | A  | 11/1971 | Berger et al. |
| 4,185,016 | A  | 1/1980  | Takanabe et al. |
| 4,239,683 | A  | 12/1980 | Takanabe et al. |
| 4,309,437 | A  | 1/1982  | Ueda et al. |
| 5,418,241 | A  | 5/1995  | Jegham et al. |
| 6,562,806 | B1 | 5/2003  | Thurston et al. |
| 6,608,192 | B1 | 8/2003  | Thurston et al. |
| 6,660,856 | B2 | 12/2003 | Wang |
| 6,747,144 | B1 | 6/2004  | Thurston et al. |
| 6,909,006 | B1 | 6/2005  | Thurston et al. |
| 7,049,311 | B1 | 5/2006  | Thurston et al. |
| 7,067,511 | B2 | 6/2006  | Thurston et al. |
| 7,265,105 | B2 | 9/2007  | Thurston et al. |
| 7,407,951 | B2 | 8/2008  | Thurston et al. |
| 7,429,658 | B2 | 9/2008  | Howard et al. |
| 7,528,126 | B2 | 5/2009  | Howard et al. |
| 7,557,099 | B2 | 7/2009  | Howard et al. |
| 7,612,062 | B2 | 11/2009 | Howard et al. |
| 7,704,924 | B2 | 4/2010  | Thurston et al. |
| 2003/0195196 | A1 | 10/2003 | Thurston et al. |
| 2004/0138269 | A1 | 7/2004  | Sun et al. |
| 2004/0198722 | A1 | 10/2004 | Thurston et al. |
| 2007/0191349 | A1 | 8/2007  | Howard et al. |
| 2007/0249591 | A1 | 10/2007 | Howard et al. |
| 2008/0090812 | A1 | 4/2008  | Pepper et al. |
| 2008/0214525 | A1 | 9/2008  | Howard et al. |

FOREIGN PATENT DOCUMENTS

| EP | 1193270   | 4/2002  |
| FR | 2027356   | 12/1969 |
| FR | 2586683   | 3/1987  |
| GB | 1299198   | 12/1972 |
| JP | 53-82792  | 7/1978  |
| JP | 57131791  | 8/1982  |
| JP | 58180487  | 10/1983 |

(Continued)

OTHER PUBLICATIONS

Adams et al., "Molecular modelling of a sequence-specific DNA-binding agent based on the pyrrolo[2,1-c][1,4]benzodiazepines," Pharm. Pharmacol. Commun. (1999) 5:555-560.

(Continued)

*Primary Examiner* — Bruck Kifle
(74) *Attorney, Agent, or Firm* — Michael Best & Friedrich LLP

(57) ABSTRACT

A compound of formula (I): which is substantially free of any of the corresponding compound of formula (IB): methods of making such compounds, and the further transformation of such compounds.

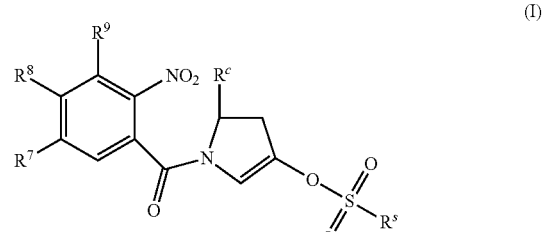

(I)

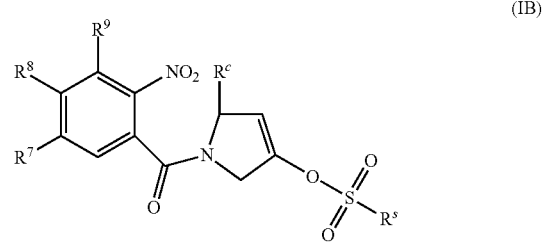

(IB)

24 Claims, No Drawings

(56) References Cited

FOREIGN PATENT DOCUMENTS

| | | |
|---|---|---|
| WO | 92/19620 | 11/1992 |
| WO | 93/18045 | 9/1993 |
| WO | 00/12506 | 3/2000 |
| WO | 00/12507 | 3/2000 |
| WO | 00/12508 | 3/2000 |
| WO | 00/12509 | 3/2000 |
| WO | WO 2004/043963 | 5/2004 |
| WO | WO 2005/023814 | 3/2005 |
| WO | WO 2005/040170 | 5/2005 |
| WO | WO 2005/042535 | 5/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/110423 | 11/2005 |
| WO | WO 2010/010347 | 1/2010 |

OTHER PUBLICATIONS

Althius, T. H. and Hess, H. J., "Synthesis and Identification of the Major Metabolites of Prazosin Formed in Dog and Rat," J. Medicinal Chem. (1977) 20(1):146-148.

Arima et al., "Studies on Tomaymycin, a New Antibiotic. I. Isolation and Properties of Tomaymycin," J. Antibiotics (1972) 25:437-444.

Berge et al., "Pharmaceutical Salts," J. Pharm. Sci. (1977) 66:1-19.

Berry, J. M. et al., "Solid-phase synthesis of DNA-interactive pyrrolo[2,1-c][1,4]benzodiazepines," Tetrahedron Letters (2000) 41:6171-6174.

Bose et al., "New Approaches to Pyrrolo[2,1-c][1,4]benzodiazepines: Synthesis, DNA-binding and cytotoxicity of DC-81," Tetrahedron, 48, 751-758 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).

Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.

Cooper, N. et al., "Synthesis of novel PBDs as anti-tumour agents," Chem. Commun. (2002) 16:1764-1765.

Courtney, S. M. et al., "A new convenient procedure for the synthesis of pyrrolo[2,1-c][1,4]benzodiazepines", Tetrahedron Letters, vol. 34, No. 33, 5327-28 (1993).

Cramer, N. et al., "Enantioselective total synthesis of cylindramide," Angew. Chem. Int. Ed. (2005) 44:820-822.

Farmer, J.D. et al., "DNA binding properties of a new class of linked anthramycin analogs,", Chemical Abstracts, Abstract No. 239940r, vol. 114, No. 25, 25 899-903 (1991).

Foloppe, M.P. et al., "DNA-binding properties of pyrrolo[2,1-c][1,4]benzodiazephine N10-C11 amidines," Eur. J. Med. Chem., 31, 407-410 (1996).

Fujisawa Pharmaceutical Co., Ltd., "Benzodiazepine derivatives," SciFinder Scholar (2002) 2-3.

Fujisawa Pharmaceutical Co., Ltd., Abstract No. 139983k, "Benzodiazepine derivatives", Chemical Abstracts, vol. 99, No. 17, 603 (1983).

Fujisawa Pharmaceutical Co., Ltd., Abstract No. 72145x, "Benzodiazepine derivatives", Chemical Abstracts, vol. 98, No. 9, 638 (1983).

Fukuyama, T. et al., "Total Synthesis of (+)-Porothramycin B," Tetrahedron Letters, vol. 34, 16, 2577-2580 (1993).

Greene, T.W. et al., Protective Groups in Organic Synthesis, 3rd Edition (1999) John Wiley & Sons, Inc., pp. 23-200.

Greene, T.W. et al., Protective Groups in Organic Synthesis, John Wiley & Sons, 2nd Edition, Chapter 7 (1991) 315-345.

Greene, T.W. et al., Protective Groups in Organic Synthesis, John Wiley & Sons, Inc., 3rd Edition (1999) 503-549.

Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1- c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).

Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).

Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).

Hara et al., "DC 102, a new glycosidic pyrrolo(1,4)benzodiazepine antibiotic produced by streptomyces sp.", J. Antibiotics, 41, 702-704 (1988).

Hochlowski, J. et al., "Abbeymycin, a new anthramycin-type antibiotic produced by a streptomycete," J. Antibiotics, 40, 145-148 (1987).

Howard, P.W. et al., "Synthesis of a novel C2/C2'-aryl-substituted pyrrolo[2,1-c][1,4]benzodiazepine dimer prodrug with improved water solubility and reduced DNA reaction rate," Biorg. Med. Chem. Left (2009) 19:6463-6466.

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).

Itoh et al., "Sibanomicin, a new pyrrolo(1,4)benzodiazepine antitumor antibiotic produced by a micromonospora sp." J. Antibiotics, 41, 1281-1284 (1988).

Kamal et al., "Synthesis and DNA-binding affinity of A-C8/C-C2 alkoxyamido-linked pyrrolo[2,1-c][1,4]benzodiazepine dimers" Biorg. Med. Chem. Left. (2003) 13(22):3955-3958.

Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Left. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Knapp, D.M. et al., "A general solution for unstable boronic acids: slow-release cross-coupling from air-stable MIDA boronates," J. Am. Chem. Soc. (2009) 131:6961-6963.

Kohn, K., "Anthramycin," Antibiotics III, Springer-Verlag, NY, 3-11 (1975).

(56) References Cited

OTHER PUBLICATIONS

Konishi, M. et al., "Chicamycin, a new antitumor antibiotic II. Structure determination of chicamycins A and B," J. Antibiotics, 37, 200-206 (1984).
Kunimoto et al., "Mazethramycin, a new member of anthramycin group antibiotics," J. Antibiotics, 33, 665-667 (1980).
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Molander, G.A. et al., "Cross-coupling reactions of potassium alkyltrifluoroborates with aryl and 1-alkenyl trifluoromethanesulfonates," Org. Lett. (2001) 3(3):393-396.
Mori, M. et al., "Total syntheses of prothracarcin and tomaymycin by use of palladium catalyzed carbonylation," Tetrahedron (1986) 42(14):3793-3806.
Mountzouris, J.A. et al., "Comparison of a DSB-120 DNA interstrand cross-linked adduct with the corresponding bis-Tomamycin adduct," J. Med. Chem. (1994) 37:3132-3140.
Mu, Yq., et al., "Coupling of isoprenoid triflates with organoboron nucleophiles: synthesis of all-trans-geranylgeraniol," Tetrahedron Left. (1995) 36(32):5669-5672.
Nagasaka, T. and Koseki, Y, "Stereoselective Synthesis of Tilivalline," Journal of Organic Chemistry, vol. 63, No. 20, 6797-6801 (1998).
Nagasaka, T. et al., "Stereoselective Synthesis of Tilivalline," Tetrahedron Letters, 30:14, 1871-1872 (1989).
Nishihara, Y. et al., "Coupling reactions of alkynylsilanes mediated by a Cu(I) salt: novel syntheses of conjugate diynes and disubstituted ethynes," J. Org. Chem. (2000) 65:1780-1787.
Oh-E, T. et al., "Palladium-catalyzed cross-coupling reaction of aryl or vinylic triflates with organoboron compounds," SynLett (1990) 221-223.
Oh-E, T. et al., "Palladium-catalyzed cross-coupling reaction of organoboron compounds with organic triflates," J. Org. Chem. (1993) 58:2201-2208.
O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).
Perez, I. et al., "Palladium-catalyzed cross-coupling reactions of triorganoindium compounds with vinyl and aryl triflates or iodides," Org. Lett. (1999) 1(8):1267-1269.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Shimizu, K et al., "Prothracarcin, a Novel Antitumor Antibiotic," J. Antibiotics, 35, 972-978 (1982).
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Suggs, J.W. et al., "Synthesis and structure of anthramycin analogs via hydride reduction of dilactams," Tetrahedron Letters, 26, No. 40, 4871-4874 (1985).
Takeuchi, T. et al., "Neothramycins A and B, New Antitumor Antibiotics," J. Antibiotics, 29, 93-96 (1976).
Tercel, M. et al., "Unsymmetrical DNA cross-linking agents: combination of the CBI and PBD pharmacophores," J. Med. Chem. (2003) 46:2132-2151.
Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tsunakawa, M. et al., "Porothramycin, a new antibiotic of the anthramycin group: Production, isolation, structure and biological activity," J. Antibiotics, 41:1366-1373 (1988).
Umezawa, H. et al., Chemical Abstract No. 4427a, "Mazethramycins" Chemical Abstracts, vol. 90, No. 1, 428 (1979).
Umezawa, H. et al., "Mazethramycins," SciFinder Scholar (2002) 2-3.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42:4028-4041 (1999).
Yao, M-L. et al., "Facile approach to 4-substituted 2(5H)-furanones," J. Org. Chem. (2000) 65:5034-5036.

INTERMEDIATES USEFUL FOR THE SYNTHESIS OF PYRROLOBENZODIAZEPINES

CROSS-REFERENCE TO RELATED APPLICATIONS

This patent application is a national stage filing under 35 U.S.C. 371 of International Application No. PCT/GB2011/000588, filed on Apr. 15, 2011, which claims foreign priority benefits to United Kingdom Patent Application No. 1006340.2, filed on Apr. 15, 2010. These applications are incorporated herein by reference in their entireties.

The present invention relates to methods useful in the synthesis of pyrrolobenzodiazepines (PBDs), and in particular of pyrrolobenzodiazepines having C2 substitution and N10 protection.

BACKGROUND TO THE INVENTION

PBDs are of the general structure:

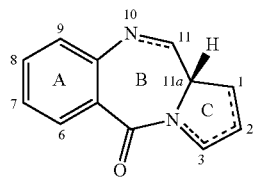

C2-substituted Compounds

In WO 2004/043963, a diverse range cytotoxic compounds having an aryl group at the C2 position, for example:

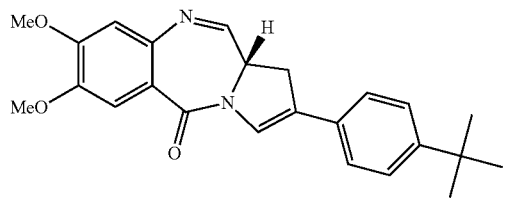 [SMILES: COc1cc2c(cc1OC)C(=O)N1C=C(c3ccc(C(C)(C)C)cc3)C[C@H]1C=N2]

were disclosed. The synthesis of these compounds was achieved via the following intermediate:

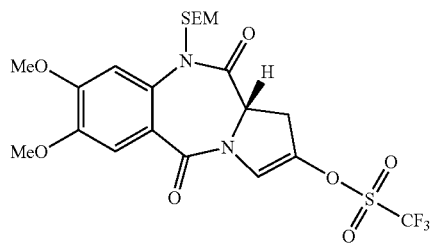 [SMILES: COc1cc2c(cc1OC)N(COCC[Si](C)(C)C)C(=O)[C@@H]1CC(OS(=O)(=O)C(F)(F)F)=CN1C2=O]

whose synthesis was described in detail in WO 00/12508. An analagous dimeric intermediate is disclosed in WO 2010/010347.

WO 2005/085251 discloses the synthesis of a number cytoxic compounds having an aromatic substituent at C2 from the intermediate:

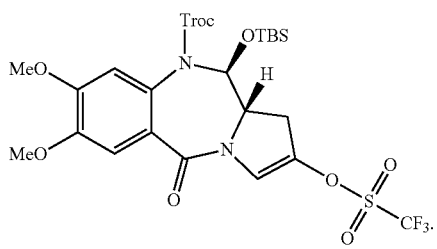

These intermediates are very useful for synthesis C2 substituted PBD compounds having a N10-C11 imine bond, or compounds readily derivable from these, e.g. bisulphite versions, as in WO 2010/010347. The N10 protecting groups used are not labile under the conditions used to add the C2 aryl substituents, for example, in a Suzuki coupling using a palladium catalyst.

The C2-aryl group is installed by forming a C2-enol triflate followed by a palladium catalyzed Suzuki reaction. It is advantageous to add the C2 aryl substituents as late as possible in the synthesis by the methods described above, as this means a diverse range of substituents can be added to a single 'core'.

However, there are compounds of interest where the protecting groups or linkers desired at N10 are labile under either the triflation conditions (e.g. substituted p-aminobenzyl or p-hydroxybenzyl carbamates) or palladium catalysis (e.g. Alloc), see below.

Such groups are preferably introduced at a point in the synthesis of the PBD before the B-ring is formed by cyclisation. Otherwise, these groups would need to be added via a chloroformate to the PBD's imine bond. In addition, the cyclisation of PBD is best carried out where the pro-N10 nitrogen has only a single hydrogen attached, i.e., where the protecting group is already in place.

DISCLOSURE OF THE INVENTION

The present inventors have developed a key intermediate for the production of C2 substituted PBDs having a palladium sensitive N10 protecting group, and a method for its synthesis.

In a first aspect, the present invention comprises a compound of formula I:

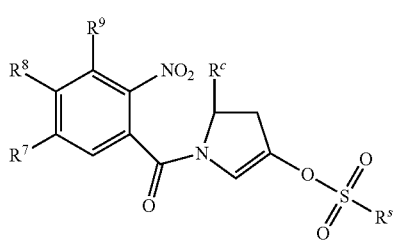

wherein:
$R^7$ and $R^8$ are independently selected from: $OR^A$, where $R^A$ is selected from $C_{1-4}$ saturated alkyl, optionally substituted by phenyl, which phenyl may bear a chloro substituent, pyridyl and furanyl; chloro; $NH_2$; and $-CH_2-O-C(=O)Me$;
or $R^7$ and $R^8$ together form a group $-O-(CH_2)_m-O-$, where m is 1 or 2;

or the compound is a dimer with each monomer independently being of formula (I), where the $R^7$ groups or $R^8$ groups of each monomer form together a dimer bridge having the formula —X—R"—X— linking the monomers, where R" is a $C_{3-12}$ saturated alkylene group, which group may be interrupted by O, S, NH, NMe, phenylene or pyridylene, where the phenylene and pyridylene groups are optionally substituted by $NH_2$, and each X is independently selected from O, S, or NH;

$R^9$ is selected from H, methyl and methoxy;

$R^S$ is selected from $CF_3$, $(CF_2)_3CF_3$, $CH_3$ and

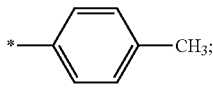 [SMILES: *c1ccc(C)cc1]

and $R^C$ is selected:
(i) —C(=O)—$OR^{C1}$, where $R^{C1}$ is a saturated $C_{1-4}$ alkyl group;
(ii) —$CH_2$—O—C(=O)$R^{C2}$, where $R^{C2}$ is methyl or phenyl;
(iii) —$CH_2$—O—Si—($R^{Si1}$)($R^{Si2}$)($R^{Si3}$) where $R^{Si1}$, $R^{Si2}$, $R^{Si3}$ are independently selected from a $C_{1-6}$ saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene.

The compound of formula I is substantially free of any of the corresponding compound of formula IB:

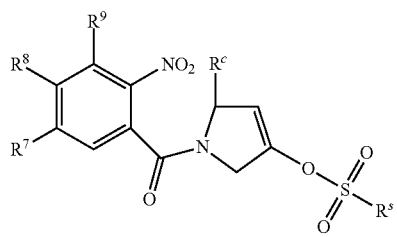

IB wherein $R^7$, $R^8$, $R^9$ and $R^C$ are as defined in the compound of formula I. "Substantially free" means that there is less than 5% by weight of the compound of formula IB compared to the amount of the compounds of formula I. More preferably, there is less than 1% or 0.1% by weight of the compound of formula IB.

In a second aspect, the present invention provides a method of synthesising a compound of formula I as defined in the first aspect of the invention from a compound of formula II:

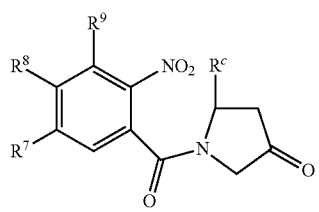

II wherein $R^7$, $R^8$, $R^9$ and $R^C$ are as defined in the first aspect;

comprising treating II with the appropriate anhydride and anhydrous 2,6-lutidine or anhydrous 2,6-'Bu-pyridine at a temperature of –35° C. or lower in a dry organic solvent under an inert atmosphere.

The following reaction has been previously disclosed (Kang, G-D., et al., Chem. Commun., 2003, 1680-1689):

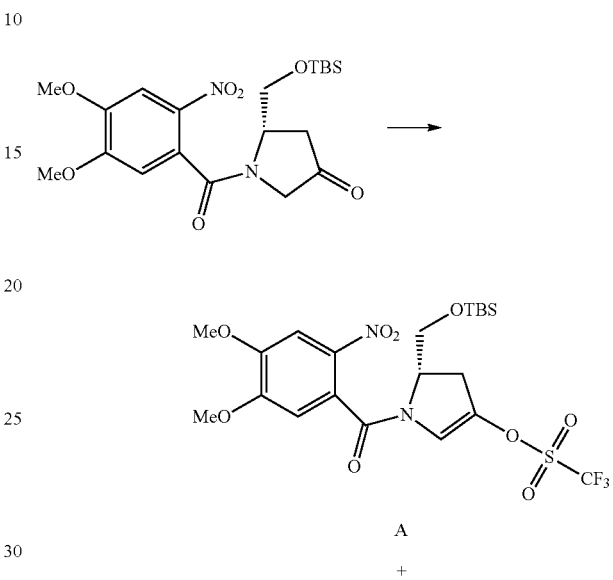

A

+

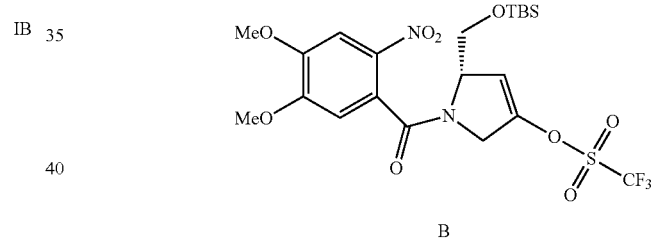

B

This reaction was carried out using (trifluoromethanesulfonyl)aminopyridine at –78° C., which followed treatment with either LDA (lithium diethylamide) or NaHMDS (sodium hexamethyldisilazide). The method involving LDA gave a mixture of A to B in the ratio 1:4, whilst the NHDMS method gave only B.

Compounds of formula I can be converted into N10 protected PBD compounds by the following steps.

A.

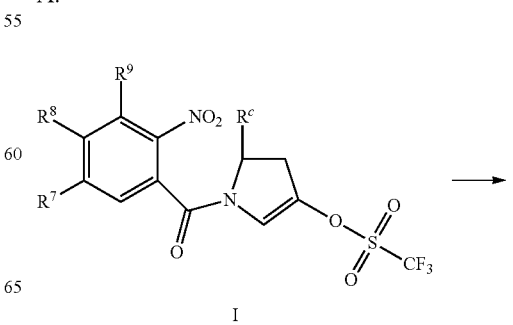

I

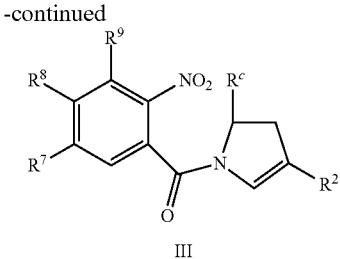

where R² is selected from:
(i) an optionally substituted $C_{5-20}$ aryl group;
(ii) an optionally substituted $C_{1-5}$ alkyl group (including a $C_{2-5}$ alkenyl group and a $C_{2-5}$ alkynyl group); and
(iii) H.

These conversions are carried using palladium catalysis, and include: Suzuki couplings with an appropriate boron derivative; Heck coupling with alkenes, including acrylamides and acrylates; Stille couplings with organo tin reagents, such as alkyl tin reagents; Sonagishira couplings with alkynes; and hydride transfer using triethyl silanes.

The conversion where R² is an optionally substituted $C_{5-20}$ aryl group (a Suzuki coupling) is carried out by palladium catalysed cross coupling of I with the appropriate aryl boron derivative. The palladium catalyst may be any suitable catalyst, for example $Pd(PPh_3)_4$, $Pd(OCOCH_3)_2$, $PdCl_2$, or $Pd(dba)_3$.

Suzuki couplings may also be used to cross couple alkyl boron species. The Gibbs group has reported (Mu, Y. Q and Gibbs, R. A, *Tetrahedron Letters*, 36, 5669-5672, 1995) the successful conversion of an enol triflate to a methyl substituted alkene (using a $Pd(PHCN)_2Cl_2$ catalyst):

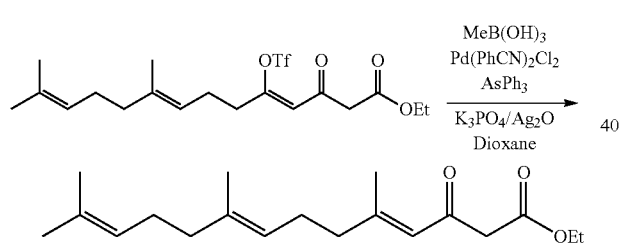

Deng's group successfully achieved the coupling of a cyclopropylboronic acid and a cyclic triflate using a Pd $(MeCN)_2Cl_2$ catalyst (Yao and Deng, *J. Org. Chem.* 2000, 65, 1609).

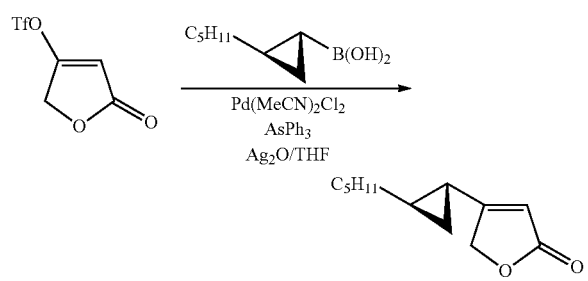

Cyclopropyl MIDA boronates have been successfully coupled to aryl chlorides under slow release conditions; intact MIDA boronates are resistant to standards Suzuki conditions due to their pyramidal hybridization (Knapp et al. *J. Am. Chem. Soc.*, 2009, 131, 6961-6963). These conditions are also be applicable to enoltriflates.

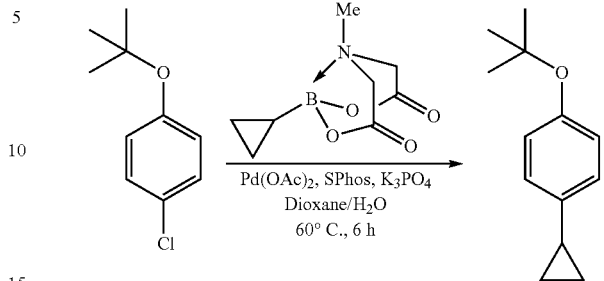

Knapp of al. *J. Am. Chem. Soc.*, 2009, 131, 6961-6963

Molander (Molander and Ito *Org. Lett.*, 2001, 3, 393-396) has developed potassium alkyltrifluoroborates as Suzuki coupling partners for aryl and vinyl triflates.

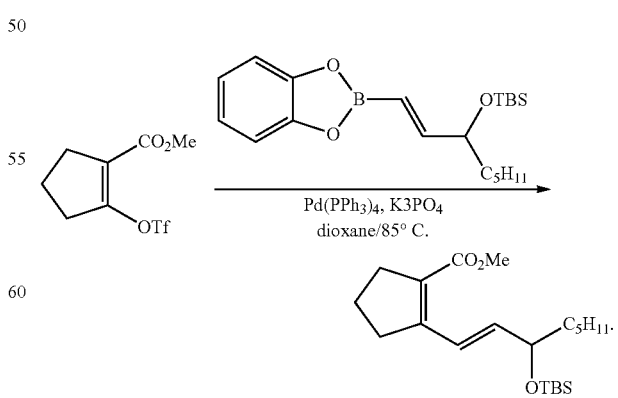

Suzuki couplings may also be used to cross couple alkenyl boron species. Suzuki and co workers have demonstrated (Suzuki et al., Synlett 1990, 221; *J Org Chem* 1993, 58, 2201) the coupling of cyclic triflates and benzodioxoleborole compounds Alkenyl Boronic acids have also been coupled to PBD C-ring enoltriflates (WO2005/085251):

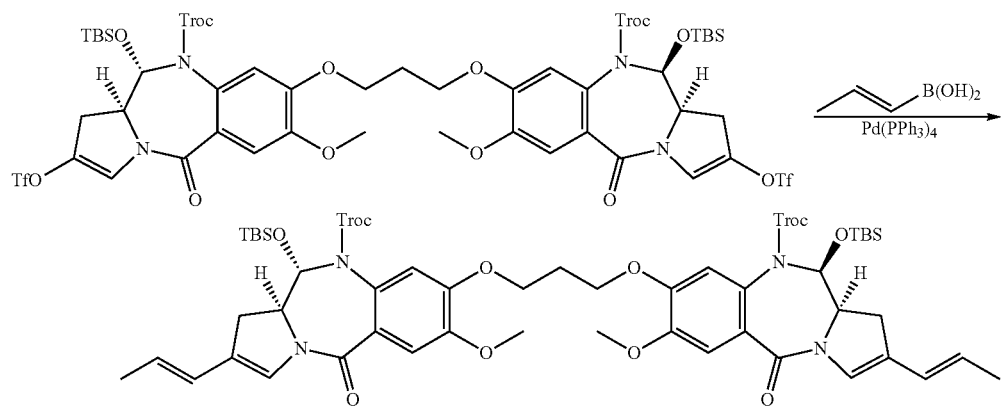

The pinacol esters of acrylylboronic acids are known:

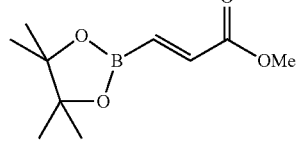

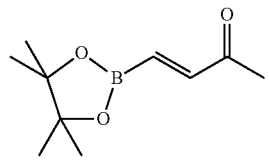

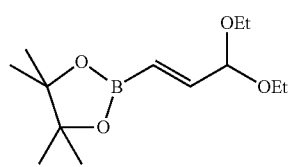

and are likely to ebe useful in Suzuki coupling reactions.

PBD enol triflates have been successfully coupled to acrylamides and acrylates under Heck conditions (Chen et al., *Bioorg. Med. Chem. Lett.* 14, (2004), 1547-1549):

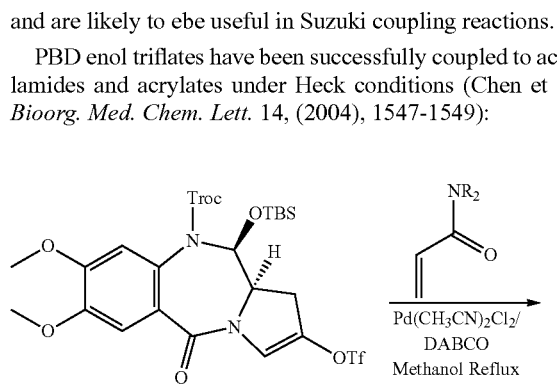

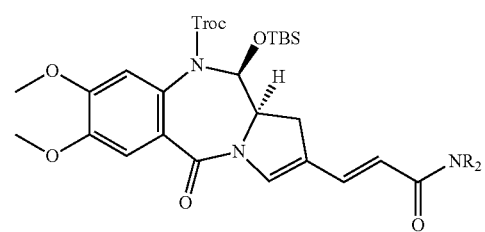

-continued

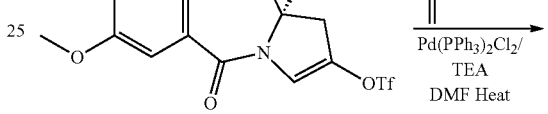

Alkynyl tin reagents have been coupled under Stille conditions to PBD triflates (Tiberghien et al., *Bioorg. Med. Chem. Lett.* 14, (2004), 5041-5044):

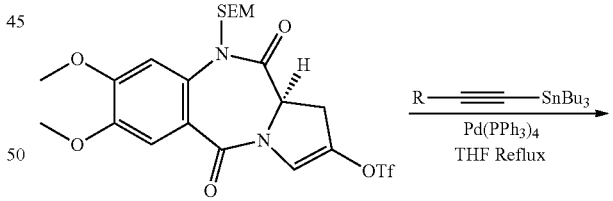

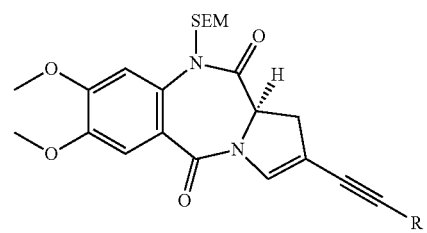

R = H, Ph

Alkynyl substituents can also be installed via the Sonogishira reaction (Nishihara et al *J. Org. Chem.*, 2000, 65, 1780-1787):

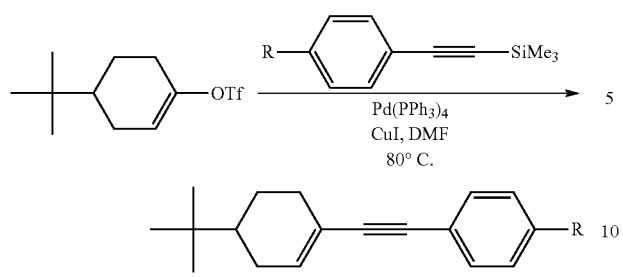

Other palladium catalysed reactions include the use triakylindium reagents in cross-coupling reactions (Perez et al. *Org. Lett,* 1999, 1, 1267-1269):

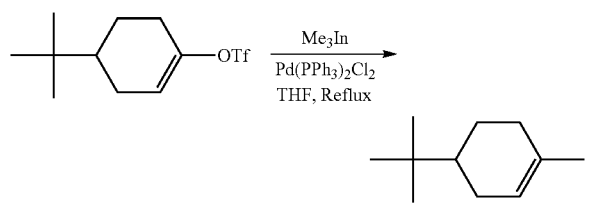

The approach can also be used to introduce aryl, vinyl and alkynyl groups.

Palladium catalysis can also be used in hydride transfer reactions to generate alkenes with triethylsilanes (Cramer et al., *Angew. Chem. Int. Ed.* 2005, 44, 820-822):

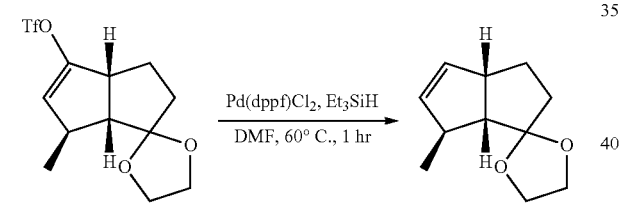

B.

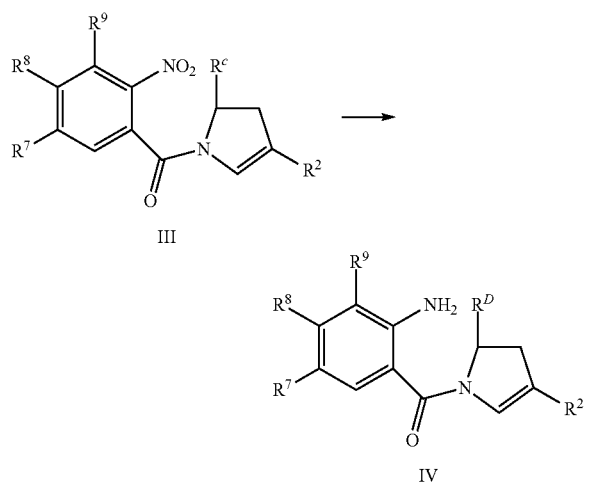

where $R^D$ is selected from:

(ii) —$CH_2$—O—C(=O)$R^{C2}$, where $R^{C2}$ is methyl or phenyl;

(iii) —$CH_2$—O—Si—$(R^{Si1})(R^{Si2})(R^{Si3})$ where $R^{Si1}$, $R^{Si2}$, $R^{Si3}$ are independently selected from a $C_{1-6}$ saturated alkyl group and a phenyl group; and (iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene.

If $R^C$ is —$CH_2$—O—C(=O)$R^{C2}$ or —$CH_2$—O—Si—$(R^{Si1})(R^{Si2})(R^{Si3})$ then the conversion of III to IV is by reduction of the nitro group.

If $R^C$ is —C(=O)—$OR^{C1}$, then the conversion of III to IV is achieved by first reducing of the ester and reprotection as an acetate or silyl ether. The reduction can be achieved by standard means, for example with $LiAlH_4$, $LiBH_4$ or $NaBH_4$, but preferably $LiBH_4$. Reprotection as an aceate can be achieved, for example, by reaction with acetyl chloride; reprotection as a benzoate can be achieved, for example, by reaction with benzoyl chloride; reprotection as a silyl ether can be achieved, for example, by reaction with the appropriate silyl chloride. The reduction of the nitro group is then carried out as described above.

C:

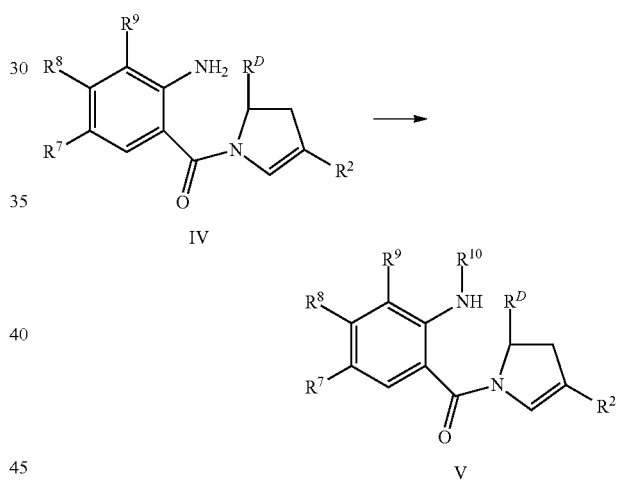

where $R^{10}$ is a carbamate-based nitrogen protecting group, which is palladium-labile and/or labile under the conditions used to add the group:

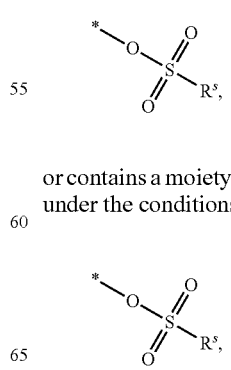

or contains a moiety which is palladium-labile and/or is labile under the conditions used to add the group:

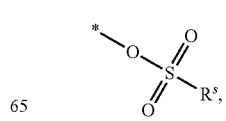

i.e. liable to be removed in the presence of palladium or under the conditions used to add the group:

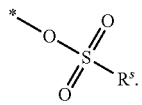

In this application these protecting groups are classified as 'simple' and 'complex'.

Conversion of IV to V is usually achieved by reaction of IV with triphosgene to obtain the isocyanate followed by reaction with $R^{10}$—OH. This approach is described in WO 2005/023814.

Alternatively, simple nitrogen protecting groups can also be introduced as a chloroformate, fluoroformate or azidoformate. The more complex nitrogen protecting groups, as well as the simple nitrogen protecting groups, can be introduced as O-succinamide carbonates, O-pentafluorophenyl carbonates and O-nitrophenyl carbonates.

D:

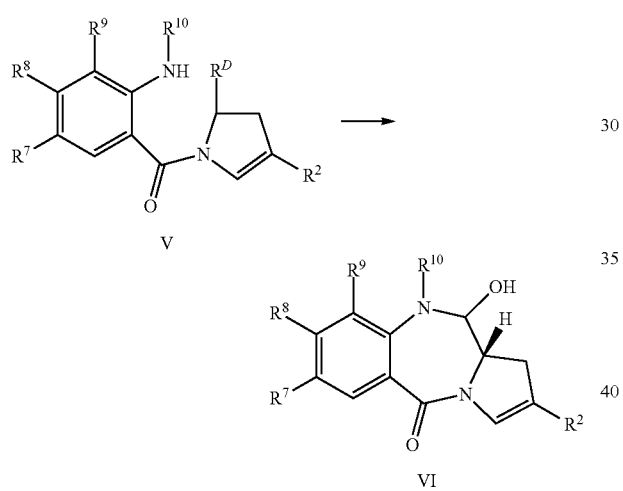

When $R^D$ is —$CH_2$—O—C(═O)Me, the conversion of V to VI may be achieved by initial removal of the acetate protecting group, with potassium carbonate in aqueous methanol, or with lithium triethylborohydride. Oxidation with Dess-Martin periodinane (or alternatively TPAP/NMO, TFAA/DMSO, $SO_3$. Pyridine complex/DMSO, PDC, PCC, BAIB/TEMPO or under Swern conditions) affords the ring closed product.

When $R^D$ is —$CH_2$—O—C(═O)Ph, the conversion of V to VI may be achieved by initial removal of the benzoate protecting group, with sodium hydroxide in aqueous methanol, followed by oxidation as described above.)

When $R^D$ is —$CH_2$—O—Si—($R^{Si1}$)($R^{Si2}$)($R^{Si3}$), the conversion of V to VI may be achieved by initial removal of the silyl ether protecting group, for example using TBAF in THF, acetic acid in aqueous THF, CsF in DMF or HF in pyridine, followed by oxidation as described above.

When $R^D$ is —C(—$YR^{C3}$)(—$YR^{C4}$), the conversion of V to VI may be achieved by removal of the acetal or thioacetal protecting groups, respectively with acid or reaction with Hg (II) salts—the cyclisation occurs spontaneously The present invention also provides:

(a) a compound of formula III:

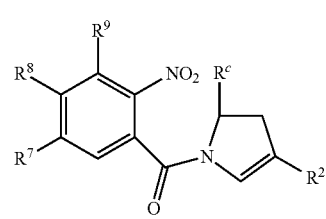

substantially free of

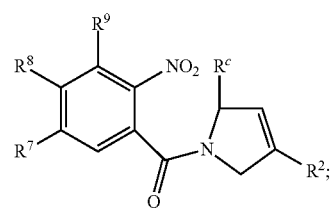

(b) a compound of formula IV:

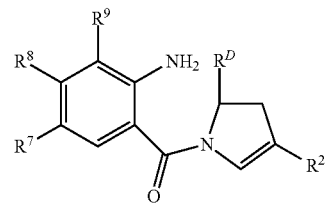

substantially free of

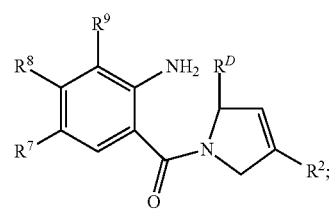

(c) a compound of formula V:

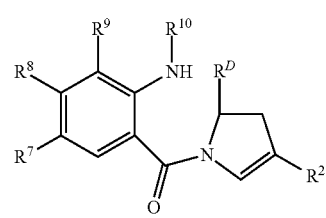

substantially free of

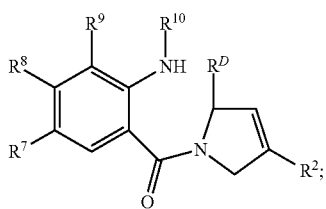

VB and
(d) a compound of formula VI:

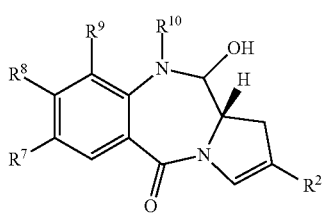

VI substantially free of

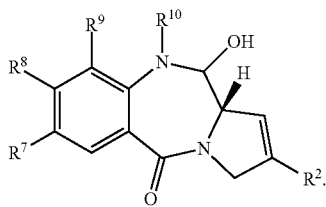

VIB

The term 'substantially free of' means that there is less than 5% by weight of the compound of the undesired compound (i.e., B version) compared to the amount of the desired compound. More preferably, there is less than 1% or 0.1% by weight Definitions Carbamate-based Nitrogen Protecting Groups Carbamate-based nitrogen protecting groups are well known in the art. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

The carbamate-based nitrogen protecting groups used may be those which are sensitive to palladium or sensitive to the conditions needed to add the group:

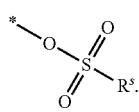

Table 1 provides examples of some such grows ('simple nitrogen protecting groups'):

TABLE 1

| | |
|---|---|
| DBD-Tmoc | ![structure] |
| Cbz (benzyl carbamate) | ![structure] |
| Voc (Vinyl carbamate) | ![structure] |
| 1,1-dimethylpropynyl carbamate | ![structure] |
| Alloc (Allyl carbamate) | ![structure] |
| Moz (p-methoxybenzylcarbamate) | ![structure] |
| Ipaoc (1-isopropylallyl carbamate) | ![structure] |
| PNZ (p-nitrobenzylcarbamate) | ![structure] |
| Coc (Cinnamyl carbamate) | ![structure] |
| 3,4-dimethoxy-6-nitrobenzyl carbamate | ![structure] |

TABLE 1-continued

| Name | Structure |
|---|---|
| Noc (4-nitrocinnamyl carbamate) | 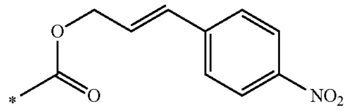 [SMILES: CC(=O)OC/C=C/c1ccc([N+](=O)[O-])cc1] |
| p-bromobenzyl carbamate | 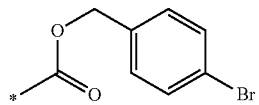 |
| Paloc (3-(3'-pyridyl)prop-2-enyl carbamate) | 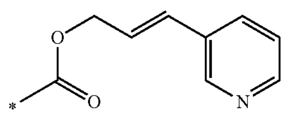 |
| p-chlorobenzyl carbamate | 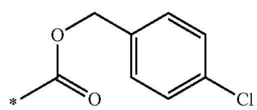 |
| N-hydroxypiperidinyl carbamate | 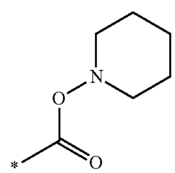 |
| 2,4-dichlorobenzyl carbamate | 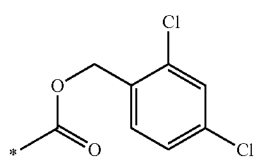 |
| 1,1-dimethyl-2-bromoethyl carbamate | 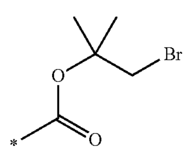 |
| Bic (5-benzylisoxazolylmethyl) | 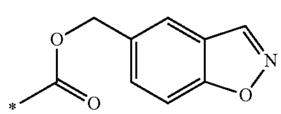 |
| 1,1-dimethyl-2-chloroethyl carbamate | 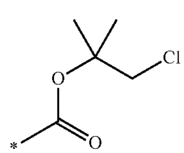 |
| Diphenylmethyl carbamate | 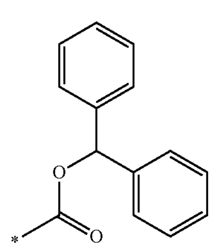 [SMILES: CC(=O)OC(c1ccccc1)c1ccccc1] |

TABLE 1-continued

| Name | Structure |
|---|---|
| 1,1-dimethyl-2-cyanoethyl carbamate | |
| 9-anthrylmethyl carbamate | |
| Propynyl carbamate | |
| S-benzyl carbamate | | where the asterisk indicates the point of attachment to the N10 position.

Also suitable for use in the present invention are carbamate-based nitrogen protecting groups having a complex architecture ('complex nitrogen protecting groups'). These groups may be or may comprise elements of the groups described, for example, in WO 00/12507. These carbamate-based nitrogen protecting groups may include elements that are sensitive to palladium or the conditions used to add the group:

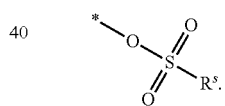

These elements may be any one of the structures listed in Table 1 above.

In one embodiment, the carbamate-based nitrogen protecting group is a linker for connection to an antibody, $R^L$:

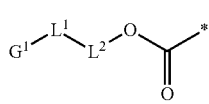

where the asterisk indicates the point of attachment to the N10 position, $G^1$ is a functional group to form a connection to a cell binding agent, $L^1$ is a cleavable linker, $L^2$ is a covalent bond or together with —OC(=O)— forms a self-immolative linker.

In one embodiment, the protecting group $R^L$ is removable from the N10 position thereby to provide the imine or carbinoalmine form of the PBD.

$L^1$ is preferably a cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the PBD molecule is delivered, for example as an antibody drug conjugate. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present invention.

$L^1$ may comprise a contiguous sequence of amino acids. The amino acid sequence may be the target substrate for enzymatic cleavage, thereby allowing release of $R^{10}$ from the N10 position.

In one embodiment, the $L^1$ is cleavable by the action of an enzyme. In one embodiment, the enzyme is an esterase or a peptidase.

In one embodiment, $L^2$ is present and together with C(=O)O forms a self-immolative linker.

In one embodiment, where $L^2$ is cleavable by the action of an enzyme and $L^2$ is present, the enzyme cleaves the bond between $L^1$ and $L^2$.

$L^1$ and $L^2$ may be connected by a bond selected from:
—C(=O)NH—,
—C(=O)O—,
—NHC(=O)—,
—OC(=O)—,
—OC(=O)O—,
—NHC(=O)O—,
—OC(=O)NH—, and
—NHC(=O)NH—.

An amino group of $L^1$ that connects to $L^2$ may be the N-terminus of an amino acid or may be derived from an amino group of an amino acid side chain, for example a lysine amino acid side chain.

An carboxyl group of $L^1$ that connects to $L^2$ may be the C-terminus of an amino acid or may be derived from a carboxyl group of an amino acid side chain, for example a glutamic acid amino acid side chain.

A hydroxy group of $L^1$ that connects to $L^2$ may be derived from a hydroxy group of an amino acid side chain, for example a serine amino acid side chain.

In one embodiment, —C(=O)O— and $L^2$ together form the group:

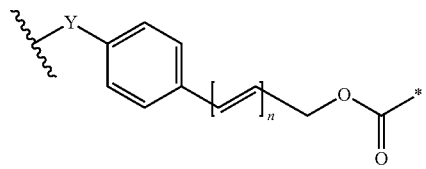

where the asterisk indicates the point of attachment to the N10 position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

The self-immolative linker will allow for release of the protected compound when a remote site is activated, proceeding along the lines shown below (for n=0):

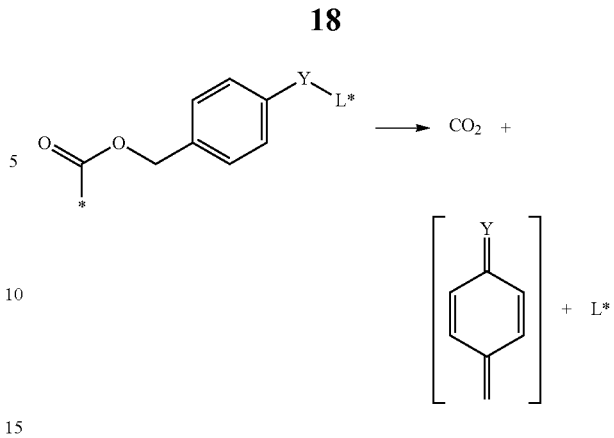

where L* is the activated form of the remaining portion of the linker. These groups have the advantage of separating the site of activation from the compound being protected. As described above, the phenylene group may be optionally substituted.

In one embodiment described herein, the group L* is a linker $L^1$ as described herein, which may include a dipeptide group.

In another embodiment, —C(=O)O— and $L^2$ together form a group selected from:

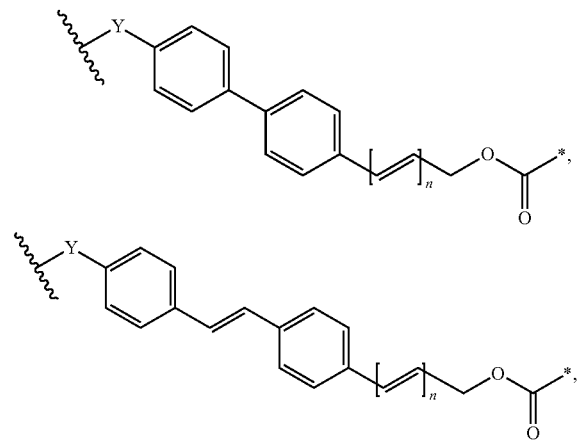

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted. In one embodiment, the phenylene ring having the Y substituent is unsubstituted and the phenylene ring not having the Y substituent is optionally substituted.

In another embodiment, —C(=O)O— and $L^2$ together form a group selected from:

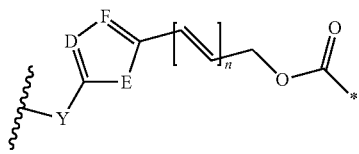

where the asterisk, the wavy line, Y, and n are as defined above, E is O, S or N, D is N, CH, or CR, and F is N, CH, or CR.

In one embodiment, D is N.
In one embodiment, D is CH.
In one embodiment, E is O or S.
In one embodiment, F is CH.
In a preferred embodiment, the linker is a cathepsin labile linker.

In one embodiment, $L^1$ comprises a dipeptide The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-,
-Trp-Cit-.
where Cit is citrulline.

Preferably, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-.

Most preferably, the group —$X_1$—$X_2$— in dipeptide, —NH—$X_1$—$X_2$—CO—, is -Phe-Lys- or -Val-Ala-, In some embodiments, the group —$X_1$—$X_2$— in dipeptide, —NH—$X_1$—$X_2$—CO—, is -Val-Cit-.

Other dipeptide combinations may be used, including those described by Dubowchik et al. (*Bioconjugate Chem.* 2002, 13, 855-869), which is incorporated herein by reference.

In one embodiment, the amino acid side chain is chemically protected, where appropriate. The side chain protecting group may be a group as discussed below in relation to the group $R^L$. The present inventors have established that protected amino acid sequences are cleavable by enzymes. For example, the present inventors have established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In other embodiments of the invention, the amino acids selected are those having no reactive side chain functionality. For example, the amino acids may be selected from: Ala, Gly, Ile, Leu, Met, Phe, Pro, and Val.

In one embodiment, the dipeptide is used in combination with a self-immolative linker. The self-immolative linker may be connected to —$X_2$—.

In one embodiment, the dipeptide is used in combination with a self-immolative linker. The self-immolative linker may be connected to —$X_2$—.

Where a self-immolative linker is present, —$X_2$— is connected directly to the self-immolative linker. Preferably the group —$X_2$—CO— is connected to Y, where Y is NH, thereby forming the group —$X_2$—CO—NH—.

—NH—$X_1$— is connected directly to A. A may comprise the functionality —CO— thereby to form an amide link with —$X_1$—.

In one embodiment, $L^1$ and $L^2$ together with —OC(=O)— comprise the group NH—$X_1$—$X_2$—CO-PABC-. The PABC group is connected directly to the N10 position. Preferably, the self-immolative linker and the dipeptide together form the group —NH-Phe-Lys-CO—NH-PABC-, which is illustrated below:

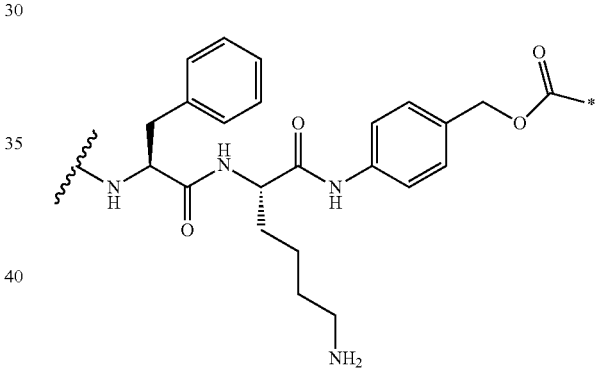

where the asterisk indicates the point of attachment to the N10 position, and the wavy line indicates the point of attachment to the remaining portion of the linker $L^1$ or the point of attachment to A. Preferably, the wavy line indicates the point of attachment to A. The side chain of the Lys amino acid may be protected, for example, with Boc, Fmoc, or Alloc, as described above.

Alternatively, the self-immolative linker and the dipeptide together form the group —NH-Val-Ala-CO—NH-PABC-, which is illustrated below:

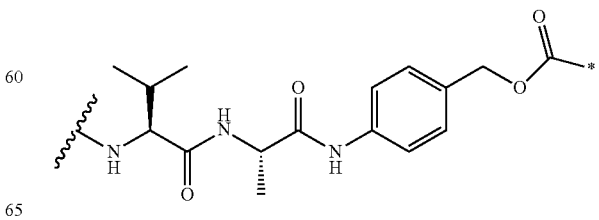

where the asterisk and the wavy line are as defined above.

In one embodiment, $L^2$ together with —OC(=O)— represents:

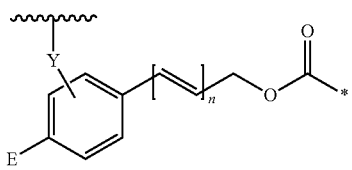

where the asterisk indicates the point of attachment to the N10 position, the wavy line indicates the point of attachment to $L^1$, n is 0 to 3, Y is a covalent bond or a functional group, and E is an activatable group, for example by enzymatic action or light, thereby to generate a self-immolative unit. The phenylene ring is optionally further substituted with one, two or three substituents as described herein. In one embodiment, the phenylene group is optionally further substituted with halo, $NO_2$, R or OR. Preferably n is 0 or 1, most preferably 0.

E is selected such that the group is susceptible to activation, e.g. by light or by the action of an enzyme. E may be —$NO_2$ or glucoronic acid. The former may be susceptible to the action of a nitroreductase, the latter to the action of a β-glucoronidase.

In this embodiment, the self-immolative linker will allow for release of the protected compound when E is activated, proceeding along the lines shown below (for n=0):

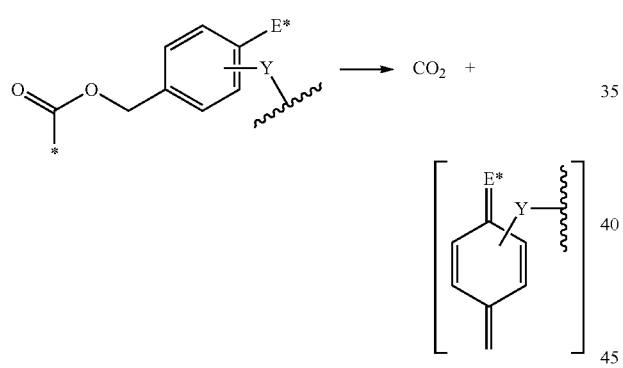

where the asterisk indicates the point of attachment to the N10 position, E* is the activated form of E, and Y is as described above. These groups have the advantage of separating the site of activation from the compound being protected. As described above, the phenylene group may be optionally further substituted.

The group Y may be a covalent bond to $L^1$.

The group Y may be a functional group selected from:
—C(=O)—
—NH—,
—O—
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—, and
—S—.

Where $L^1$ is a dipeptide, it is preferred that Y is —NH— or —C(=O)—, thereby to form an amide bond between $L^1$ and Y. In this embodiment, the dipeptide sequence need not be a substrate for an enzymatic activity.

In another embodiment, G is intended to form a spacer group that is suitable for indirectly connecting $L^1$ to a cell binding agent.

$L^1$ and $G^1$ may be connected by a bond selected from:
—C(=O)NH—,
—C(=O)O—,
—NHC(=O)—,
—OC(=O)—,
—OC(=O)O—,
—NHC(=O)O—,
—OC(=O)NH—, and
—NHC(=O)NH—.

In one embodiment, the functional group $G^1$ is or comprises an amino, carboxylic acid, hydroxy, thiol, or maleimide group for reaction with an appropriate group on the cell binding agent. In a preferred embodiment, $G^1$ comprises a maleimide group.

In one embodiment, the group $G^1$ is an alkyl maleimide group. This group is suitable for reaction with thiol groups, particularly cysteine thiol groups, present in the cell binding agent, for example present in an antibody.

In one embodiment, the group $G^1$ is:

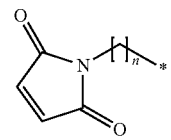

where the asterisk indicates the point of attachment to $L^1$ and n is 0 to 6. In one embodiment, n is 5.

In one embodiment, the group $G^1$ is:

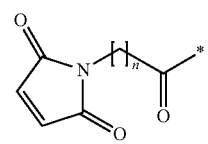

where the asterisk indicates the point of attachment to $L^1$ and n is 0 to 6. In one embodiment, n is 5.

In one embodiment, the group $G^1$ is:

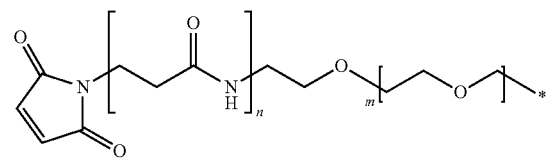

where the asterisk indicates the point of attachment to $L^1$, n is 0 or 1, and m is 0 to 30. In a preferred embodiment, n is 1 and m is 0 to 10, 1 to 7, preferably 3 to 7, and most preferably 3 or 7.

In one embodiment, the group $G^1$ is:

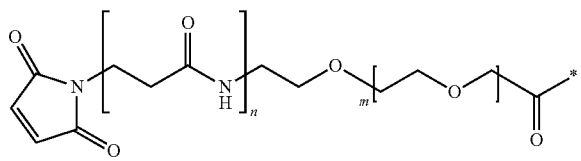

where the asterisk indicates the point of attachment to $L^1$, n is 0 or 1, and m is 0 to 30. In a preferred embodiment, n is 1 and m is 0 to 10, 1 to 7, preferably 3 to 7, and most preferably 3 or 7.

In each of the embodiments above, an alternative functionality may be used in place of the maleimide group shown below:

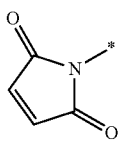

where asterisk indicates the bond to the remaining portion of the G group.

In one embodiment, the maleimide-derived group is replaced with the group:

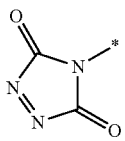

where the asterisk indicates the bond to the remaining portion of the G group.

In one embodiment, the maleimide group is replaced with a group selected from:
—C(=O)OH,
—OH,
—NH$_2$,
—SH,
—C(=O)CH$_2$X, where X is Cl, Br or I,
—CHO,
—NHNH$_2$,
—C≡CH, and
—N$_3$ (azide).

In one embodiment, where $L^1$ is present, $G^1$ is —NH$_2$, —NHMe, —COOH, —OH or —SH.

In one embodiment, where $L^1$ is present, $G^1$ is —NH$_2$ or —NHMe. Either group may be the N-terminal of an $L^1$ amino acid sequence.

In one embodiment, where $L^1$ is present, $G^1$ is —NH$_2$, and $L^1$ is an amino acid sequence —X$_1$—X$_2$—, as defined above in relation to $R^{10}$.

In one embodiment, where $L^1$ is present, $G^1$ is COOH. This group may be the C-terminal of an $L^1$ amino acid sequence.

In one embodiment, where $L^1$ is present, $G^1$ is OH.

In one embodiment, where $L^1$ is present, $G^1$ is SH.

The group $G^1$ may be convertable from one functional group to another. In one embodiment, where $L^1$ is present, $G^1$ is —NH$_2$. This group is convertable to another group $G^1$ comprising a maleimide group. For example, the group —NH$_2$ may be reacted with an acid or an activated acid (e.g. N-succinimide forms) of those $G^1$ groups comprising maleimide shown above.

The group $G^1$ may therefore be converted to a functional group that is more appropriate for reaction with a cell binding agent.

In other embodiments, $R^L$ is a group that is a precursor to the linker that is provided with a functional group.

As noted above, in one embodiment, where $L^1$ is present, $G^1$ is —NH$_2$, —NHMe, —COOH, —OH or —SH. In a further embodiment, these groups are provided in a chemically protected form. The chemically protected form is therefore a precursor to the linker that is provided with a functional group.

In one embodiment, $G^1$ is —NH$_2$ in a chemically protected form. The group may be protected with a carbamate protecting group. The carbamate protecting group may be selected from the group consisting of:
Alloc, Fmoc, Boc, Troc, Teoc, Cbz and PNZ.

Preferably, where $G^1$ is —NH$_2$, it is protected with an Alloc or Fmoc group.

In one embodiment, particularly where the compound is a dimer, the nitrogen protecting group for one of the PBD units is a group $R^L$ and the nitrogen protecting group for the other of the PBD units is a capping group, $R^{Cap}$:

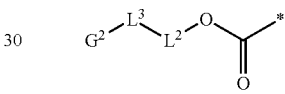

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

The protecting group $R^C$ is removable from the N10 position thereby to provide the imine or carbinolamine form of the PBD. The term "capping group" is used to indicate that $R^C$ is prevented from reacting with a cell binding agent, such as an antibody. Instead, the group $R^L$ is for connection to a cell binding agent.

Where $L^3$ and $L^2$ are both covalent bonds, $G^2$ and —OC(=O)— together form a carbamate protecting group such as shown above in Table 1.

$L^1$ is as defined above in relation to $R^L$.
$L^2$ is as defined above in relation to $R^L$.

In one embodiment $L^3$ is a cleavable linker $L^1$, and $L^2$, together with OC(=O), forms a self-immolative linker. In this embodiment, $G^2$ is Ac (acetyl) or Moc, or a carbamate protecting group selected from:
Alloc, Fmoc, Boc, Troc, Teoc, Psec, Cbz and PNZ.

In one embodiment $L^3$ is a cleavable linker $L^1$, and $L^2$, together with OC(=O), forms a self-immolative linker. In this embodiment, $G^2$ together with OC(=O), is a carbamate protecting group selected from Table 1 above.

$G^2$ is different to $G^1$. Furthermore, it is preferred that $G^1$ is removable under conditions that do not remove $G^1$.

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, $—CH=CH_2$), 1-propenyl ($—CH=CH—CH_3$), 2-propenyl (allyl, $—CH—CH=CH_2$), isopropenyl (1-methylvinyl, $—C(CH_3)=CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (ethinyl, $—C≡CH$) and 2-propynyl (propargyl, $—CH_2—C≡CH$).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_5$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

N₁: pyrrole (azole) (C₅), pyridine (azine) (C₆);
O₁: furan (oxole) (C₅);
S₁: thiophene (thiole) (C₅);
N₁O₁: oxazole (C₅), isoxazole (C₅), isoxazine (C₆);
N₂O₁: oxadiazole (furazan) (C₅);
N₃O₁: oxatriazole (C₅);
N₁S₁: thiazole (C₅), isothiazole (C₅);
N₂: imidazole (1,3-diazote) (C₅), pyrazole (1,2-diazole) (C₆ₗ), pyridazine (1,2-diazine) (C₆), pyrimidine (1,3-diazine) (C₆) (e.g., cytosine, thymine, uracil), pyrazine (1,4-diazine) (C₆);
N₃: triazole (C₅), triazine (C₆); and,
N₄: tetrazole (C₅).

Examples of heteroaryl which comprise fused rings, include, but are not limited to:

C₉ (with 2 fused rings) derived from benzofuran (O₁), isobenzofuran (O₁), indole (N₁), isoindole (N₁), indolizine (N₁), indoline (N₁), isoindoline (N₁), purine (N₄) (e.g., adenine, guanine), benzimidazole (N₂), indazole (N₂), benzoxazole (N₁O₁), benzisoxazole (N₁O₁), benzodioxole (O₂), benzofurazan (N₂O₁), benzotriazole (N₃), benzothiofuran (S₁), benzothiazole (N₁S₁), benzothiadiazole (N₂S);

C₁₀ (with 2 fused rings) derived from chromene (O₁), isochromene (O₁), chroman (O₁), isochroman (O₁), benzodioxan (O₂), quinoline (N₁), isoquinoline (N₁), quinolizine (N₁), benzoxazine (N₁O₁), benzodiazine (N₂), pyridopyridine (N₂), quinoxaline (N₂), quinazoline (N₂), cinnoline (N₂), phthalazine (N₂), naphthyridine (N₂), pteridine (N₄);

C₁₁ (with 2 fused rings) derived from benzodiazepine (N₂);

C₁₃ (with 3 fused rings) derived from carbazole (N₁), dibenzofuran (O₁), dibenzothiophene (S₁), carboline (N₂), perimidine (N₂), pyridoindole (N₂); and, C₁₄ (with 3 fused rings) derived from acridine (N₁), xanthene (O₁), thioxanthene (S₁), oxanthrene (O₂), phenoxathiin (O₁S₁), phenazine (N₂), phenoxazine (N₁O₁), phenothiazine (N₁S₁), thianthrene (S₂), phenanthridine (N₁), phenanthroline (N₂), phenazine (N₂).

The above groups, whether alone or part of another substituent, may themselves optionally be substituted with one or more groups selected from themselves and the additional substituents listed below.

N atoms in heterocyclyl and heteroaryl groups may be substituted by with C₁₋₁₂ alkyl, where appropriate.

Halo: —F, —Cl, —Br, and —I.

Hydroxy: —OH.

Ether: —OR, wherein R is an ether substituent, for example, a C₁₋₇ alkyl group (also referred to as a C₁₋₇ alkoxy group, discussed below), a C₃₋₂₀ heterocyclyl group (also referred to as a C₃₋₂₀ heterocyclyloxy group), or a C₅₋₂₀ aryl group (also referred to as a C₅₋₂₀ aryloxy group), preferably a C₁₋₇alkyl group.

Alkoxy: —OR, wherein R is an alkyl group, for example, a C₁₋₇ alkyl group. Examples of C₁₋₇ alkoxy groups include, but are not limited to, —OMe (methoxy), —OEt (ethoxy), —O(nPr) (n-propoxy), —O(iPr) (isopropoxy), —O(nBu) (n-butoxy), —O (sBu) (sec-butoxy), —O(iBu) (isobutoxy), and —O(tBu) (tert-butoxy).

Acetal: —CH(OR¹)(OR²), wherein R¹ and R² are independently acetal substituents, for example, a C₁₋₇ alkyl group, a C₃₋₂₀ heterocyclyl group, or a C₅₋₂₀ aryl group, preferably a C₁₋₇ alkyl group, or, in the case of a "cyclic" acetal group, R¹ and R², taken together with the two oxygen atoms to which they are attached, and the carbon atoms to which they are attached, form a heterocyclic ring having from 4 to 8 ring atoms. Examples of acetal groups include, but are not limited to, —CH(OMe)₂, —CH(OEt)₂, and —CH(OMe)(OEt).

Hemiacetal: —CH(OH)(OR¹), wherein R¹ is a hemiacetal substituent, for example, a C₁₋₇ alkyl group, a C₃₋₂₀ heterocyclyl group, or a C₅₋₂₀ aryl group, preferably a C₁₋₇ alkyl group. Examples of hemiacetal groups include, but are not limited to, —CH(OH)(OMe) and —CH(OH)(OEt).

Ketal: —CR(OR¹)(OR²), where R¹ and R² are as defined for acetals, and R is a ketal substituent other than hydrogen, for example, a C₁₋₇ alkyl group, a C₃₋₂₀ heterocyclyl group, or a C₅₋₂₀ aryl group, preferably a C₁₋₇ alkyl group. Examples ketal groups include, but are not limited to, —C(Me)(OMe)₂, —C(Me)(OEt)₂, —C(Me)(OMe)(OEt), —C(Et)(OMe)₂, —C(Et)(OEt)₂, and —C(Et)(OMe)(OEt).

Hemiketal: —CR(OH)(OR¹), where R¹ is as defined for hemiacetals, and R is a hemiketal substituent other than hydrogen, for example, a C₁₋₇ alkyl group, a C₃₋₂₀ heterocyclyl group, or a C₅₋₂₀ arylgroup, preferably a C₁₋₇ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, C₁₋₇ alkyl group, a C₃₋₂₀ heterocyclyl group, or a C₅₋₂₀ aryl group, preferably hydrogen or a C₁₋₇ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a C₁₋₇ alkyl group (also referred to as C₁₋₇ alkylacyl or C₁₋₇alkanoyl), a C₃₋₂₀ heterocyclyl group (also referred to as C₃₋₂₀ heterocyclylacyl), or a C₅₋₂₀ aryl group (also referred to as C₅₋₂₀ arylacyl), preferably a C₁₋₇ alkyl group. Examples of acyl groups include, but are not limited to, —C(=O)CH₃ (acetyl), —C(=O)CH₂CH₃ (propionyl), —C(=O)C(CH₃)₃ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a C₁₋₇ alkyl group, a C₃₋₂₀ heterocyclyl group, or a C₅₋₂₀ aryl group, preferably a C₁₋₇ alkyl group. Examples of ester groups include, but are not limited to, —C(=O)OCH₃, —C(=O)OCH₂CH₃, —C(=O)OC(CH₃)₃, and —C(=O)OPh.

Acyloxy (reverse ester): —OC(=O)R, wherein R is an acyloxy substituent, for example, a C₁₋₇ alkyl group, a C₃₋₂₀ heterocyclyl group, or a C₅₋₂₀ aryl group, preferably a C₁₋₇ alkyl group. Examples of acyloxy groups include, but are not limited to, —OC(=O)CH₃ (acetoxy), —OC(=O)CH₂CH₃, —OC(=O)C(CH₃)₃, —OC(=O)Ph, and —OC(=O)CH₂Ph.

Oxycarboyloxy: —OC(=O)OR, wherein R is an ester substituent, for example, a C₁₋₇ alkyl group, a C₃₋₂₀ heterocyclyl group, or a C₅₋₂₀ aryl group, preferably a C₁₋₇ alkyl group. Examples of ester groups include, but are not limited to, —OC(=O)OCH₃, —OC(=O)OCH₂CH₃, —OC(=O)OC(CH₃)₃, and —OC(=O)OPh.

Amino: —NR¹R², wherein R¹ and R² are independently amino substituents, for example, hydrogen, a C₁₋₇ alkyl group (also referred to as C₁₋₇ alkylamino or di-C₁₋₇ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—$NH_2$), secondary (—$NHR^1$), or tertiary (—$NHR^1R^2$), and in cationic form, may be quaternary (—$^+NR^1R^2R^3$). Examples of amino groups include, but are not limited to, —$NH_2$, —$NHCH_3$, —$NHC(CH_3)_2$, —$N(CH_3)_2$, —$N(CH_2CH_3)_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —$C(=O)NR^1R^2$, wherein $R^1$ and $R^2$ are independently amino substituents, as defined for amino groups. Examples of amido groups include, but are not limited to, —$C(=O)NH_2$, —$C(=O)NHCH_3$, —$C(=O)N(CH_3)_2$, —$C(=O)NHCH_2CH_3$, and —$C(=O)N(CH_2CH_3)_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —$C(=S)NR^1R^2$, wherein $R^1$ and $R^2$ are independently amino substituents, as defined for amino groups. Examples of amido groups include, but are not limited to —$C(=S)NH_2$, —$C(=S)NHCH_3$, —$C(=S)N(CH_3)_2$, and —$C(=S)NHCH_2CH_3$.

Acylamido (acylamino): —$NR^1C(=O)R^2$, wherein $R^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —$NHC(=O)CH_3$, —$NHC(=O)CH_2CH_3$, and —$NHC(=O)Ph$. $R^1$ and $R^2$ may together form a cyclic structure, as in, for example, succinimidyl, maleimidyl, and phthalimidyl:

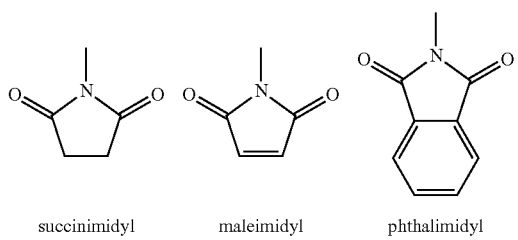

succinimidyl    maleimidyl    phthalimidyl

Aminocarbonyloxy: —$OC(=O)NR^1R^2$, wherein $R^1$ and $R^2$ are independently amino substituents, as defined for amino groups. Examples of aminocarbonyloxy groups include, but are not limited to, —$OC(=O)NH_2$, —$OC(=O)NHMe$, —$OC(=O)NMe_2$, and —$OC(=O)NEt_2$.

Ureido: —$N(R^1)CONR^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —$NHCONH_2$, —$NHCONHMe$, —$NHCONHEt$, —$NHCONMe_2$, —$NHCONEt_2$, —$NMeCONH_2$, —$NMeCONHMe$, —$NMeCONHEt$, —$NMeCONMe_2$, and —$NMeCONEt_2$.

Guanidino: —$NH—C(=NH)NH_2$.

Tetrazolyl: a five membered aromatic ring having four nitrogen atoms and one carbon atom,

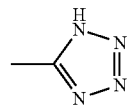

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —$C(=NR)NR_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —$C(=NH)NH_2$, —$C(=NH)NMe_2$, and —$C(=NMe)NMe_2$.

Nitro: —$NO_2$.

Nitroso: —NO.

Azido: —$N_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —$SSCH_3$ and —$SSCH_2CH_3$.

Sulfine (sulfinyl, sulfoxide): —$S(=O)R$, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —$S(=O)CH_3$ and —$S(=O)CH_2CH_3$.

Sulfone (sulfonyl): —$S(=O)_2R$, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —$S(=O)_2CH_3$ (methanesulfonyl, mesyl), —$S(=O)_2CF_3$ (triflyl), —$S(=O)_2CH_2CH_3$ (esyl), —$S(=O)_2C_4F_9$ (nonaflyl), —$S(=O)_2CH_2CF_3$ (tresyl), —$S(=O)_2CH_2CH_2NH_2$ (tauryl), —$S(=O)_2Ph$ (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —$S(=O)OH$, —$SO_2H$.

Sulfonic acid (sulfo): —$S(=O)_2OH$, —$SO_3H$.

Sulfinate (sulfinic acid ester): —$S(=O)OR$; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—

CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated $C_{3-12}$ alkylene groups ($C_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), and cyclohexenylene (e.g. 2-cyclohexen-1,4-ylene; 3-cyclohexen-1,2-ylene; 2,5-cyclohexadien-1,4-ylene).

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Preferably compounds of formula VI have the following stereochemistry at the C11 position:

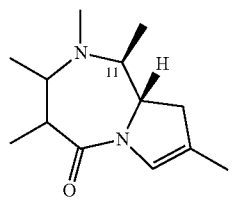

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

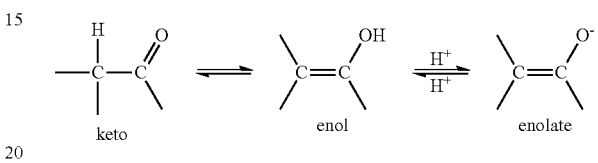

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., J. Pharm. Sci., 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

General Synthetic Routes

Compounds of formula II:

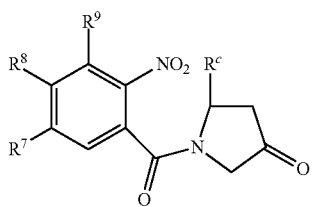

II can be synthesised from compounds of formula A:

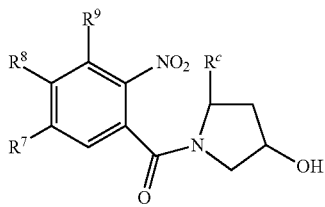

A by oxidation for example using: TCCA and TEMPO; BAIB and TEMPO; TPAP; Dess-Martin conditions; or Swern conditions.

Compounds of formula A may be synthesised by coupling appropriate compounds of formulae B and C, or activated derivatives thereof:

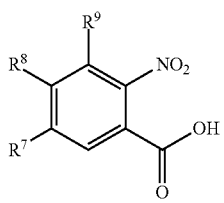

B

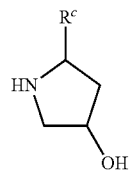

C

Compound of formulae B and C are generally commercially available or readily synthesisable.

If compound B is a dimer, then this may be synthesised as described in WO 00/12508.

Further Embodiments

The following further embodiments may be combined with each other as appropriate.

$R^7$ and $R^8$ $R^7$ and $R^8$ are independently selected from: $OR^A$, where $R^A$ is selected from $C_{1-4}$ saturated alkyl, optionally substituted by phenyl, which phenyl may bear a chloro substituent, pyridyl and furanyl; chloro; $NH_2$; and $-CH_2-O-C(=O)Me$; or $R^7$ and $R^8$ together form a group $-O-(CH_2)_m-O-$, where m is 1 or 2.

In some embodiments, $R^7$ and $R^8$ may independently be $OR^A$, where $R^A$ is selected from $C_{1-4}$ saturated alkyl, optionally substituted by phenyl, pyridyl and furanyl.

In some of these embodiments, $R^A$ is unsubstituted $C_{1-4}$ saturated alkyl, i.e. methyl, ethyl, propyl and butyl. It may be preferred that $R^A$ is methyl.

In other of these embodiments, $R^A$ is $C_{1-4}$ saturated alkyl substituted by a group selected from phenyl, pyridyl and furanyl. It may be preferred that the substituent is phenyl. It may be further preferred that $R^A$ is phenyl-methyl (i.e. benzyl).

If the compound is a dimer, $R^7$ is $OR^A$, with the embodiments as discussed above. The group $R^7$ may be the same on both PBD monomer units, or may be different. It is preferred that they are the same.

When the compound is a dimer, $R^8$ on each PBD monomer form together a dimer bridge having the formula $-X-R''-X-$ linking the monomers, where $R''$ is a $C_{3-12}$ saturated alkylene group, which group may be interrupted by O, S, NH, NMe, phenylene or pyridylene, where the phenylene and pyridylene groups are optionally substituted by $NH_2$, and each X is independently selected from O, S, or NH.

Each X is preferably the same and are preferably both O.

$R''$ is a $C_{3-12}$ saturated alkylene group, which group may be interrupted by O, S, NH, NMe, phenylene or pyridylene, where the phenylene and pyridylene groups are optionally substituted by $NH_2$. In some embodiments, $R''$ is a $C_{3-12}$ saturated alkylene group, which group may be interrupted by O, S, NH, phenylene or pyridylene.

In some further embodiments, $R''$ is selected from a $C_3$, $C_5$, $C_7$, $C_9$ and a $C_{11}$ alkylene group. It may be preferred that $R''$ is selected from a $C_3$, $C_5$ and a $O_7$ alkylene group. It may be further preferred that $R''$ is selected from a $C_3$ and a $C_5$ alkylene group.

The alkylene groups listed above may be unsubstituted linear aliphatic saturated alkylene groups.

The alkylene groups listed above may be optionally interrupted by group may be interrupted by O, S, NH, NMe, phenylene or pyridylene. The interrupting group may be any position in the chain as long as there is a carbon atom on each side of the group.

In some embodiments, it may be preferred that the alkylene group is not interrupted.

$R^9$ $R^9$ is selected from H, methyl and methoxy. In some embodiments, $R^9$ is hydrogen.

$R^S$ $R^S$ is selected from $CF_3$, $CH_3$ and

When $R^S$ is $CF_3$, the C2 group is triflate.
When $R^S$ is $CH_3$, the C2 group is mesylate.
When $R^S$ is

the C2 group is tosylate.

When $R^S$ is $(CF_2)_3CF_3$, the C2 group is nonaflate.

In some embodiments, $R^S$ is preferably $CF_3$.

$R^C$ $R^C$ is selected:

(i) —C(=O)—$OR^{C1}$, where $R^{C1}$ is a saturated $C_{1-4}$ alkyl group;
(ii) —$CH_2$—O—C(=O)$R^{C2}$, where $R^{C2}$ is methyl or phenyl;
(iii) —$CH_2$—O—Si—$(R^{Si1})(R^{Si2})(R^{Si3})$, where $R^{Si1}$, $R^{Si2}$, $R^{Si3}$ are independently selected from $C_{1-6}$ a saturated alkyl group and a phenyl group; and
(iv) —C(—$YR^{C3}$) (—$YR^{C4}$) where each Y is independently O or S, and where $R^{C3}$ and $R^{C4}$ are independently a saturated $C_{1-4}$ alkyl group, or together form a $C_{2-3}$ alkylene.

$R^{C1}$ is a saturated $C_{1-4}$ alkyl group, i.e. methyl, ethyl, propyl and butyl. In some embodiments, $R^{C1}$ is preferably methyl or ethyl, and more preferably methyl.

When $R^{C2}$ is methyl, $R^C$ comprises an acetate group. When $R^{C2}$ is phenyl, $R^C$ comprises a benzoate group. In some embodiments, it is preferred $R^{C2}$ is methyl.

—Si—$(R^{Si1})(R^{Si2})(R^{Si3})$ is a silyl protecting group, which are well known in the art. Groups of particular interest in the present invention are:

| | |
|---|---|
| TMS | —Si$(CH_3)_3$ |
| TES | —Si$(C_2H_5)_3$ |
| TIPS | —Si(i-Pr)$_3$ |
| TBDMS | —Si$(CH_3)_2$(t-Bu) |
| IPDMS | —Si$(CH_3)_2$(i-Pr) |
| DEIPS | —Si$(C_2H_5)_2$(i-Pr) |
| TBDPS | —Si$(Ph)_2$(t-Bu) |

In some embodiments, preferred silyl protecting groups are TBDMS and TBDPS, or which TBDMS is more preferred.

$R^{C3}$ may be a saturated $C_{1-4}$ alkyl group, i.e. methyl, ethyl, propyl and butyl. In some embodiments, $R^{C3}$ is preferably methyl or ethyl, and more preferably methyl.

$R^{C4}$ may be a saturated $C_{1-4}$ alkyl group, i.e. methyl, ethyl, propyl and butyl. In some embodiments, $R^{C4}$ is preferably methyl or ethyl, and more preferably methyl.

When $R^{C3}$ and $R^{C4}$ together form a $C_{2-3}$ alkylene group, $R^C$ is selected from:

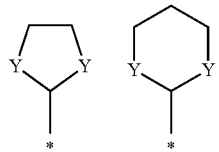

In some embodiments, Y is O. In other embodiments, Y is S.

In some embodiments, it is preferred that $R^C$ is —Si—$(R^{Si1})(R^{Si2})(R^{Si3})$.

Second Aspect

In the method of the second aspect, the compound of formula II is treated with the appropriate anhydride and anhydrous 2,6-lutidine or anhydrous 2-6-$^t$Bu-pyridine at a temperature of −35° C. or lower in a dry organic solvent under a inert atmosphere.

Therefore, if the compound of formula I has a triflate group at C2, then the compound of formula II is treated with triflic anhydride. If the compound of formula I has a mesylate group at C2, then the compound of formula II is treated with mesyl anhydride. If the compound of formula I has a tosylate group at C2, then the compound of formula II is treated with tosyl anhydride. If the compound of formula I has a nonaflate group at C2, then the compound of formula II is treated with nonafluorobutane sulphonic anhydride.

The base may be 2,6-lutidine or 2-6-$^t$Bu-pyridine. It may be preferred that the base is 2-6-lutidine.

The reaction may be carried out at a temperature of −35° C. or lower. In some embodiments, the reaction is carried out at a temperature of −40° C., −45° C., or −50° C. In further embodiments, the reaction is carried out at −78° C.

A $R^2$ is selected from:
(i) an optionally substituted $C_{5-20}$ aryl group;
(ii) an optionally substituted $C_{1-5}$ alkyl group (including a $C_{2-5}$ alkenyl group and a $C_{2-5}$ alkynyl group); and
(iii) H.

In some embodiments, $R^2$ is an optionally substituted $C_{5-20}$ aryl group.

In some of these embodiments, $R^2$ is preferably an optionally substituted $C_{5-7}$ aryl group, and most preferably an optionally substituted phenyl group.

In other of these embodiments, $R^2$ is a $C_{9-12}$ aryl group, for example naphth-1-yl or naphth-2-yl, preferably naphty-2-yl Further examples of $C_{9-12}$ aryl groups include quinolinyl, for example, quinolin-2-yl, quinolin-3-yl and quinolin-6-yl.

In other of these embodiments, $R^2$ is a $C_{5-7}$ heteroaryl group, for example furanyl, thiophenyl and pyridyl. Of these thiophenyl is preferred, for example, thiophen-2-yl and thiophen-3-yl.

The $C_{5-20}$ aryl group may bear any substituent group. It preferably bears from 1 to 3 substituent groups, with 1 and 2 being more preferred, and singly substituted groups being most preferred.

Preferred $C_{5-20}$ aryl substituents, particularly for phenyl, include: halo (e.g. F, Cl, Br); $C_{1-7}$ alkoxy (e.g. methoxy, ethoxy); di-$C_{1-4}$ alkylamino-$C_{1-7}$ alkoxy; $C_{1-7}$ alkyl (e.g. methyl, trifluoromethyl, ethyl, propyl, t-butyl); bis-oxy-alkylene (e.g. bis-oxy-methylene, —O—$CH_2$—O—); and N—$C_{1-4}$ alkyl piperazinyl.

Particularly preferred substituted $C_{5-20}$ aryl groups include, but are not limited to, 4-methyl-phenyl, 4-methoxyphenyl, 3-methoxyphenyl, 4-fluoro-phenyl, 3,4-bisoxymethylene-phenyl, 4-triflouoromethylphenyl, 4-methylthiophenyl, 4-cyanophenyl, 4-phenoxyphenyl, 4-N-methyl piperazinyl phenyl, 4-N,N-dimethyl amino propxyphenyl, 4-N,N-dimethyl amino ethoxyphenyl, 6-methoxynaphth-2-yl, and 6-ethoxynaphth-2-yl.

Particularly preferred unsubstituted $C_{5-20}$ aryl groups include, but are not limited to thiophen-2-yl, napth-2-yl, quinolin-3-yl and quinolin-6-yl.

The aryl groups can be installed with the appropriate boronic acid (or pinacol ester) at 0° C. using tetrakis palladium triphenylphosphine as catalyst and sodium carbonate as base. Hindered or electron deficient boronic acids may require heating to 60° C., if higher temperatures or prolonged heating is required triethylamine is preferred to sodium carbonate as base.

In some embodiments, $R^2$ is an optionally substituted $C_{1-5}$ alkyl group (including a $C_{2-5}$ alkenyl group and a $C_{2-5}$ alkynyl group).

In some of these embodiments, $R^2$ is an optionally substituted $C_{1-5}$ (saturated) alkyl group (e.g. methyl, ethyl, propyl, butyl, pentyl), which may be cyclic (e.g. cyclopropyl, cyclobutyl, cyclopentyl). Preferred groups may include methyl, ethyl and propyl, as well as cyclopropyl.

In others of these embodiments, $R^2$ is an optionally substituted $C_{2-5}$ alkenyl group, which may be cyclic. The group may be fully unsaturated or partially unsaturated, and therefore may include ethenyl (—CH=CH$_2$), propenyl (e.g. —CH=CH—CH$_3$, —CH$_2$—CH=CH$_2$, —C(=CH$_2$)—CH$_3$), butenyl (e.g. —CH=CH—CH$_2$—CH$_3$, —CH$_2$—CH=CH—CH$_3$, —CH$_2$—CH$_2$—CH=CH$_2$, —C(=CH$_2$)—CH$_2$—CH$_3$), butadienyl (e.g. —CH=CH—CH=CH$_2$, —C(=CH$_2$)—CH=CH$_2$), pentenyl (e.g. —CH=CH—CH$_2$—CH$_2$—CH$_3$, —CH$_2$—CH=CH—CH$_2$—CH$_3$, —CH$_2$—CH$_2$—CH=CH—CH$_3$, —CH$_2$—CH$_2$—CH$_2$—CH=CH$_2$, —C(=CH$_2$)—CH$_2$—CH$_2$—CH$_3$), pentadienyl (e.g. —CH=CH—CH=CH—CH$_3$, —CH$_2$—CH=CH—CH=CH$_2$, —C(=CH$_2$)—CH=CH—CH$_3$) and cyclopentenyl.

In others of these embodiments, $R^2$ is an optionally substituted $C_{2-5}$ alkynyl group. The group may be fully unsaturated or partially unsaturated, and therefore may include ethynyl (—C≡CH), propynyl (e.g. —C≡C—CH$_3$, —CH$_2$—C≡CH), butynyl (e.g. —C≡C—CH$_2$—CH$_3$, —CH$_2$—C≡C—CH$_3$, —CH$_2$—CH$_2$—C≡CH), pentynyl (e.g. —C≡C—CH$_2$—CH$_2$—CH$_3$, —CH$_2$—C≡C—CH$_2$—CH$_3$, —CH$_2$—CH$_2$—C≡C—CH$_3$, —CH$_2$—CH$_2$—CH$_2$—C≡CH), and cyclopentynyl.

For groups above that contain unsaturation, at least one of the unsaturated bonds may be conjugated to the double bond present between C2 and C3 in the PBD's C-ring. It may be the case that all the unsaturated bonds are conjugated.

The optional substituents for the optionally substituted $C_{1-5}$ alkyl groups (including $C_{2-5}$ alkenyl group and $C_{2-5}$ alkynyl groups), may include, in particular:

(i) $C_{5-20}$ aryl groups, which themselves may be substituted as discussed above for $R^2$ groups in themselves;

(ii) cyano (—CN);

(iii) amido (—C(=O)—NR$^1$R$^2$);

(iv) ester (—C(=O)—OR).

(v) —OR;

(vi) boronic groups suitable for coupling a further group, such as:

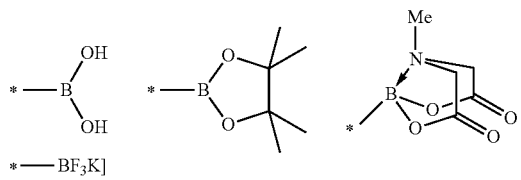

(vii) tin groups, suitable for coupling a further group, such as —Sn(R)$_3$ where R is a $C_{1-7}$ alkyl group.

The amido group is as defined above. In some embodiments, the amino substituents may preferably be selected from $C_{1-7}$ alkyl or more preferably $C_{1-4}$ alkyl, such that the amido group is, for example, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$ The ester group is as defined above. In some embodiments, the ester substituent is a $C_{1-7}$ alkyl group or a $C_{1-4}$ alkyl group, such that the ester group is, for example, —C(=O)OCH$_3$, —C(=O)OCH$_2$CH$_3$ and —C(=O)OC(CH$_3$)$_3$.

The ether group is as defined above. In some embodiments, the ether substituent is a $C_{1-7}$ alkyl group or a $C_{1-4}$ alkyl group, such that the ether group is, for example, —OCH$_3$, —OCH$_2$CH$_3$ and —OC(CH$_3$)$_3$.

In some embodiments, $R^2$ is H.

$R^2$ groups of particular interest include:

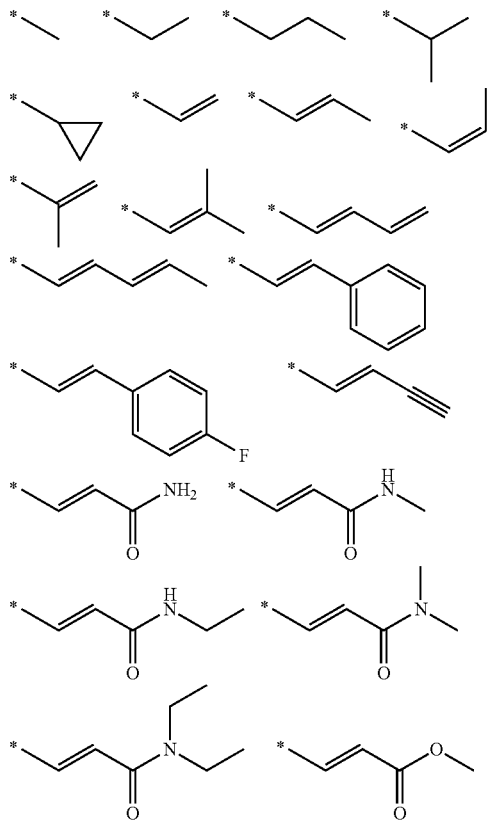

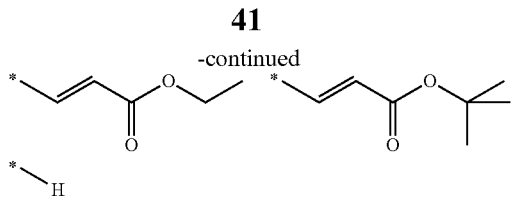

B

If $R^C$ is —CH$_2$—O—C(=O)R$^{C2}$ or —CH$_2$—O—Si—(R$^{Si1}$)(R$^{Si2}$)(R$^{Si3}$) then the conversion of III to IV is by reduction of the nitro group. If $R^C$ is —CH$_2$—O—C(=O)R$^{C2}$, this reduction is carried out by using zinc in acetic acid. Alternatives include Cd/Pb couple, sodium dithionite or tin II chloride. If $R^C$ is —CH$_2$—O—Si—(R$^{Si1}$)(R$^{Si2}$)(R$^{Si3}$) then this reduction is carried out using zinc in a weak acid, e.g. 5% formic acid in ethanol. If $R^C$ is —C(—YR$^{C3}$)(—YR$^{C4}$), this reduction may be carried out using Cd/Pb couple, sodium dithionite or tin II chloride.

If $R^C$ is —C(=O)—OR$^{C1}$, then the conversion of III to IV is achieved by first reducing of the ester and reprotection as an acetate or silyl ether. The reduction can be achieved by standard means, for example with LiBH$_4$, or LiEt$_3$BH$_4$. Reprotection as an aceate can be achieved, for example, by reaction with acetyl chloride; reprotection as a benzoate can be achieved, for example, by reaction with benzoyl chloride; reprotection as a silyl ether can be achieved, for example, by reaction with the appropriate silyl chloride in DMF in the presence of imidazole.

C $R^{10}$ is a carbamate-based nitrogen protecting group, which is palladium-labile, or contains a moiety which is palladium-labile.

If $R^{10}$ is a simple nitrogen protecting group, it may be preferably selected from a group containing the moiety:

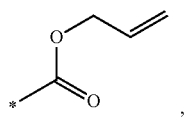

such as Alloc, Ipaoc, Coc, Noc, Paloc, and may more preferably be Alloc.

If $R^{10}$ is a complex nitrogen protecting group, it may be preferably a group which is cathepsin labile.

The nitrogen protecting group is preferably introduced by reaction of IV with triphosgene to obtain the isocyanate followed by reaction with R$^{10}$—OH. The reaction of IV with triphosgene should be carried out in an anhydrous and non-hydroxylic organic solvent, which is preferably non-polar. Suitable solvents include anhydrous dichloromethane and anhydrous toluene. The reaction may be carried out at room temperature. The subsequent reaction with R$^{10}$—OH should be carried in an anhydrous and non-hydroxylic organic solvent, which is preferably non-polar. Suitable solvents include anhydrous dichloromethane and anhydrous toluene. The reaction should be carried out in the presence of a base is present, and suitable bases include pyridine or TEA. The reaction may be carried out at 0° C., or at a higher temperature to increase the rate of reaction.

D

The PBD B-ring is preferably closed using Dess-Martin periodinane.

EXAMPLES

General Information

Reaction progress was monitored by thin-layer chromatography (TLC) using Merck Kieselgel 60 F254 silica gel, with fluorescent indicator on aluminium plates. Visualisation of TLC was achieved with UV light or iodine vapour unless otherwise stated. Flash chromatography was performed using Merck Kieselgel 60 F254 silica gel. Extraction and chromatography solvents were bought and used without further purification from Fisher Scientific, U.K. All chemicals were purchased from Aldrich, Lancaster or BDH.

The LC/MS conditions were as follows: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes.

Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm.

Example 1

(a)

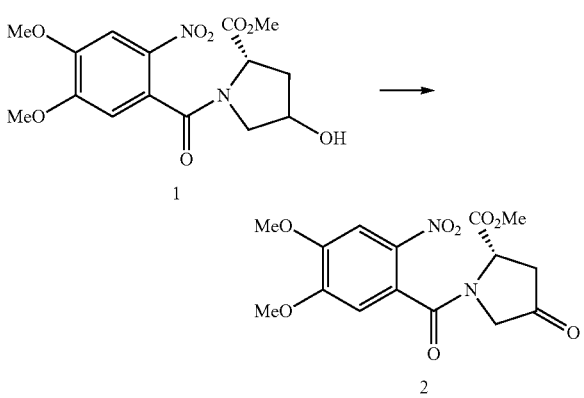

Compound 1 is disclosed as Compound 3 of WO 2004/043963.

Solid TCCA (18 g, 77.4 mmol, 1.1 eq) was added portionwise to a solution of TEMPO (730 mg, 4.67 mmol, 0.07 eq) and alcohol 1 (25 g, 70.5 mmol, 1 eq), in normal DCM (500 mL) at 0° C. A slight exotherm was observed. The reaction was deemed complete by TLC (Ethyl Acetate) and LC/MS (2.38 min (ES+) m/z (relative intensity) 353.34 ([M+H]$^+$, 100)) after 30 minutes. The suspension was filtered through celite and washed with DCM. The filtrate was washed with aqueous sodium bisulfite, followed by saturated NaHCO$_3$ (caution, vigorous effervescence), brine (100 mL) and dried (MgSO$_4$). Filtration and evaporation of the solvent in vacuo afforded the crude product which was purified by flash column chromatography (elution: 20:80 v/v n-hexane/EtOAc) to afford the ketone 2 as a white solid (20 g, 80%).

Analytical Data: $[\alpha]^{26}_D$=15° (c=0.2, CHCl$_3$); MS (ES$^+$) m/z (relative intensity) 353.34 ([M+H]$^{+\cdot}$, 100);); IR (ATR, CHCl$_3$) 1748, 1642, 1518, 1425, 1335, 1222, 1176, 1063, 1032, 986, 857, 785, 756 cm$^{-1}$;

(b)

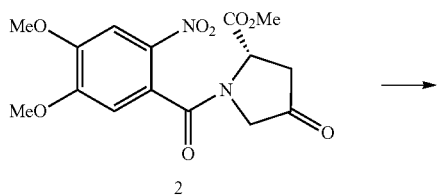

2

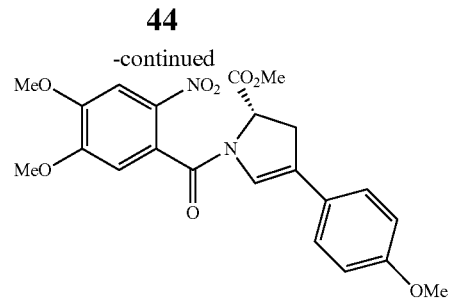

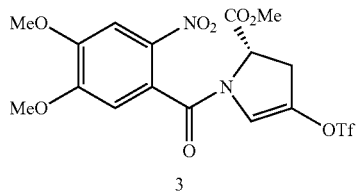

3

Anhydrous 2,6-lutidine (0.395 mL, 365 mg, 3.40 mmol) was injected in one portion to a vigorously stirred solution of ketone 2 (200 mg, 0.57 mmol) in dry DCM (10 mL) at −45° C. (dry ice/acetonitrile cooling bath) under a nitrogen atmosphere. Anhydrous triflic anhydride, taken from a freshly opened ampoule (477 µL, 800 mg, 2.83 mmol), was injected rapidly dropwise, while maintaining the temperature at −40° C. or below. The reaction mixture was allowed to stir at −45° C. for 1 hour at which point TLC (50/50 v/v n-hexane/EtOAc) revealed the complete consumption of starting material. The cold reaction mixture was immediately diluted with DCM (20 mL) and, with vigorous shaking, washed with water (1×50 mL), 5% citric acid solution (1×50 mL) saturated NaHCO₃ (50 mL), brine (30 mL) and dried (MgSO₄). Filtration and evaporation of the solvent in vacuo afforded the crude product which was purified by flash column chromatography (gradient elution: 60:40 v/v n-hexane/EtOAc to 50:50 v/v n-hexane/EtOAc) to afford the triflate 3 as a yellow foam (151 mg, 55%).

None of the corresponding 1,2 unsaturated compound was visible by NMR.

Analytical Data: $[\alpha]^{28}_D$=−55° (c=0.2, CHCl₃); ¹H NMR (400 MHz, CDCl₃) δ 7.75 (s, 1H), 6.92 (s, 1H), 6.25 (t, 1H, J=1.84 Hz), 5.19 (dd, 1H, J=5.05, 11.93 Hz), 4.03 (s, 6H), 3.90 (s, 3H), 3.50 (ddd, 1H, J=2.29, 11.96, 16.59 Hz), 3.02 (ddd, 1H, J=1.60, 5.05, 16.58 Hz); IR (ATR, CHCl₃) 1748, 1653, 1577, 1522, 1415, 1335, 1276, 1205, 1130, 1061, 1024, 933, 908, 820, 783, 757, 663, cm⁻¹; MS (ES⁺) m/z (relative intensity) 485.45 ([M+H]⁺˙, 100);

(c)

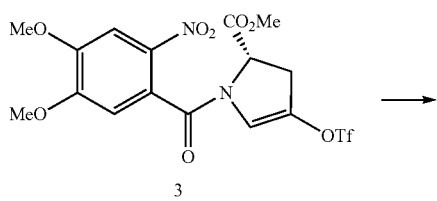

3

Pd(PPh₃)₄ (860 mg, 744 µmol, 0.04 eq) was added to a stirred mixture of enol triflate 3 (9.029 g, 18.6 mmol, 1 eq), 4-methoxyphenylboronic acid (3.67 g, 24.1 mmol, 1.3 eq), Na₂CO₃ (5.13 g, 48.3 mmol, 2.6 eq), EtOH (45 mL), toluene (90 mL) and water (45 mL). The reaction mixture was allowed to stir under a nitrogen atmosphere overnight after which time the complete consumption of starting material was observed by TLC (60/40 EtOAc/hexane) and LC/MS (3.10 min (ES+) m/z (relative intensity) 443.38 ([M+H]⁺˙, 100)). The reaction mixture was diluted with EtOAc (400 mL) and washed with H₂O (2×300 mL), brine (200 mL), dried (MgSO₄), filtered and evaporated under reduced pressure to provide the crude product. Purification by flash chromatography (gradient elution: 60:40 v/v hexane/EtOAc to 40:60 v/v hexane/EtOAc) afforded C2-aryl compound 4 as an orange solid (7.0 g, 85%).

Analytical Data: $[\alpha]^{25}_D$=−122° (c=0.2, CHCl₃); ¹H NMR (400 MHz, CDCl₃) δ 7.78 (s, 1H), 7.30 (d, 2H, J=8.81 Hz), 6.95 (s, 1H), 6.87 (s, 1H), 6.83 (d, 2H, J=8.88 Hz), 5.03 (dd, 1H, J=11.71, 5.28 Hz), 3.95 (s, 3H), 3.93 (s, 3H), 3.76 (s, 3H), 3.73 (s, 3H), 3.48-3.43 (m, 1H), 2.99-2.93 (m, 1H), ¹³C NMR (100 MHz, CDCl₃) δ 170.7, 162.5, 158.4, 153.9, 149.1, 137.9, 126.3, 125.6, 125.3, 122.9, 122.3, 113.8, 110.03, 107.6, 59.7, 57.9, 56.5, 56.2, 55.1, 54.9, 52.2, 33.9, 20.7, 14.0; IR (ATR, CHCl₃) 1736, 1624, 1575, 1516, 1424, 1326, 1253, 1178, 1069, 1031, 863, 820, 803, 786, 757, 653, 617 cm⁻¹; MS (ES⁺) m/z (relative intensity) 443.38 ([M+H]⁺˙, 100.

(d)

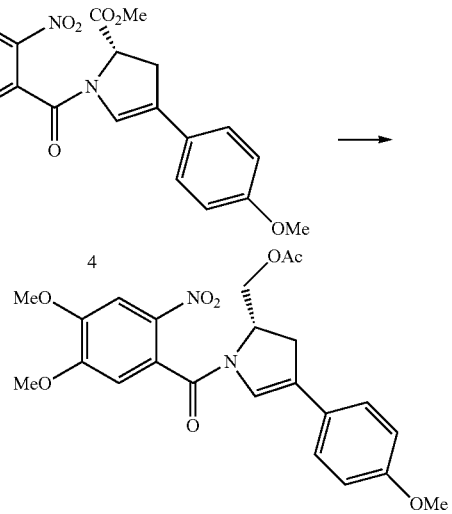

LiBH₄ (464 mg, 21.3 mmol, 1.5 eq) was added portionwise to a stirred solution of the ester 4 (6.28 g, 14.2 mmol, 1 eq) in anhydrous THF (100 mL) and EtOH (120 mL). An exotherm accompanied by vigorous foaming was observed and the temperature was maintained between 15° C. and 25° C. with the aid of a cooling bath (ice/water). The reaction mixture was allowed to stir for 1 h after which time the complete conversion of starting material directly was observed by TLC (ethyl acetate). The reaction mixture was carefully diluted with ethyl acetate (500 mL) and excess borohydride destroyed with cold aqueous citric acid. The organic layer was washed with 1N aqueous HCL (100 mL) followed by saturated aqueous NaHCO$_3$ (100 mL), brine (100 mL), dried over MgSO$_4$, filtered and evaporated under reduced pressure at 35° C. to provide the intermediate alcohol (4.50 g, 10.8 mmol, 76% intermediate yield) which was immediately redissolved in anhydrous DCM (200 mL). The solution was cooled to 0° C. and TEA (2.26 mL, 0.162 mmol, 1.5 eq) was added, followed by a solution of acetyl chloride (1 mL, 14.0 mmol, 1.3 eq) in anhydrous DCM (30 mL). The reaction mixture was allowed to warm up to room temperature and react for 1 hour. Completion was observed by TLC (EtOAc). The solution was washed with 2N aqueous citric acid (50 mL), saturated aqueous NaHCO$_3$ (50 mL), brine (50 mL), dried over MgSO$_4$, filtered and evaporated under reduced pressure. The residue was purified by flash chromatography (gradient from 50/50 up to 60/40 EtOAc/hexane) to yield 2.65 g (41% over two steps) of pure product 5 as an orange solid.

Analytical Data: $[\alpha]^{24}_D$=–130° (c=0.28, CHCl$_3$); $^1$H NMR (400 MHz, CDCl$_3$) δ 7.74 (s, 1H), 7.12 (d, 2H, J=8.84 Hz), 6.91 (br s, 1H), 6.80 (d, 2H, J=8.88 Hz), 6.15 (s, 1H), 5.04-5.00 (m, 1H), 4.61-4.42 (m, 2H), 4.01 (s, 6H), 3.78 (s, 3H), 3.35-3.25 (m, 1H), 2.85-2.79 (m, 1H), 2.06 (s, 3H). $^{13}$C NMR (100 MHz, CDCl$_3$) δ 171.1, 159.1, 149.5, 126.1, 126.0, 114.1, 107.2, 56.8, 56.6, 55.3, 33.5, 20.9; IR (ATR, CHCl$_3$) 1731, 1643, 1623, 1577, 1517, 1421, 1333, 1278, 1248, 1222, 1183, 1076, 1059, 1032, 864, 821, 802, 787, 756, 644, 619 cm$^{-1}$; MS (ES$^+$) m/z (relative intensity) 456.81 ([M+H]$^{+\cdot}$, 100.

(e)

vigorously stirred and heated to reflux. TLC monitoring (Ethyl Acetate) and LC/MS (2.97 min (ES+) m/z (relative intensity) 427.57 ([M+H]$^{+\cdot}$, 100)) revealed that the reaction was complete after 5 minutes. The reaction was allowed to cool, filtered through celite and washed with DCM (50 mL). The filtrate was washed with water (3×30 mL), saturated NaHCO$_3$ (2×30 mL), brine (30 mL), dried over MgSO$_4$, filtered and evaporated under reduced pressure. The residue was purified by flash chromatography (gradient from 60/40 up to 80/20 EtOAc/hexane) to yield 140 mg (88%) of pure product 6 as a white foam.

Analytical Data: $[\alpha]^{24}_D$=–108° (c=0.20, CHCl$_3$); $^1$H NMR (400 MHz, CDCl$_3$) δ 7.22 (d, 2H, J=8.80 Hz), 6.89 (br s, 1H), 6.86 (d, 2H, J=8.82 Hz), 6.80 (5, 1H), 6.29 (s, 1H), 5.02-4.96 (m, 1H), 4.50-4.40 (m, 4H), 3.89 (s, 3H), 3.82 (s, 3H), 3.81 (s, 1H), 3.30-3.25 (m, 1H), 2.85-2.79 (m, 1H), 2.06 (s, 3H). $^{13}$C NMR (100 MHz, CDCl$_3$) δ 194.6, 171.1, 171.0, 170.4, 164.0, 160.8, 155.1, 149.5, 146.2, 143.6, 130.5, 129.2, 125.8, 115.5, 114.1, 107.6, 105.4, 100.9, 63.5, 60.4, 56.9, 56.3, 37.4, 21.0, 20.6, 14.2; IR (ATR, CHCl$_3$) 1733, 1589, 1512, 1396, 1209, 1176, 1113, 1031, 823, 791, 762 cm$^{-1}$; MS (ES$^+$) m/z (relative intensity) 427.57 ([M+H]$^{+\cdot}$, 100).

(f)

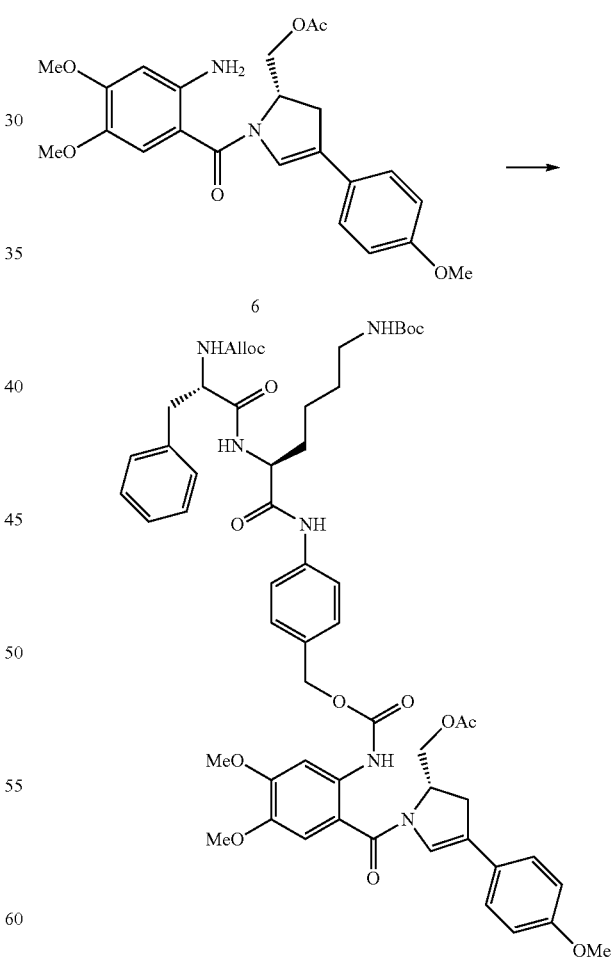

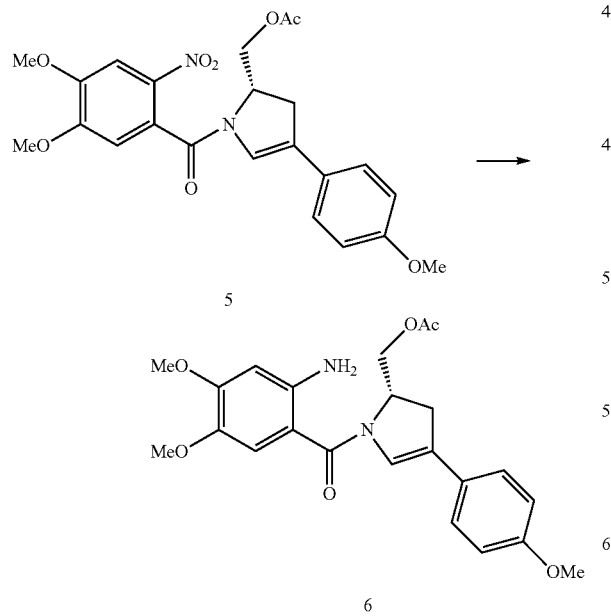

Zinc dust (365 mg, 5.58 mmol, 15 eq) was added to a solution of compound 5 (170 mg, 0.372 mmol, 1 eq) in ethanol (7.6 mL) and acetic acid (1.97 mL). The mixture was A solution of amine 6 (400 mg, 0.93 mmol, 1 eq) and TEA (350 µL, 2.5 mmol, 2.6 eq) in dry THF was added dropwise to a freshly prepared solution of triphosgene (125 mg, 0.42 mmol, 0.45 eq) in dry THF (4 mL) at 0° C. The white suspension was allowed to stir at 0° C. for 10 min. A solution of alcohol (Alloc-Phe-Lys(Boc)-PABOH, 546 mg, 0.93 mmol, 1 eq) and TEA (350 μL, 2.5 mmol, 2.6 eq) in dry THF (40 mL) was added rapidly. The white suspension was allowed to stir at room temperature for 15 min, then heated at 65° C. for 2 hours, then allowed to stir at room temperature overnight. The white TEA salts were removed by filtration over cotton wool. The filtrate was concentrated and purified by flash chromatography (Gradient, 1% MeOH in chloroform up to 3% MeOH in chloroform) to yield 700 mg of desired carbamate 7 (72%).

Analytical Data: $[\alpha]^{24}_D = -30.2°$ (c=0.18, CHCl$_3$); $^1$H NMR (400 MHz, CDCl$_3$) δ 8.54 (s, 1H), 8.43 (s, 1H), 7.74 (s, 1H), 7.45 (d, 2H, J=8.43 Hz), 7.23 (d, 2H, J=8.52 Hz), 7.16-7.06 (m, 7H), 6.78-6.72 (m, 4H), 6.46 (d, 1H, J=7.84 Hz), 5.82-5.73 (m, 1H), 5.30 (s, 1H), 5.19-5.06 (m, 2H), 5.03 (d, 1H, J=1.29 Hz), 4.93-4.87 (m, 1H), 4.63 (m, 1H), 4.47-4.28 (m, 6H), 3.87 (s, 3H), 3.76 (s, 3H), 3.72 (s, 1H), 3.16-3.09 (m, 1H), 3.07-2.95 (m, 4H), 2.72-2.67 (m, 1H), 1.95-1.83 (m, 1H), 1.60-1.51 (m, 1H), 1.43-1.39 (m, 2H), 1.35 (s, 9H), 1.28-1.19 (m, 2H). $^{13}$C NMR (100 MHz, CDCl$_3$) δ 171.5, 171.1, 169.2, 165.8, 159.1, 156.2, 153.8, 151.6, 144.1, 137.8, 135.8, 132.2, 131.9, 129.1, 129.0, 128.9, 127.3, 126.2, 125.9, 123.5, 123.4, 119.9, 118.2, 114.2, 111.3, 66.5, 66.2, 64.0, 56.5, 56.1, 55.3, 53.8, 33.1, 30.9, 29.4, 28.4, 22.6, 20.8; IR (ATR, CHCl$_3$) 1697, 1652, 1604, 1516, 1456, 1418, 1245, 1225, 1177, 1115, 1033, 824, 750 cm$^{-1}$; MS (ES$^+$) m/z (relative intensity) 1036.25 ([M+H]$^{+\cdot}$, 100).

(g)

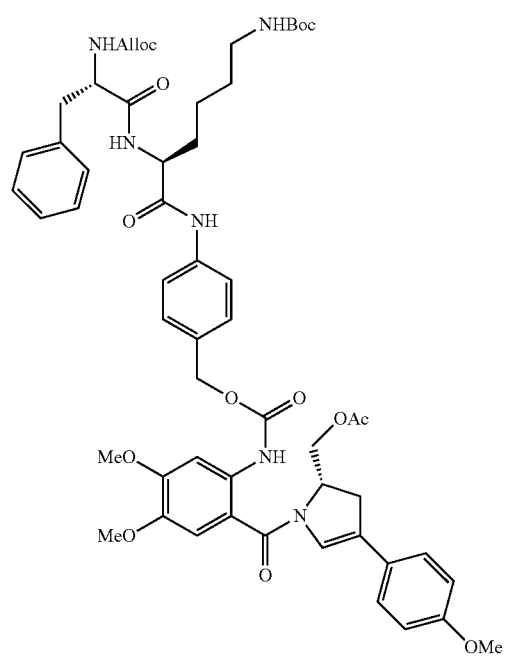

7

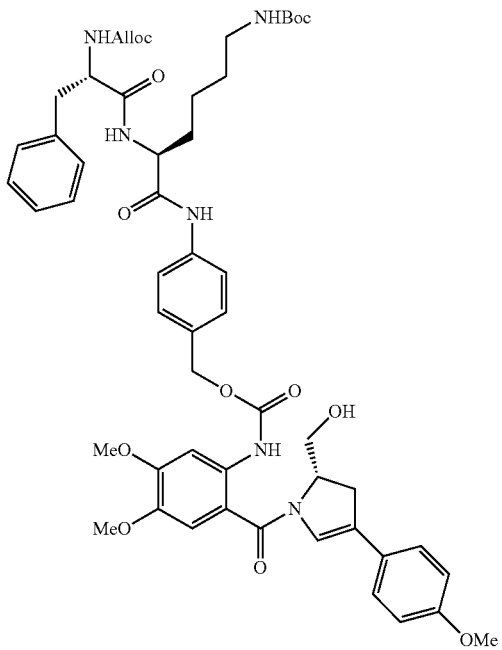

8

An aqueous solution (3.3 mL) of potassium carbonate (600 mg, 4.34 mmol, 5 eq) was added to a solution of acetate ester 7 (920 mg, 0.89 mmol, 1 eq) in methanol (20 mL). The reaction mixture was allowed to stir at room temperature for 50 min at which point TLC (chloroform/methanol, 90/10) showed completion.

The mixture was partitioned between water (150 mL) and dichloromethane (200 mL). The organic phase was washed with 1N citric acid 50 mL), followed by brine (50 mL) dried over MgSO$_4$, filtered and evaporated under reduced pressure to yield the desired alcohol 8 (700 mg, 79%).

Analytical Data: $[\alpha]^{24}_D = -61°$ (c=0.18, CHCl$_3$); $^1$H NMR (400 MHz, CDCl$_3$) δ 8.60 (s, 1H), 8.51 (s, 1H), 7.64 (s, 1H), 7.42 (d, 2H, J=8.38 Hz), 7.24-7.18 (m, 2H), 7.1-7.05 (m, 7H), 6.83-6.66 (m, 5H), 5.81-5.71 (m, 1H), 5.43 (s, 1H), 5.18-5.08 (m, 2H), 4.99 (s, 2H), 4.75-4.69 (m, 2H), 4.48-4.25 (m, 5H), 3.86 (s, 3H), 3.82-3.76 (m, 2H), 3.74 (s, 3H), 3.72 (s, 3H), 3.19-3.12 (m, 1H), 3.05-2.92 (m, 4H), 2.62-2.57 (m, 1H), 1.85-1.75 (m, 2H), 1.59-1.51 (m, 1H), 1.38-1.34 (m, 11H), 1.28-1.18 (m, 2H). $^{13}$C NMR (100 MHz, CDCl$_3$) δ 171.7, 169.5, 167.0, 159.2, 156.3, 153.9, 151.6, 144.4, 137.8, 135.9, 132.3, 131.9, 129.2, 128.8, 127.2, 126.0, 124.5, 123.3, 120.1, 118.1, 114.2, 111.3, 66.6, 66.1, 61.6, 56.5, 56.1, 55.3, 53.8, 39.9, 33.6, 31.1, 29.4, 28.4, 22.6; MS (ES$^+$) m/z (relative intensity) 994.7 ([M+H]$^{+\cdot}$, 100).

(h)

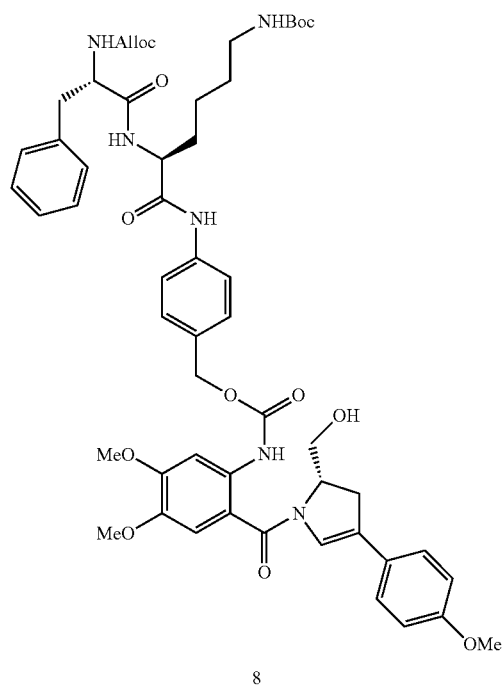

8

Alcohol 8 (500 mg, 0.503 mmol, 1 eq) was dissolved in anhydrous DCM (50 mL) at room temperature. Solid Dess-Martin Periodinane (300 mg, 0.707 mmol, 1.4 eq) was added, followed by 75 mg one hour later, 57 mg two hours later, and 31 mg 5 hours later taking the total mass of Dess-Martin Periodinane to 463 mg (1.09 mmol, 2.17 eq). The reaction was continuously monitored by TLC (chloroform/methanol, 95/5, two elutions). After 6.5 hours, the reaction appeared to be at an optimum and was worked up by partitioning the reaction mixture between DCM and saturated aqueous NaHSO$_3$. The organic layer was then washed with saturated aqueous NaHCO$_3$, followed by brine, dried over MgSO$_4$, filtered and evaporated under reduced pressure. The residue was purified by flash chromatography (gradient from 0/100 up to 2/98 methanol/chloroform) to yield 259 mg (52%) of pure product 9, Analytical Data: $[\alpha]^{24}_D$=+106° (c=0.16, CHCl$_3$); $^1$H NMR (400 MHz, CDCl$_3$) δ 8.68 (s, 1H), 7.54-7.46 (m, 2H), 7.36 (s, 1H), 7.31-7.16 (m, 8H), 6.89 (d, 2H, J=8.70 Hz), 6.75 (bs, 1H), 6.61 (s, 1H), 5.89-5.84 (m, 2H), 5.45 (d, 1H, J=4.80 Hz), 5.28-5.08 (m, 3H), 4.84-4.76 (m, 2H), 4.58-4.47 (m, 4H), 4.28 (bs, 1H), 4.02-3.95 (m, 1H), 3.92 (s, 3H), 3.83 (s, 3H), 3.74 (s, 2H), 3.41-3.32 (m, 1H), 3.16-3.02 (m, 5H), 2.03-1.83 (m, 1H), 1.68-1.61 (m, 1H), 1.55-1.39 (m, 11H), 1.36-1.28 (m, 2H). $^{13}$C NMR (100 MHz, CDCl$_3$) δ 171.7, 169.5, 163.2, 159.1, 156.3, 151.1, 148.6, 138.0, 135.9, 132.3, 129.2, 128.8, 127.2, 126.3, 126.2, 121.7, 120.0, 118.2, 114.2, 112.7, 110.7, 86.2, 79.3, 67.6, 66.2, 59.5, 56.4, 56.15, 56.1, 55.3, 53.8, 39.9, 38.1, 35.1, 31.0, 29.4, 28.4, 22.7; IR (ATR, CHCl$_3$) 3313, 2935, 2356, 1691, 1603, 1512, 1431, 1253, 1177, 1119, 1033, 824, 750, 698 cm$^{-1}$; MS (ES$^+$) m/z (relative intensity) 992.41 ([M+H]$^+$, 100).

(i)

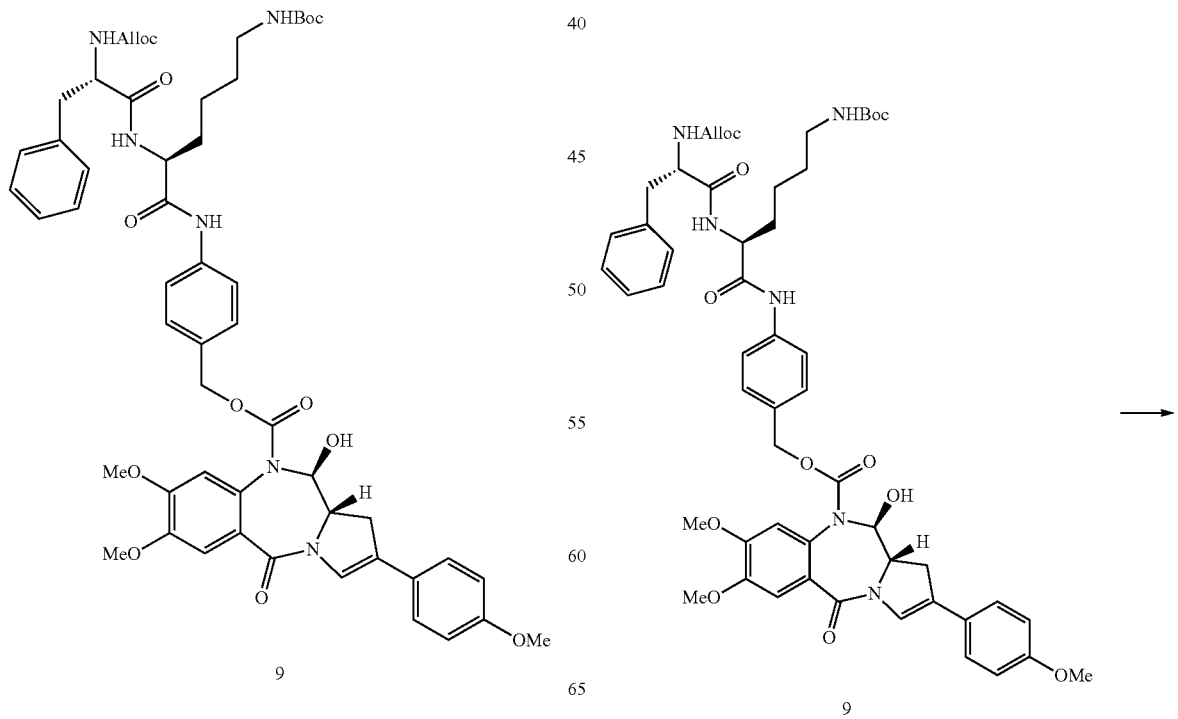

9

9

(j)

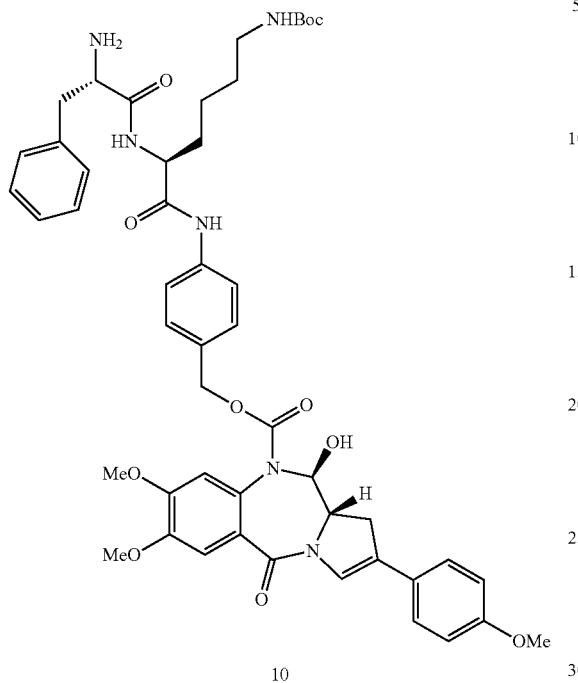

10

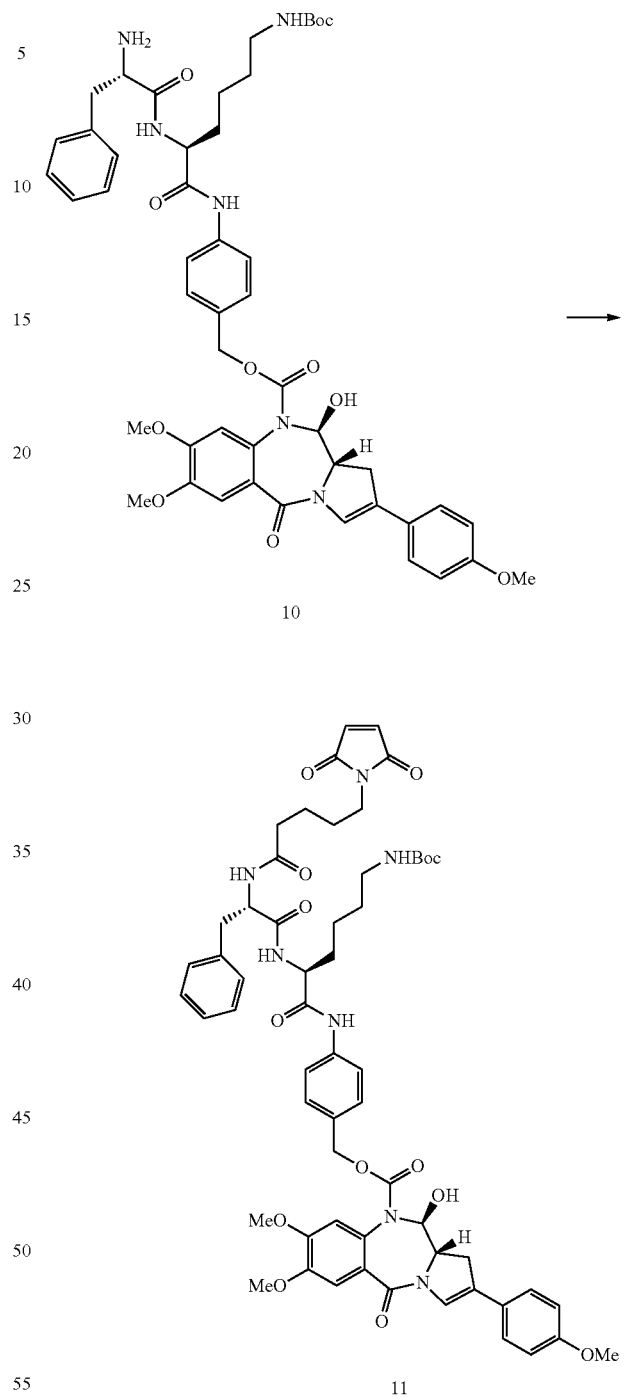

Solid Pd(PPh$_3$)$_4$ (8 mg, 6.9 μmol, 0.02 eq) was added to a freshly prepared solution of starting material 9 (346 mg, 0.349 mmol, 1 eq) and pyrrolidine (43.3 μL, 0.523 mmol, 1.5 eq) in dry DCM (10 mL) under inert atmosphere at room temperature. The reaction was complete after 45 min as proved by TLC (90/10 v/v chloroform/methanol,) and LC/MS (2.93 min (ES$^+$) m/z (relative intensity) 908.09 ([M+H]$^{+\cdot}$, 100)). The volatiles were removed by evaporation under reduced pressure. The residue was purified by flash chromatography (gradient from 2/98 up to 5/95 methanol/chloroform) to yield 298 mg (94%) of pure product 10.

Analytical Data: $^1$H NMR (400 MHz, CDCl$_3$) δ 8.87 (s, 1H), 7.86 (d, 1H, J=8.06 Hz), 7.51 (d, 2H, J=8.42 Hz), 7.36-7.11 (m, 9H), 6.89 (d, 2H, J=8.73 Hz), 6.58 (bs, 1H), 5.85 (d, 1H, J=9.47 Hz), 5.32 (m, 1H), 4.83 (d, 1H, J=11.68 Hz), 4.65 (m, 1H), 4.47 (q, 1H, J=6.14 Hz), 4.03-3.97 (m, 1H), 3.94 (s, 3H), 3.84 (s, 3H), 3.74-3.69 (m, 4H), 3.39-3.33 (m, 1H), 3.26 (dd, 1H, J=13.73 Hz, J=4.00 Hz), 3.16-3.03 (m, 3H), 3.26 (dd, 1H, J=8.91 Hz, J=13.74 Hz), 2.05-1.96 (m, 1H), 1.78-1.49 (m, 3H), 1.48-1.42 (m, 9H), 1.42-1.24 (m, 2H). $^{13}$C NMR (100 MHz, CDCl$_3$) δ 175.45, 163.2, 159.1, 156.2, 148.6, 137.3, 129.3, 128.8, 127.0, 126.2, 126.2, 121.7, 119.8, 114.2, 112.6, 56.2, 55.3, 40.7, 35.1, 30.5, 28.4, 22.8; MS (ES$^+$) m/z (relative intensity) 908.09 ([M+H]$^{+\cdot}$, 100).

Solid EEDQ (108 mg, 0.436 mmol, 2 eq) was added to a solution of amine 10 (199 mg, 0.219 mmol, 1 eq) and maleimido hexanoic acid (57 mg, 0.269, 1.23 eq) in a mixture of DCM (6 mL) and methanol (3 mL). The solution was allowed to stir at room temperature for 24 hours. The reaction was found complete by LC/MS (3.45 min (ES+) m/z (relative intensity) 1101.78 ([M+H]$^{+\cdot}$, 100)). The volatiles were removed by evaporation under reduced pressure. The residue was partitioned between DCM and saturated aqueous NaHCO₃, washed with brine, dried over MgSO₄, filtered and evaporated under reduced pressure. The residue was purified by flash chromatography (gradient from 1/99 up to 2.5/97.5 methanol/chloroform) to yield 165 mg (68%) of pure product 11.

Analytical Data: [α]²⁴_D=+94° (c=0.09, CHCl₃); ¹H NMR (400 MHz, CDCl₃) δ 8.62 (s, 1H), 7.46-7.39 (m, 2H), 7.27 (s, 1H), 7.22-7.06 (m, 9H), 6.79 (d, 2H, J=8.65 Hz), 6.75 (bs, 1H), 6.57 (s, 2H), 6.52 (s, 1H), 6.28 (s, 1H), 5.77 (bs, 1H), 5.21 (s, 1H), 4.75-4.60 (m, 2H), 4.40 (q, 1H, J=5.54 Hz), 3.93-3.86 (m, 1H), 3.83 (s, 3H), 3.73 (s, 3H), 3.65 (s, 2H), 3.36 (t, 2H, J=7.16 Hz), 3.30-3.23 (m, 1H), 3.08-2.90 (m, 5H), 2.09 (t, 2H, J=7.14 Hz), 1.93-1.75 (m, 1H), 1.62-1.31 (m, 17H), 1.30-1.04 (m, 6H). ¹³C NMR (100 MHz, CDCl₃) δ 173.5, 170.9, 170.3, 169.6, 163.2, 159.1, 156.3, 151.1, 148.6, 136.1, 134.0, 129.1, 128.7, 127.2, 126.3, 126.2, 124.9, 123.3, 121.7, 120.0, 114.2, 112.7, 110.7, 86.1, 79.3, 67.6, 59.5, 56.2, 56.1, 55.3, 54.6, 53.9, 53.4, 37.8, 37.5, 36.7, 35.2, 31.0, 29.4, 28.5, 28.2, 26.2, 24.8, 22.7; MS (ES⁺) m/z (relative intensity) 1101.78 ([M+H]⁺·, 100).

(k)

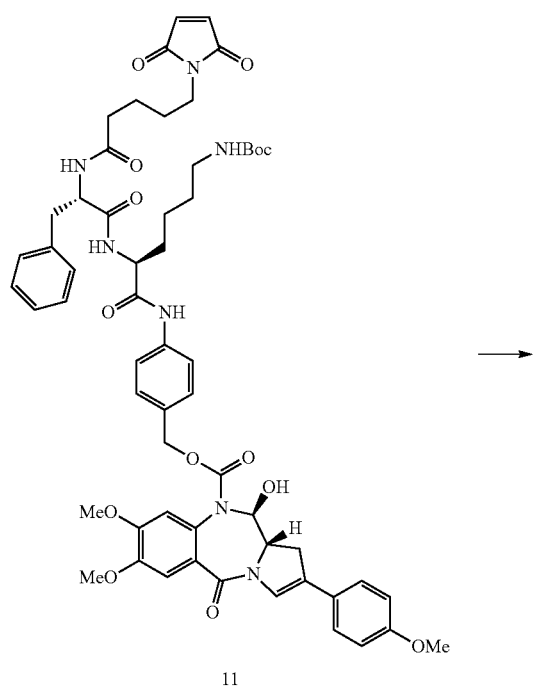

11

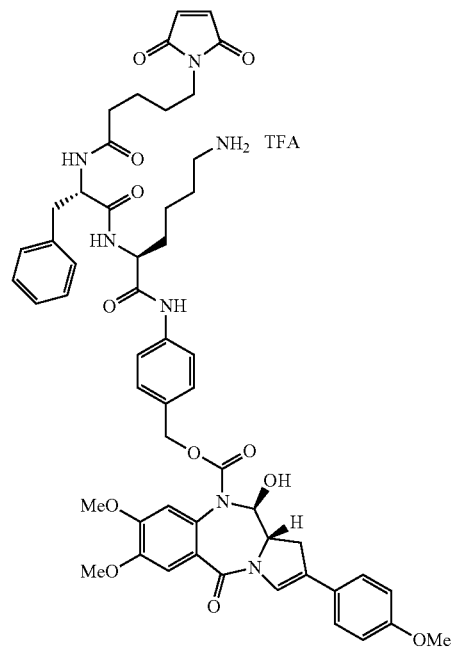

12

A chilled solution of 10% TFA in DCM (12 mL) was added to a chilled (−20° C.) sample of the Boc protected starting material 11 (75 mg, 0.068 mmol, 1 eq). The reaction was closely monitored by LC/MS (2.87 min (ES+) m/z (relative intensity) 1001.13 ([M+H]⁺·, 100)). The reaction reached completion after 4 hours. The reaction mixture was poured into deionised water (50 mL) and freeze-dried overnight (liquid nitrogen bath, allowed to evaporate without refill) to yield the pure TFA salt 12 (75 mg, 99%).

Analytical Data: ¹H NMR (400 MHz, CDCl₃) δ 9.05 (s, 1H), 7.87-7.62 (m, 4H), 7.35 (m, 2H), 7.24 (s, 1H), 7.16-7.11 (m, 2H), 7.10-6.96 (m, 8H), 6.92 (s, 1H), 6.82-6.66 (m, 3H), 6.63-6.42 (m, 3H), 5.75 (d, 1H, J=9.54 Hz), 5.15-5.03 (m, 1H), 4.77-4.74 (m, 1H), 4.68-4.56 (m, 1H), 4.39 (s, 1H), 3.97-3.84 (m, 1H), 3.80 (s, 3H), 3.72 (s, 3H), 3.65 (s, 2H), 3.33-3.21 (m, 3H), 3.04-2.69 (m, 5H), 2.04 (m, 2H), 1.979-1.64 (m, 1H), 1.63-1.45 (m, 3H), 1.44-1.12 (m, 6H), 1.07-0.95 (m, 2H). MS (ES⁺) m/z (relative intensity) 1001.13 ([M+H]⁺·, 100).

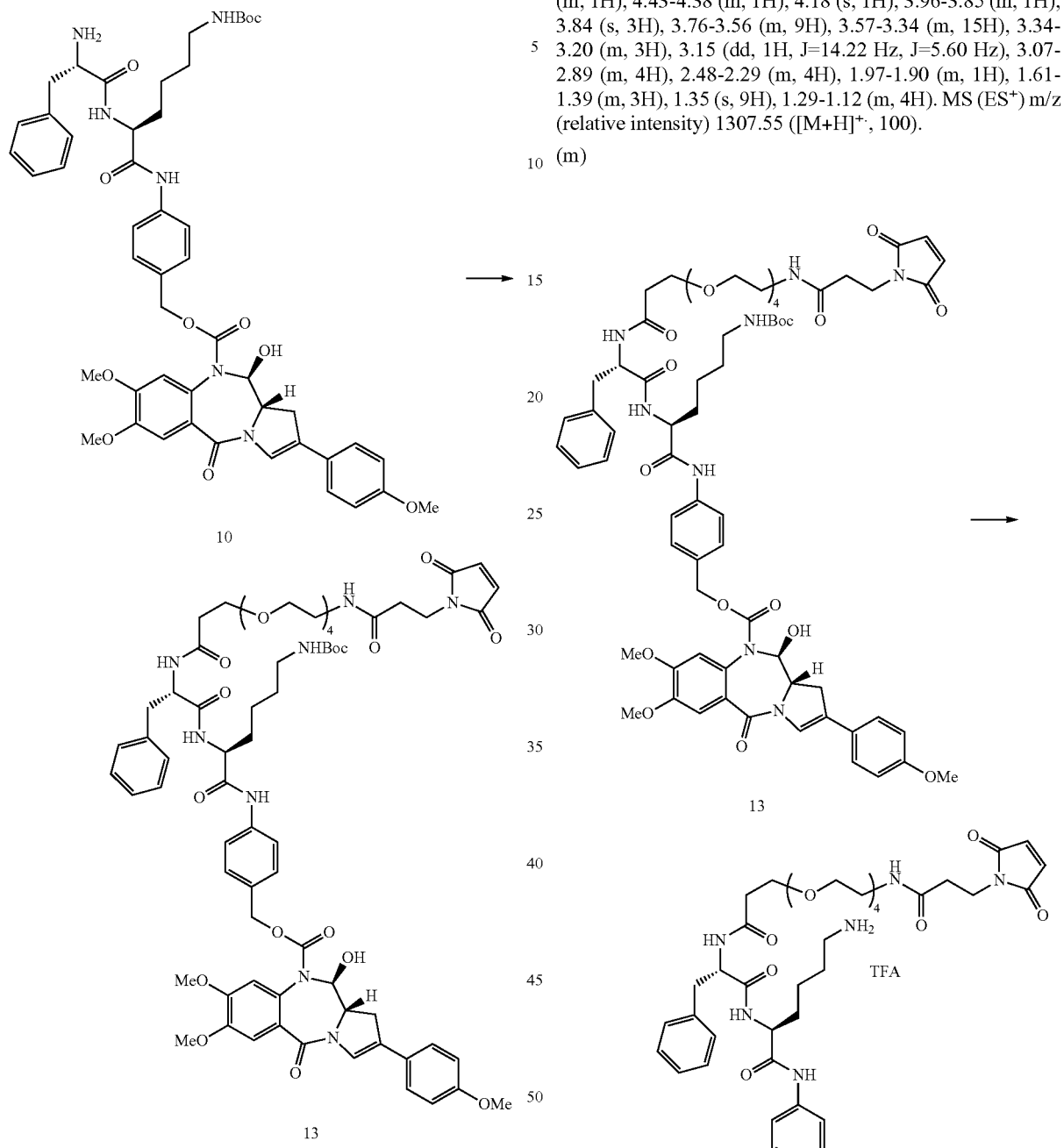

J=8.68 Hz), 6.59 (s, 2H), 6.51 (s, 1H), 5.77 (d, 1H, J=6.42 Hz), 5.25 (d, 1H, J=11.43 Hz), 4.83-4.64 (m, 2H), 4.63-4.49 (m, 1H), 4.43-4.38 (m, 1H), 4.18 (s, 1H), 3.96-3.85 (m, 1H), 3.84 (s, 3H), 3.76-3.56 (m, 9H), 3.57-3.34 (m, 15H), 3.34-3.20 (m, 3H), 3.15 (dd, 1H, J=14.22 Hz, J=5.60 Hz), 3.07-2.89 (m, 4H), 2.48-2.29 (m, 4H), 1.97-1.90 (m, 1H), 1.61-1.39 (m, 3H), 1.35 (s, 9H), 1.29-1.12 (m, 4H). MS (ES$^+$) m/z (relative intensity) 1307.55 ([M+H]$^{+\cdot}$, 100).

(m)

Amine 10 (99 mg, 0.109 mmol, 1 eq) was added to a solution of NHS-PEG$_4$-Maleimide (Thermo Scientific, 61.6 mg, 0.120 mmol, 1.1 eq) and TEA (18.2 μL, 0.130 mmol, 1.2 eq) in a mixture of anhydrous DCM (5 mL) and DMF (1 mL). The reaction was allowed to stir at room temperature overnight at which point it was found to be almost complete by LC/MS (3.27 min (ES+) m/z (relative intensity) 1307.55 ([M+H]$^{+\cdot}$, 100)). The volatiles were removed by evaporation under reduced pressure. The residue was purified by flash chromatography (gradient from 3/97 up to 5/95 methanol/chloroform) to yield 71 mg (50%) of pure product 13.

Analytical Data: $^1$H NMR (400 MHz, CDCl$_3$) δ 8.58 (s, 1H), 7.50 (d, 2H, J=8.47 Hz), 7.28 (s, 1H), 7.25-7.20 (m, 2H), 7.18-7.01 (m, 9H), 6.89 (d, 1H, J=7.58 Hz), 6.79 (d, 2H, A chilled solution of 10% TFA in DCM (10 mL) was added to a chilled (−20° C.) sample of the Boc protected starting material 13 (70 mg, 0.054 mmol, 1 eq). The reaction was closely monitored by LC/MS (2.77 min (ES+) m/z (relative intensity) 1206.94 ([M+H]$^{+\cdot}$, 100)). The reaction reached completion after 18 hours at −25° C. The reaction mixture was poured into deionised water (50 mL) and freeze-dried overnight (liquid nitrogen bath, allowed to evaporate without refill) to yield the pure TFA salt 14 (75 mg, 99%).

Example 2

(a)

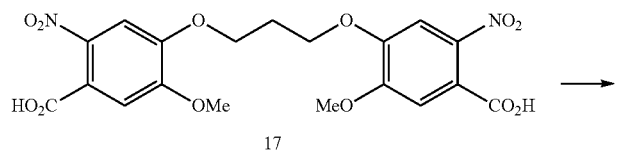

17

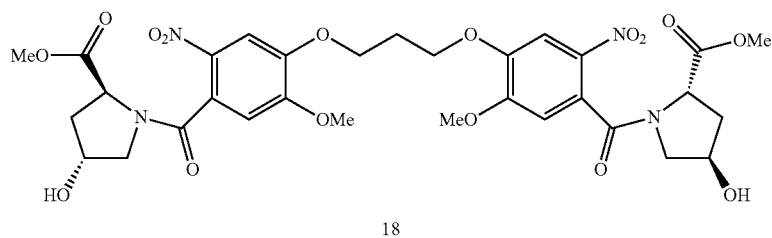

18

Compound 17 and its synthesis is disclosed in WO 00/012508 and WO 2006/111759. Method I: A catalytic amount of DMF (2 drops) was added (effervescence!) to a stirred solution of the nitro-acid 17 (1.0 g, 2.15 mmol) and oxalyl chloride (0.95 mL, 1.36 g, 10.7 mmol) in dry THF (20 mL). The reaction mixture was allowed to stir for 16 hours at room temperature and the solvent was removed by evaporation in vacuo. The resulting residue was re-dissolved in dry THF (20 mL) and the acid chloride solution was added dropwise to a stirred mixture of (2S,4R)-methyl-4-hydroxypyrrolidine-2-carboxylate hydrochloride (859 mg, 4.73 mmol) and TEA (6.6 mL, 4.79 g, 47.3 mmol) in THF (10 mL) at −30° C. (dry ice/ethylene glycol) under a nitrogen atmosphere. The reaction mixture was allowed to warm to room temperature and stirred for a further 3 hours after which time TLC (95:5 v/v CHCl$_3$/MeOH) and LC/MS (2.45 min (ES$^+$) m/z (relative intensity) 721 ([M+H]$^{+\cdot}$, 20)) revealed formation of product. Excess THF was removed by rotary evaporation and the resulting residue was dissolved in DCM (50 mL). The organic layer was washed with 1N HCl (2×15 mL), saturated NaHCO$_3$ (2×15 mL), H$_2$O (20 mL), brine (30 mL) and dried (MgSO$_4$). Filtration and evaporation of the solvent gave the crude product as a dark coloured oil. Purification by flash chromatography (gradient elution: 100% CHCl$_3$ to 96:4 v/v CHCl$_3$/MeOH) isolated the pure amide 18 as an orange coloured glass (840 mg, 54%).

Method II: Oxalyl chloride (9.75 mL, 14.2 g, 111 mmol) was added to a stirred suspension of the nitro-acid 17 (17.3 g, 37.1 mmol) and DMF (2 mL) in anhydrous DCM (200 mL). Following initial effervescence the reaction suspension became a solution and the mixture was allowed to stir at room temperature for 16 hours. Conversion to the acid chloride was confirmed by treating a sample of the reaction mixture with MeOH and the resulting bis-methyl ester was observed by LC/MS. The majority of solvent was removed by evaporation in vacuo, the resulting concentrated solution was re-dissolved in a minimum amount of dry DCM and triturated with diethyl ether. The resulting yellow precipitate was collected by filtration, washed with cold diethyl ether and dried for 1 hour in a vacuum oven at 40° C. The solid acid chloride was added portionwise over a period of 25 minutes to a stirred suspension of (2S,4R)-methyl-4-hydroxypyrrolidine-2-carboxylate hydrochloride (15.2 g, 84.0 mmol) and TEA (25.7 mL, 18.7 g, 185 mmol) in DCM (150 mL) at −40° C. (dry ice/CH$_3$CN). Immediately, the reaction was complete as judged by LC/MS (2.47 min (ES+) m/z (relative intensity) 721 ([M+H]$^{+\cdot}$, 100)). The mixture was diluted with DCM (150 mL) and washed with 1N HCl (300 mL), saturated NaHCO$_3$ (300 mL), brine (300 mL), filtered (through a phase separator) and the solvent evaporated in vacuo to give the pure product 18 as an orange solid (21.8 g, 82%).

Analytical Data: $[\alpha]^{22}{}_D$=−46.1° (c=0.47, CHCl$_3$); $^1$H NMR (400 MHz, CDCl$_3$) (rotamers) δ 7.63 (s, 2H), 6.82 (s, 2H), 4.79-4.72 (m, 2H), 4.49-4.28 (m, 6H), 3.96 (s, 6H), 3.79 (s, 6H), 3.46-3.38 (m, 2H), 3.02 (d, 2H, J=11.1 Hz), 2.48-2.30 (m, 4H), 2.29-2.04 (m, 4H); $^{13}$C NMR (100 MHz, CDCl$_3$) (rotamers) δ 172.4, 166.7, 154.6, 148.4, 137.2, 127.0, 109.7, 108.2, 69.7, 65.1, 57.4, 57.0, 56.7, 52.4, 37.8, 29.0; IR (ATR, CHCl$_3$) 3410 (br), 3010, 2953, 1741, 1622, 1577, 1519, 1455, 1429, 1334, 1274, 1211, 1177, 1072, 1050, 1008, 871 cm$^{-1}$; MS (ES$^+$) m/z (relative intensity) 721 ([M+H]$^{+\cdot}$, 47), 388 (80); HRMS [M+H]$^{+\cdot}$ theoretical C$_{31}$H$_{36}$N$_4$O$_{16}$ m/z 721.2199, found (ES$^+$) m/z 721.2227.

(b)

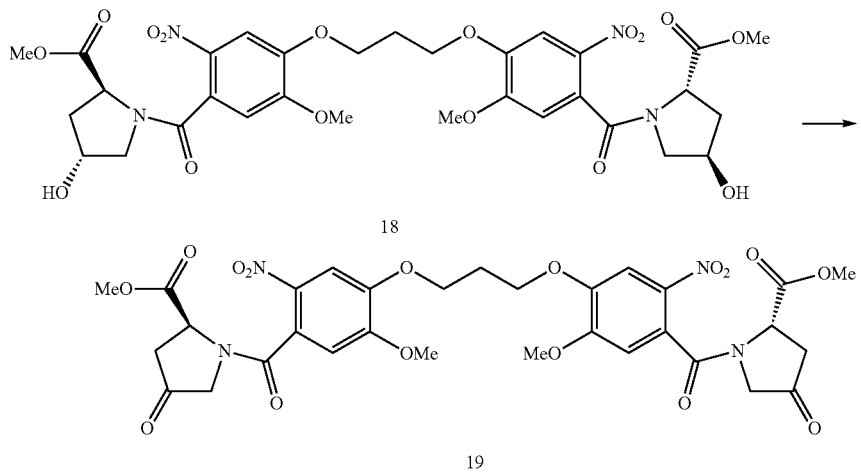

Solid TCCA (32 g, 137 mmol, 2.2 eq) was added portion-wise to a solution of TEMPO (1 g, 6.4 mmol, 0.1 eq) and bis-alcohol 18 (45 g, 62.5 mmol, 1 eq), in normal DCM (500 mL) at 0° C. A slight exotherm was observed. The reaction was deemed complete by TLC (Ethyl Acetate) and LC/MS (2.95 min (ES+) m/z (relative intensity) 718.10 ([M+H]$^{+\cdot}$, 100)) after 30 minutes. The suspension was filtered through celite and washed with DCM. The filtrate was washed with aqueous sodium bisulfite, followed by saturated NaHCO$_3$ (caution, vigorous effervescence), brine (200 mL) and dried (MgSO$_4$). Filtration and evaporation of the solvent in vacuo afforded the crude product which was purified by flash column chromatography (elution: 20:80 v/v n-hexane/EtOAc) to afford the ketone 19 as a white solid (28.23 g, 63%).

Analytical Data: $[\alpha]^{21}{}_D$=+18° (c=0.2, CHCl$_3$); MS (ES$^+$) m/z (relative intensity) 718.10 ([M+H]$^{+\cdot}$, 100); $^1$H NMR (400 MHz, CDCl$_3$) mixture of rotamers δ 7.70 (m, 2H), 6.79 (m, 2H), 5.27 (m, 1H), 4.44 (m, 1H), 4.30 (m, 4H), 3.93 (m, 6H), 3.81 (s, 3H), 3.75 (m, 1H), 3.63 (s, 2H), 3.58 (m, 1H), 3.09-2.89 (m, 2H), 2.74-2.53 (m, 2H), 2.40 (p, 2H, J=5.73 Hz); $^{13}$C NMR (100 MHz, CDCl$_3$) mixture of rotamers δ 206.5, 206.4, 206.0, 205.9, 171.2, 171.1, 170.6, 167.0, 166.7, 155.0, 154.5, 148.8, 137.7, 137.3, 126.4, 125.4, 109.8, 109.1, 108.6, 108.4, 108.4, 65.7, 65.6, 65.5, 60.4, 57.9, 56.7, 56.7, 55.1, 53.6, 52.9, 52.9, 51.6, 41.2, 40.1, 28.7, 28.6, 21.0, 14.1; IR (ATR, CHCl$_3$) 1764, 1650, 1578, 1518, 1415, 1333, 1274, 1217, 1060, 870, 824 759 cm$^{-1}$ (c)

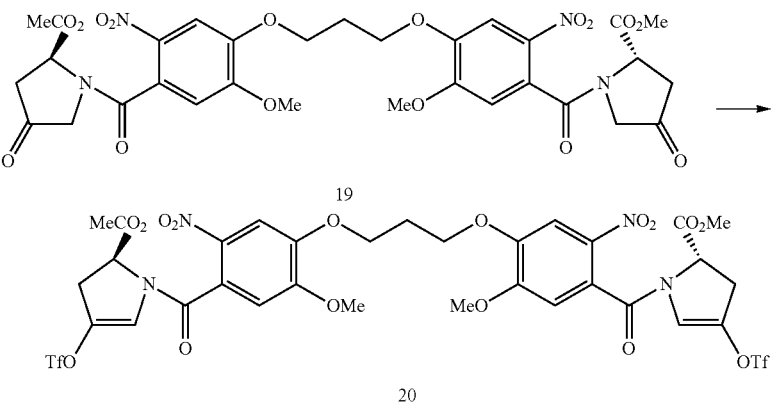

Anhydrous 2,6-lutidine (4.26 mL, 3.92 g, 36.6 mmol) was injected in one portion to a vigorously stirred solution of bis-ketone 19 (4.23 g, 5.90 mmol) in dry DCM (100 mL) at −45° C. (dry ice/acetonitrile cooling bath) under a nitrogen atmosphere. Anhydrous triflic anhydride, taken from a freshly opened ampoule (5.96 mL, 10 g, 35.4 mmol), was injected rapidly dropwise, while maintaining the temperature at −40° C. or below. The reaction mixture was allowed to stir at −45° C. for 1 hour at which point TLC (50/50 v/v n-hexane/EtOAc) revealed the complete consumption of starting material. The cold reaction mixture was immediately diluted with DCM (200 mL) and, with vigorous shaking, washed with water (1×300 mL), 5% citric acid solution (1×200 mL) saturated NaHCO$_3$ (200 mL), brine (150 mL) and dried (MgSO$_4$). Filtration and evaporation of the solvent in vacuo afforded the crude product which was purified by flash column chromatography (gradient elution: 70:30 v/v n-hexane/EtOAc to 40:60 v/v n-hexane/EtOAc) to afford the bis-triflate 20 as a yellow foam (1.32 g, 23%).

None of the corresponding 1,2 unsaturated compound was visible by NMR.

Analytical Data: $[\alpha]^{25}_D$=−68° (c=0.2, CHCl$_3$); $^1$H NMR (400 MHz, CDCl$_3$) δ 7.73 (s, 2H), 6.85 (s, 2H), 6.20 (t, 2H, J=1.81 Hz), 5.13 (dd, 2H, J=5.05, 11.93 Hz), 4.33 (t, 4H, J=5.91 Hz), 3.95 (s, 6H), 3.84 (s, 6H), 3.43 (ddd, 2H, J=2.28, 11.92, 16.59 Hz), 2.96 (ddd, 2H, J=1.60, 5.05, 16.58 Hz), 2.44 (p, 2H, J=5.79 Hz); $^{13}$C NMR (100 MHz, CDCl$_3$) δ 169.4, 164.1, 154.7, 149.2, 138.0, 135.2, 124.4, 121.1, 120.0, 116.8, 110.0, 108.4, 65.7, 65.6, 57.0, 56.8, 53.1, 33.3, 28.6; IR (ATR, CHCl$_3$) 1749, 1654, 1576, 1522, 1418, 1337, 1277, 1207, 1131, 1061, 1023, 910, 821, 757 cm$^{-1}$; MS (ES$^+$) m/z (relative intensity) 981.86 ([M+H]$^{+\cdot}$, 100).

(d)

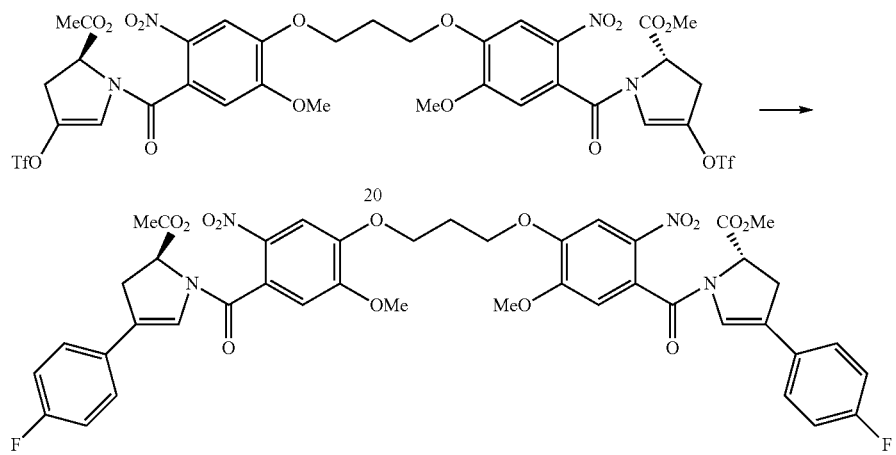

Pd(PPh$_3$)$_4$ (660 mg, 571 μmol, 0.08 eq) was added to a stirred mixture of bis enol triflate 20 (7 g, 7.13 mmol, 1 eq), 4-fluorophenylboronic acid (2.6 g, 18.5 mmol, 2.6 eq), Na$_2$CO$_3$ (3.93 g, 37.0 mmol, 5.2 eq), EtOH (25 mL), toluene (50 mL) and water (25 mL). The reaction mixture was allowed to stir under a nitrogen atmosphere overnight after which time the complete consumption of starting material was observed by TLC (60/40 EtOAc/hexane) and LC/MS (3.68 min (ES+) m/z (relative intensity) 873.90 ([M+H]$^+$, 100)). The reaction mixture was diluted with EtOAc (300 mL) and washed with H$_2$O (2×200 mL), brine (100 mL), dried (MgSO$_4$), filtered and evaporated under reduced pressure to provide the crude product. Purification by flash chromatography (gradient elution: 50:50 v/v hexane/EtOAc to 80:20 v/v hexane/EtOAc) afforded bis C2-aryl compound 21 as an orange solid (5.46 g, 88%).

Analytical Data: $[\alpha]^{22}_D$=−107° (c=0.2, CHCl$_3$); $^1$H NMR (400 MHz, CDCl$_3$) δ 7.76 (s, 2H), 7.14-7.04 (m, 4H), 6.97-6.87 (m, 6H), 6.31 (s, 2H), 5.18 (dd, 2H, J=11.68, 5.03 Hz), 4.36 (t, 4H, J=5.87 Hz), 3.97 (s, 6H), 3.84 (s, 6H), 3.53-3.39 (m, 2H), 3.00 (ddd, 2H, J=1.22, 5.01, 16.28 Hz), 2.46 (p, 2H, J=5.98 Hz); $^{13}$C NMR (100 MHz, CDCl$_3$) δ171.0, 163.3, 148.9, 138.0, 128.1, 126.3, 126.2, 125.8, 123.1, 122.6, 115.7, 115.5, 110.3, 108.5, 65.7, 58.3, 56.8, 34.7, 28.7; IR (ATR, CHCl$_3$) 1738, 1650, 1578, 1512, 1416, 1333, 1275, 1212, 1064, 1023, 869, 808, 758, 654, 613 cm$^{-1}$; MS (ES$^+$) m/z (relative intensity) 873.90 ([M+H]$^{+\cdot}$, 100)).

(e)

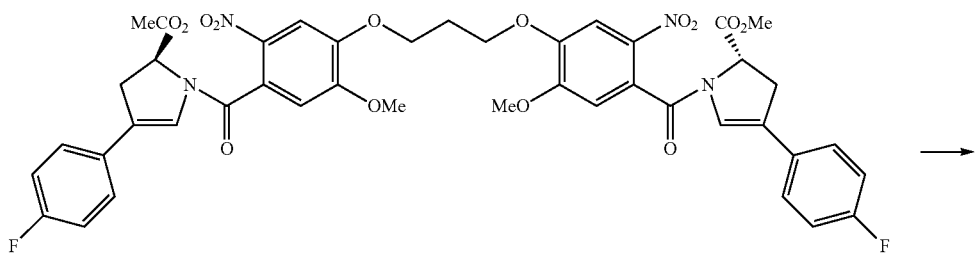

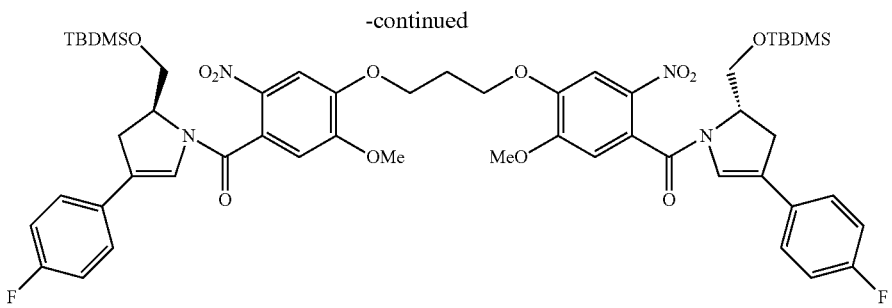

22

LiBH$_4$ (132 mg, 21.3 mmol, 3 eq) was added in one portion to a stirred solution of the ester 21 (5.30 g, 6.07 mmol, 1 eq) in anhydrous THF (100 mL) at 0° C. The reaction mixture was allowed to warm up to room temperature and to stir for 1 hour after which time the complete conversion of starting material was observed by LC/MS (3.42 min (ES+) m/z (relative intensity) 818.35 ([M+H]$^{+\cdot}$, 100)). The reaction mixture was carefully diluted with ethyl acetate (500 mL) and excess borohydride destroyed with cold aqueous citric acid. The organic layer was washed with 1N aqueous HCL (100 mL) followed by saturated aqueous NaHCO$_3$ (100 mL), brine (100 mL), dried over MgSO$_4$, filtered and evaporated under reduced pressure at 35° C. to provide the intermediate alcohol which was immediately redissolved in anhydrous DCM (200 mL). The solution was cooled to 0° C. and imidazole (3.97 g, 58.0 mmol, 9.6 eq) was added, followed by TBDMS-CI (4.390 g, 29.1 mmol, 4.8 eq). The reaction mixture was allowed to warm up to room temperature and react for 2 hours. Complete reaction was observed by TLC (EtOAc/hexane, 50/50) and LC/MS (4.23 min (ES+) m/z (relative intensity) 1045.99 ([M+H]$^{+\cdot}$, 100)). The solution was washed with 2N aqueous citric acid (50 mL), saturated aqueous NaHCO$_3$ (50 mL), brine (50 mL), dried over MgSO$_4$, filtered and evaporated under reduced pressure. The residue was purified by flash chromatography (gradient from 80/20 up to 60/40 hexane/EtOAc) to yield 2.45 g (38.6% over two steps) of pure product 22 as an orange solid.

Analytical Data: [α]$^{22}_D$=−123° (c=0.18, CHCl$_3$); $^1$H NMR (400 MHz, CDCl$_3$) δ 7.76 (s, 2H), 7.17-7.06 (m, 4H), 6.96-6.87 (m, 4H), 6.81 (s, 2H), 6.17 (s, 2H), 4.84-4.72 (m, 2H), 4.35 (t, 4H, J=5.87 Hz), 3.93 (s, 6H), 3.25-3.07 (m, 2H), 3.03-2.91 (m, 2H) 2.45 (p, 2H, J=5.92 Hz), 0.84 (s, 18H), 0.07 (s, 12H); $^{13}$C NMR (100 MHz, CDCl$_3$) δ 163.2, 160.7, 154.5, 148.6, 137.9, 130.1, 130.0, 126.7, 126.3, 126.2, 124.3, 123.0, 115.6, 115.4, 110.0, 108.5, 65.7, 60.4, 59.2, 56.7, 33.2, 28.7, 25.8, 25.7, 21.0, 18.2, 14.2, −5.3; IR (ATR, CHCl$_3$) 2953, 1742, 1650, 1576, 1512, 1417, 1334, 1274, 1214, 1063, 1023, 869, 808, 759, 654, 612 cm$^{-1}$; MS (ES$^+$) m/z (relative intensity) 1045.99 ([M+H]$^{+\cdot}$, 100).

(f)

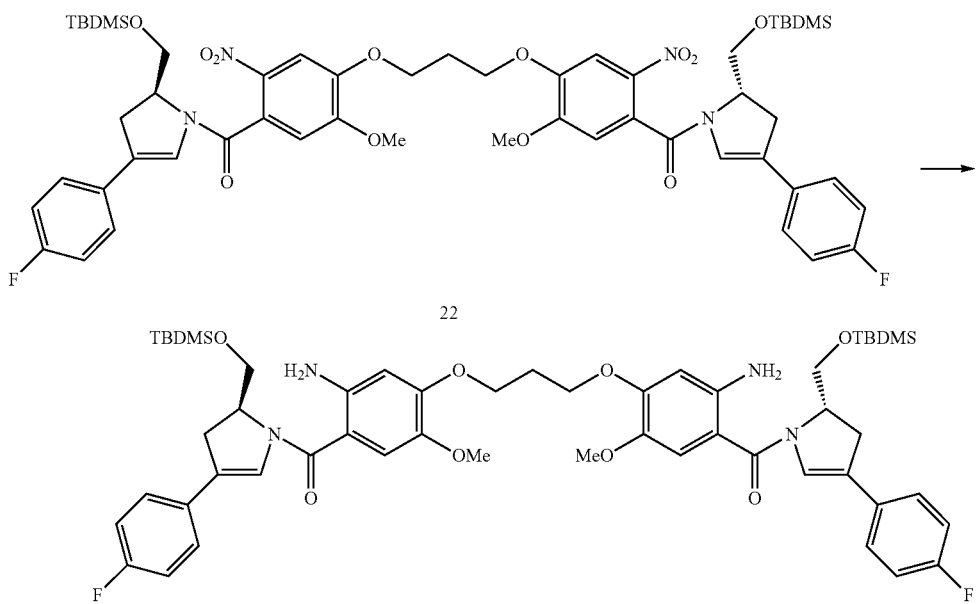

A solution of formic acid in ethanol (5% v/v, 100 mL) was added to a suspension of bis-nitro compound 22 (2.35 g, 2.25 mmol, 1 eq) and zinc dust (8.82 g, 0.135 mmol, 60 eq) in ethanol (35 mL). The reaction mixture was allowed to stir at room temperature for 25 min at which point TLC (methanol/chloroform, 2/98) and LC/MS (4.23 min (ES+) m/z (relative intensity) 986.3 ([M+H]$^{+\cdot}$, 10), 493.9 ([(M+2H)/2]$^{+\cdot}$, 100)) showed complete reaction. The suspension was filtered and the filtrate was partitioned between ethyl acetate (400 mL) and saturated aqueous NaHCO₃ (200 mL). The organics were washed with brine (100 mL), dried over MgSO₄, filtered and evaporated under reduced pressure to yield pure bis-amine 23 (2.20 g, 98%) which taken through directly to the next step.
(g)

slightly contaminated (4.32 min (ES+) m/z (relative intensity) 1070.58 ([M+H]$^{+\cdot}$, 100)). This compound was purified further by flash chromatography (gradient from 40/60 up to 20/80 hexane/diethyl ether) to give 700 mg (30%) of desired pure mono-alloc compound 24.

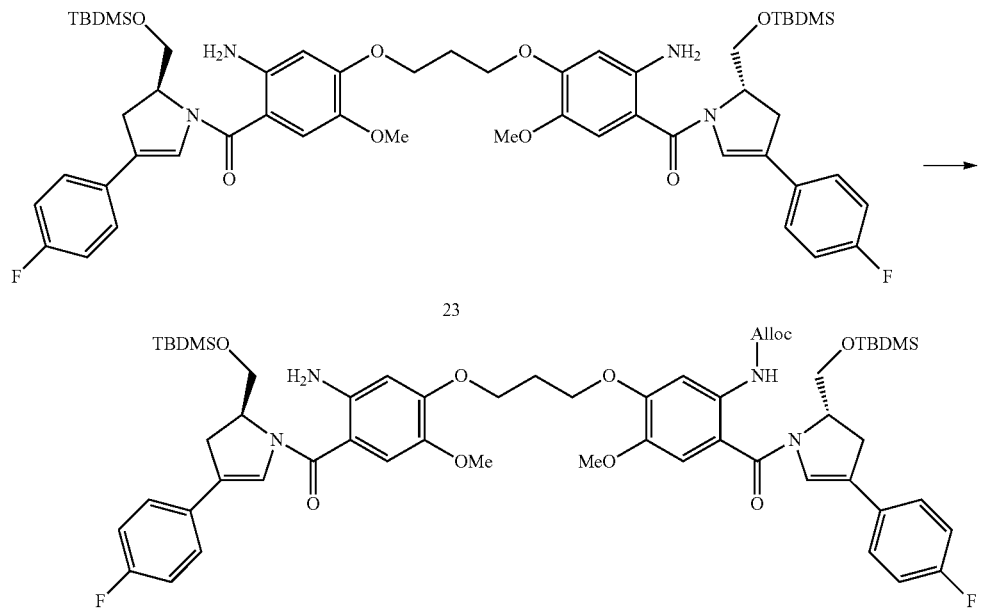

A solution of allyl chloroformate (0.209 mL, 1.97 mmol, 0.9 eq) in dry DCM (50 mL) was added dropwise to a solution of bis-anilino compound 23 (2.15 g, 2.18 mmol, 1 eq) and pyridine (0.335 mL, 4.14 mmol, 1.9 eq) in dry DCM (250 mL) at −78° C. The reaction mixture was allowed to stir at −78° C. for 2 hours, and allowed to warm to room temperature. The solution was washed with saturated aqueous copper sulphate (2×50 mL), water (250 mL), with brine (100 mL), dried over MgSO₄, filtered and evaporated under reduced pressure. The residue was purified by flash chromatography (gradient from 70/30 up to 30/70 hexane/EtOAc) to yield 668 mg (26.5%) of bis-Alloc protected compound as observed by LC/MS (4.45 min (ES+) m/z (relative intensity) 1154.32 ([M+H]$^{+\cdot}$, 100)) and 800 mg of desired mono-alloc protected compound Analytical Data: $[\alpha]^{22}_D$=−41 (c=0.16, CHCl₃); ¹H NMR (400 MHz, CDCl₃) δ 8.72 (bs, 1H), 7.88 (s, 2H), 7.25-7.18 (m, 4H), 7.02-6.93 (m, 4H), 6.93-6.83 (m, 3H), 6.80 (s, 1H), 6.36 (s, 1H), 6.00-5.84 (m, 1H), 5.32 (dd, 1H, J=1.37, J=17.21 Hz), 5.21 (dd, 1H, J=0.90, J=10.40 Hz), 4.85-4.71 (m, 2H), 4.60 (dd, 2H, J=1.02, J=5.62 Hz), 4.46 (s, 2H), 4.31 (t, 2H, J=5.96 Hz), 4.25 (t, 2H, J=6.31 Hz), 3.98 (m, 2H), 3.86 (m, 2H), 3.81 (s, 3H), 3.76 (s, 3H), 3.19-3.05 (m, 2H), 3.05-2.93 (m, 2H), 2.41 (p, 2H, J=6.16 Hz), 0.84 (m, 18H), 0.05 (m, 12H); IR (ATR, CHCl₃) 2952, 2359, 1732, 1652, 1601, 1507, 1472, 1406, 1225, 1119, 836, 777, 668 cm⁻¹; MS (ES⁺) m/z (relative intensity) 1070.58 ([M+H]$^{+\cdot}$, 100).
(h)

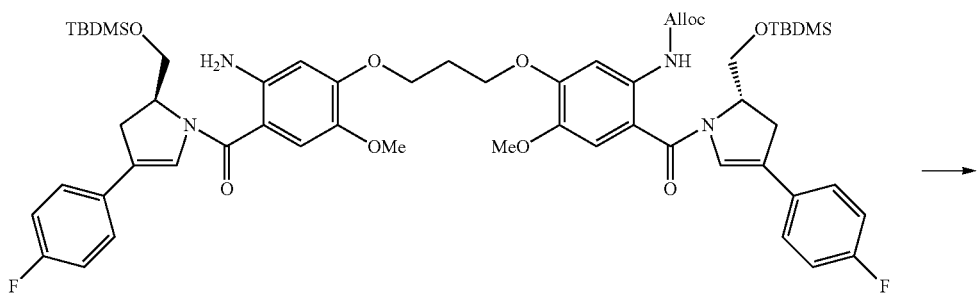

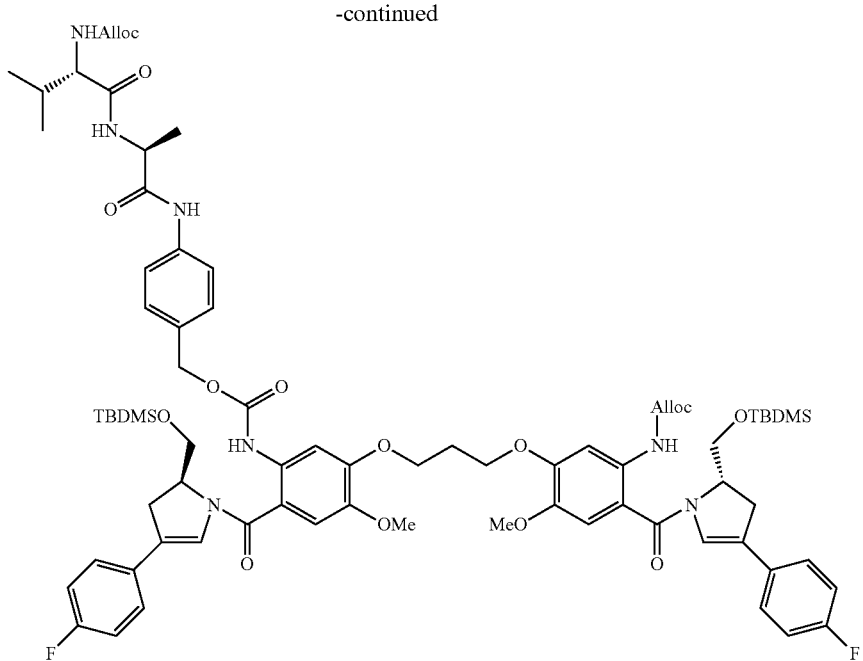

25

A solution of amine 24 (650 mg, 0.607 mmol, 1 eq) and TEA (220 µL, 1.58 mmol, 2.6 eq) in dry THF was added dropwise to a freshly prepared solution of triphosgene (81 mg, 0.273 mmol, 0.45 eq) in dry THF (4 mL) at 0° C. The white suspension was allowed to stir at 0° C. for 10 min. A solution of alcohol (Alloc-Val-Ala-PABOH, 229 mg, 0.607 mmol, 1 eq) and TEA (220 µL, 1.58 mmol, 2.6 eq) in dry THF (30 mL) was added rapidly. The white suspension was allowed to stir at room temperature for 15 minutes, then heated at 65° C. for 2 hours, then allowed to stir at room temperature overnight. The white TEA salts were removed by filtration over cotton wool. The filtrate was concentrated and purified by flash chromatography (Gradient, 0% MeOH in chloroform up to 3% MeOH in chloroform) to yield 220 mg of desired carbamate 25 (25%).

Analytical Data: $[\alpha]^{24}_D$=46.1° (c=0.13, CHCl$_3$); $^1$H NMR (400 MHz, CDCl$_3$) δ 8.70 (bs, 2H), 8.46 (s, 1H), 7.83 (s, 2H), 7.50 (m, 2H), 7.31 (d, 2H, J=8.50 Hz) 7.25-7.15 (m, 4H), 7.03-6.93 (m, 4H), 6.92-6.77 (m, 4H), 6.51 (d, 1H, J=7.48 Hz), 5.99-5.81 (m, 1H), 5.38-5.15 (m, 5H), 5.13-5.03 (m, 2H), 4.77 (bs, 2H), 4.66-4.53 (m, 5H), 4.38-4.22 (m, 4H), 4.08-3.94 (m, 3H), 3.93-3.81 (m, 2H), 3.79 (s, 6H), 3.20-3.05 (m, 2H), 3.05-2.94 (m, 2H), 2.41 (p, 2H, J=5.95 Hz), 2.22-2.08 (m, 1H), 1.45 (d, 3H, J=7.03 Hz), 0.94 (dd, 6H, J=6.81, 14.78 Hz), 0.84 (m, 18H), 0.14-0.02 (m, 12H); $^{13}$C NMR (100 MHz, CDCl$_3$) δ 171.7, 169.8, 165.9, 163.1, 153.6, 151.0, 144.3, 137.8, 132.4, 132.3, 132.0, 130.2, 129.2, 126.2, 126.1, 125.3, 123.3, 123.2, 119.8, 118.2, 118.0, 115.7, 115.5, 112.0, 106.0, 66.5, 66.2, 65.8, 65.4, 62.5, 60.4, 59.5, 56.6, 49.6, 30.8, 28.9, 25.7, 19.2, 18.2, 18.1, 17.7, 17.3, 14.2, −5.4; IR (ATR, CHCl$_3$) 2950, 2356, 1725, 1691, 1602, 1512, 1408, 1201, 1109, 1023, 832, 774, 668 cm$^{-1}$; MS (ES$^+$) m/z (relative intensity) 1473.43 ([M+H]$^+$, 100).

Example 3

(a)

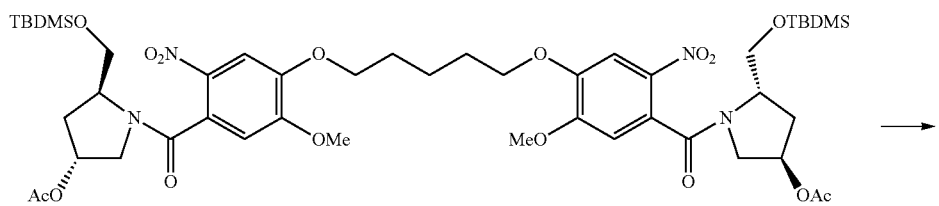

26

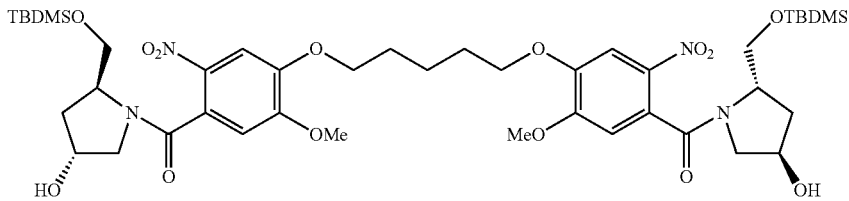

27

Compound 26 is compound 36 in WO 2006/111759.

A solution of aqueous potassium carbonate (4.33 g, 31.3 mmol, 5 eq. 30 mL) was added to a solution of the acetate 26 (6.3 g, 6.3 mmol) in methanol (100 mL). Further THF (20 mL) was added to a acid solubility and the resulting yellow solution allowed to stir for 30 minutes at room temperature. LCMS analysis revealed the complete consumption material and the formation of a new product ($R_t$=3.98 mins, M+H 922, 100%). The reaction solvent was evaporated and the residue diluted with water (100 mL) and the pH was adjusted to between 4 and 5 with citric acid (0.5 M). The aqueous solution was extracted with ethyl acetate (2×200 mL) and the combined extracts were washed with water (100 mL), brine (100 mL) and dried over magnesium sulphate. Ethyl acetate was removed by rotary evaporation under reduced pressure to give the desired product 27 as an off white foam (5.22 g, 90%).

LCMS $R_t$=3.98 mins, M+H 922, 100%

(b)

Solid TCCA (0.163 g, 0.7 mmol, 1.2 eq.) was added portionwise to a suspension of sodium acetate (0.115 g, 1.4 mmol, 2.4 eq.), starting material 27 (0.54 g, 0.59 mmol) and TEMPO (2.7 mg, 0.018 mmol, 0.03 eq.) in dry DCM (10 mL) at −10° C. (ice/acetone bath). The reaction mixture was allowed to stir at this temperature for 30 minutes, at which time LCMS indicated the reaction was complete. The reaction mixture was vacuum filtered through celite and the filter pad washed with DCM. The DCM solution was washed with saturated aqueous sodium bicarbonate (3×100 mL), water (100 mL), brine (100 mL) and dried over magnesium sulphate. DCM was removed by rotary evaporation under reduced pressure to give a yellow foam. The crude product was purified by gradient flash chromatography [20% n-hexane/80% ethyl acetate to 10% n-hexane/90% ethyl acetate], removal of eluent by rotary evaporation under reduced pressure afforded the desired product 28 as a yellow foam (0.478 g, 89%).

LCMS $R_t$=4.22 mins, M+H 918, 100%

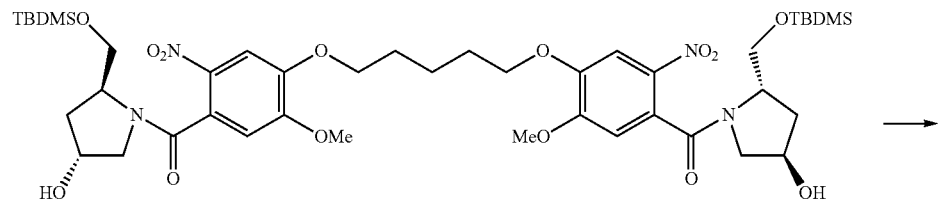

27

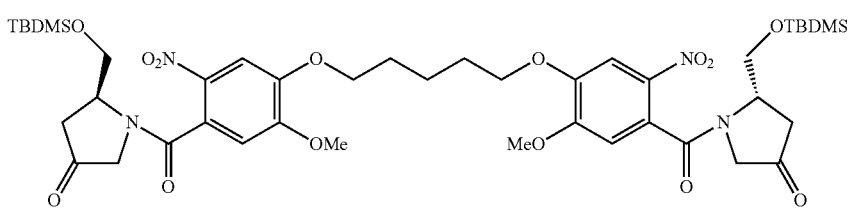

28

(c)

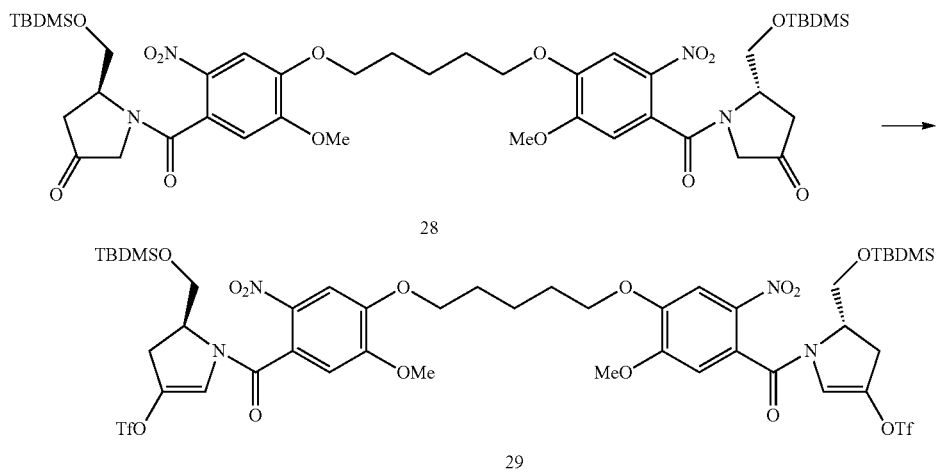

Anhydrous triflic anhydride (0.29 mL, 0.49 g, 1.7 mmol, 6 eq) was injected dropwise, to a vigorously stirred solution of the bis-ketone 28 (0.265 g, 0.29 mmol, 1 eq) and anhydrous 2,6-lutidine (0.27 mL, 0.25 g, 2.3 mmol, 8 eq) in dry DCM (10 mL) at −55° C. (dry ice/acetonitrile) under a nitrogen atmosphere. The reaction mixture was allowed to stir at −50° C. to −55° C. for 30 minutes. The cold reaction mixture was immediately diluted with water (10 mL), DCM (10 mL) and, with vigorous shaking, washed with water (1×100 mL), 0.5 M citric acid solution (2×25 mL) saturated NaHCO$_3$ (2×25 mL), water (50 mL), brine (50 mL) and dried (MgSO$_4$). Filtration and evaporation of the solvent under reduced pressure afforded the crude product which was purified by flash column chromatography [30% ethylacetate/70% n-hexane] to afford bis-enol triflate 29 (0.183 g, 54%) as a yellow foam.

MS (ES$^+$) m/z (relative intensity) 1181.8 ([M+H]$^{+\cdot}$, 100).

None of the corresponding 1,2 unsaturated compound was visible by NMR.

Example 4

(a)

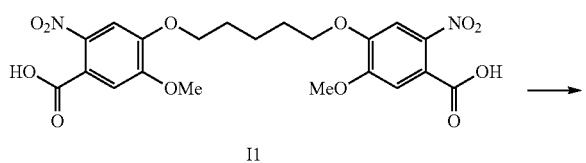

-continued

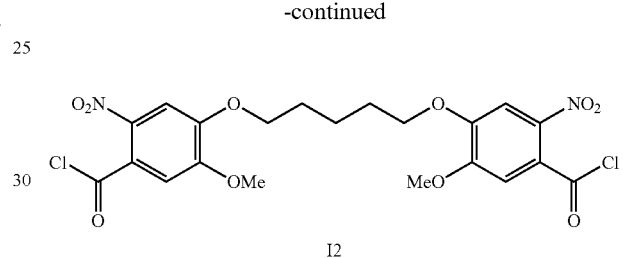

Oxalyl chloride (7.7 g, 5.3 mL, 60.7 mmol) was added to a suspension of the diacid 11 (10 g, 20.2 mmol) in dry dichloromethane (150 mL) whilst stirring under a nitrogen atmosphere. An aliquot of dimethylformamide (1 mL) was carefully added [vigorous effervescence!] to the reaction mixture. The reaction mixture was allowed to stir at room temperature for 18 hours. The diacid was observed to go into solution as it was converted to the acid chloride. The dichloromethane was removed by rotary evaporation under reduced pressure and the residue redissolved in the minimum of dry dichloromethane, the solution was diluted with diethyl ether until all the acid chloride I2 was precipitated. The precipitate was collected by vacuum filtration, washed with diethyl ether and dried in vacuo for 4 hours at 40° C.

(b)

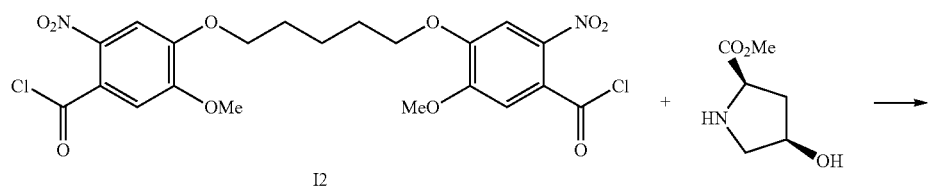

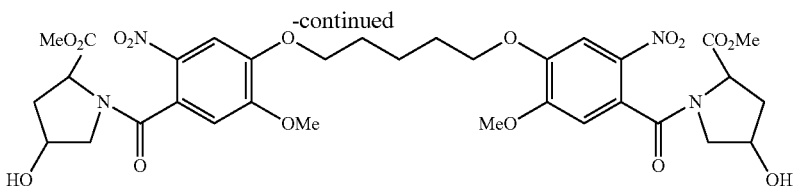

30

The solid acid chloride (I2) was added portionwise to a suspension of methyl 4-hydroxy-L-prolinate (8.45 g, 46.5 mmol) and tryethylamine (10.23 g, 14.1 mL, 101.1 mmol) in dry dichloromethane (95 mL), whilst maintaining the temperature in the reaction vessel between −40° C. and −45° C. After addition, the reaction mixture was allowed to stir at −40° C. for 1 hour and then to rise to room temperature. TLC (5% methanol in ethyl acetate) revealed a single product which was confirm by LC/MS. The reaction mixture was diluted with dichloromethane (100 mL) and washed with hydrochloric acid (1N, 2×250 mL), saturated aqueous sodium bicarbonate solution (2×200 L) water (200 mL) and brine (200 mL). The organic phase was dried over magnesium sulphate and excess solvent removed by rotary evaporation under reduced pressure to give a yellow foam 30 (12.8 g, 83% yield) which was used in the subsequent reaction without further purification (LC/MS 2.68 mins, M+H 749.43).

(c)

TCCA (20.97 g, 90.40 mmol, 1.4 eq) was added to a stirred solution of bis-alcohol 30 (46.79 g, 62.55 mmol, 1 eq), TEMPO (0.40 g, 2.58 mmol, 0.04 eq) and NaOAc (12.71 g, 154.97 mmol, 2.4 eq) in anhydrous DCM (500 mL) at room temperature at 0° C. (ice bath). The reaction mixture was allowed to stir at 0° C. for 1.5 hours, then filtered through celite, washing with DCM. The aqueous layer was separated, and the DCM layer was washed with sat. $NaHCO_3$ (2×500 mL), water (350 mL), brine (350 mL) and dried ($MgSO_4$). Filtration and evaporation of the solvent under reduced pressure afforded the crude product, which was purified by recrystallisation in a minimal amount of ethyl acetate. The recrystallised product was collected by vacuum filtration washed with ethyl acetate and dried in a vacuum oven to afford the bis-ketone 31 (36.2 g, 78%) as a pearl white solid.

Exact mass measurement (HRMS-ES$^+$) m/z: theoretical mass: 745.2205[M+H]$^+$;

measured mass: 745.2213 [M+H]$^+$.

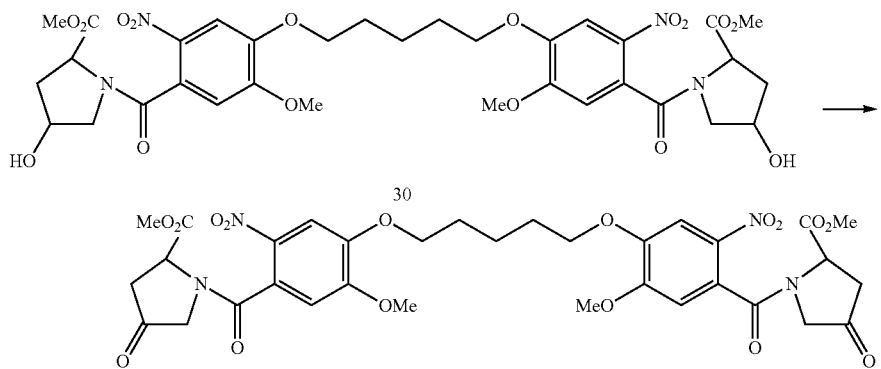

(d)

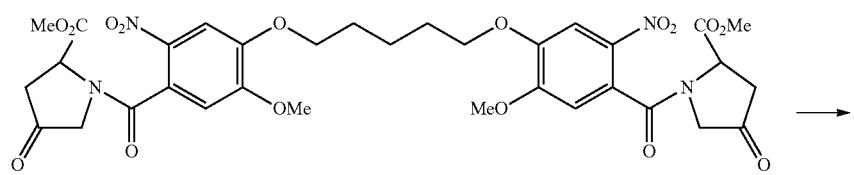

31

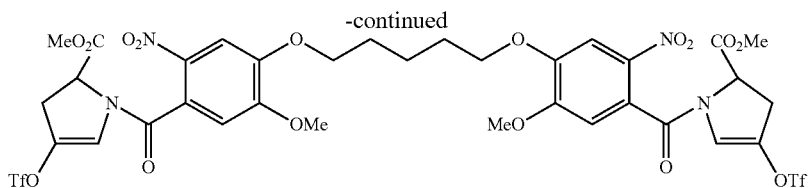

32

Anhydrous triflic anhydride (15.93 g, 9.50 mL, 56.45 mmol, 6 eq) was added dropwise by syringe, to a vigorously stirred solution of the bis-ketone 31 (7 g, 9.41 mmol, 1 eq) and anhydrous 2,6-lutidine (8.77 mL, 8.07 g, 75.27 mmol, 8 eq) in dry DCM (200 mL) at −50° C. (dry ice/acetonitrile) under a nitrogen atmosphere. The reaction mixture was allowed to stir at −45° C. to −50° C. for 25 minutes. The cold reaction mixture was immediately quenched with water (400 mL), DCM (400 mL) and, with vigorous shaking, washed with water (1×400 mL), 0.5 M citric acid solution (2×400 mL) saturated NaHCO$_3$ (2×400 mL), water (400 mL), brine (400 mL) and dried (MgSO$_4$). Filtration and evaporation of the solvent under reduced pressure afforded the crude product, which was purified by flash column chromatography [30% ethylacetate/70% n-hexane] to afford bis-enol triflate 32 (3.15 g, 33%) as a yellow foam. $[\alpha]^{19.2}_D = -682.5°$ (c=0.2, CHCl$_3$). IR ATR $\nu_{max}$/cm 1752, 1660, 1577, 1523, 1420, 1337, 1278, 1219, 1137, 1062, 823.

$^1$H NMR (400 MHz, CDCl$_3$). δ 7.741 (s, 2H), 6.91 (s, 2H), 6.26 (s, 2H), 5.17-5.21 (dd, 2H), 4.13-4.21 (m, 4H), 4.01 (s, 6H, OCH$_3$), 3.18 (s, 6h, OCH$_3$), 3.46-3.49 (dd, 2H), 2.99-3.04 (dd, 2H), 2.02-2.06 (m, 4H, CH$_2$), 1.75-1.79 (m, 2H, CH$_2$). Exact mass measurement (HRMS-ES$^+$) m/z: theoretical mass: 1009.1190 [M+H]$^+$; measured mass: 1009.1174 [M+H]$^+$.

None of the corresponding 1,2 unsaturated compound was visible by NMR.

(e)

A catalytic amount of Pd(Ph$_3$)$_4$ (0.34 g, 0.30 mmol, 0.04 eq) was added to a solution of trans-1-propan-1-yl bronic acid (1.92 g, 22.29 mmol, 3 eq), Na$_2$CO$_3$ (3.15 g, 29.72 mmol, 4 eq) and bis-triflate 1 (7.49 g, 7.73 mol, 1 eq) in toluene (60 mL), water (30 mL), ethanol (30 mL). The reaction mixture was allowed to stir at room temperature for 6 hours under a N$_2$ atmosphere, at which point TLC and LC-MS revealed the absence of starting material. The reaction mixture was filtered through Pd catalyst filter paper and excess solvent was removed by rotary evaporation under reduced pressure. The residue was dissolved in EtOAc (200 mL), washed with brine (200 mL), water (200 mL). The organic phase was dried over MgSO$_4$ and excess solvent was removed by rotary evaporation under reduced pressure afforded the crude product, which was purified by flash column chromatography [30% ethylacetate/70% n-hexane] to afford bis-ester 2 (3.15 g, 70%) as a yellow foam.

$^1$H NMR (400 MHz, CD$_3$OD). δ 7.73 (s, 2H) 6.91 (s, 2H), 6.5.97-60.01 (d, 2H), 5.90 (s, 2H), 5.48-5.54 (m, 2H), 5.09-5.13 (dd, 2H), 4.12-4.19 (m, 4H, CH$_2$), 3.99 (s, 6H, OCH$_3$), 3.86 (s, 6H, OCH$_3$), 3.19-3.23 (m, 2H), 2.77-2.83 (dd, 2H), 1.98-2.04 (m, 4H, CH$_2$), 1.75-7.77 (m, 8H, CH$_2$). Exact mass measurement (HRMS-ES$^+$) m/z: theoretical mass: 793.2932 [M+H]$^+$; measured mass: 793.2941 [M+H]$^+$.

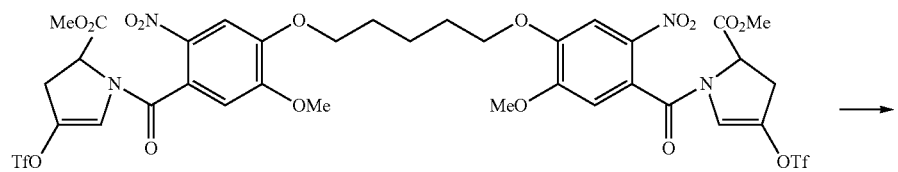

32

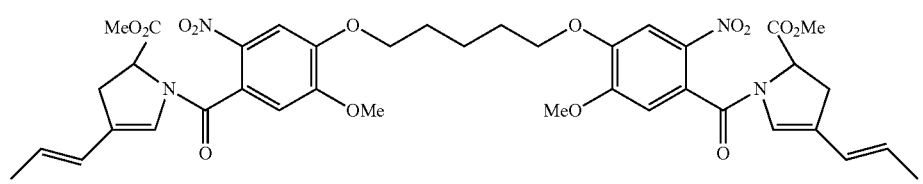

33

(f)

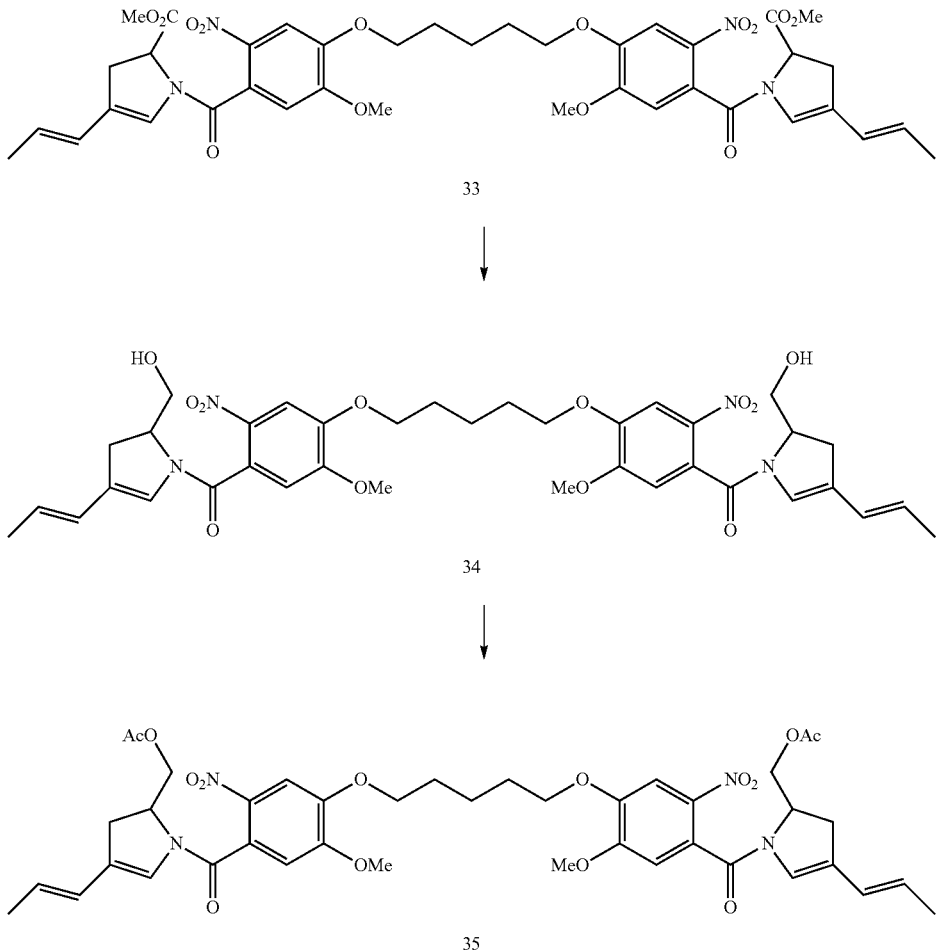

(i) Lithium borohydride (0.25 g, 11.55 mmol, 3 eq.) was added in one portion to a solution of the bis-ester 33 (2.83 g, 3.85 mmol, 1 eq.) in dry THF (40 mL) under a nitrogen atmosphere at 0° C. (ice bath). The reaction mixture was allowed to stir at 0° C. for 30 minutes and then allowed to warm to room temperature at which point precipitation of an orange gum was observed. The reaction mixture was allowed to stir at room temperature for a further 2 hours and then cooled in an ice bath and treated with water (20 mL) to give a yellow suspension. Hydrochloric acid (1M) was carefully added (vigorous effervescence!) until effervescence ceased. The reaction mixture was extracted with ethyl acetate (4×150 mL) and the combined organic layers were washed with water (2×200 mL), brine (200 mL) and dried (MgSO$_4$). Ethyl acetate was removed by rotary evaporation under reduced pressure to yield the product as a yellow foam (2.21 g, 84%).

$^1$H NMR (400 MHz, CD$_3$OD). δ 7.74 (s, 2H) 6.85 (s, 2H), 5.96-5.99 (d, 2H), 5.77 (s, 2H), 5.54-5.60 (m, 2H), 4.79 (m, 2H), 4.11-4.20 (m, 4H), 3.99-3.76 (m, 12H, OCH$_3$), 3.85-3.94 (m, 6H, OCH$_3$), 3.01-3.08 (m, 2H), 2.50 (m, 2H), 2.01-2.04 (m, 4H, CH$_2$), 1.76-1.77 (m, 8H, CH$_2$). Exact mass measurement (HRMS-ES$^+$) m/z: theoretical mass: 737.30034 [M+H]$^+$;

measured mass: 737.3033 [M+H]$^+$.

(ii) A solution of acetyl chloride (0.61 g, 0.55 mL, 7.80 mmol, 2.6 eq.) in dry DCM (40 mL) was added dropwise to a stirred solution of the bis-alcohol 34 (2.21 g, 3.60 mmol, 1 eq.) and triethylamine (0.92 g, 1.26 mL, 90.1 mmol, 3 eq.) in dry DCM (80 mL) at 0° C. under a nitrogen atmosphere. The reaction mixture was allowed to warm to room temperature and stirring was continued for one hour. TLC and LCMS revealed that the reaction was complete. The reaction mixture was washed with brine (2×100 mL) and dried (MgSO$_4$). Removal of DCM by rotary evaporation under reduced pressure gave the crude product. Flash chromatography [gradient elution 1:3 n-hexane/ethylacetate] furnished the pure bis-acetate as a yellow foam (0.81 g, 36%).

$^1$H NMR (400 MHz, CD$_3$OD). δ 7.73 (s, 2H) 7.01 (s, 2H), 5.97-6.01 (d, 2H), 5.77 (s, 2H), 5.53-5.75 (m, 2H), 4.93-4.94 (m, 2H), 4.50-4.65 (m, 2H), 4.35-4.45 (m, 2H), 4.11-4.19 (m, 4H,), 3.99 (s, 6H, OMe), 2.95-3.05 (m, 2H), 2.57-5.62 (m, 2H), 2.10 (s, 6H, OMe), 2.00-2.08 (m, 4H, CH$_2$), 1.75-1.78 (m, 8H). Exact mass measurement (HRMS-ES$^+$) m/z:

theoretical mass: 821.3245 [M+H]$^+$; measured mass: 821.3217[M+H]$^+$.

(g)

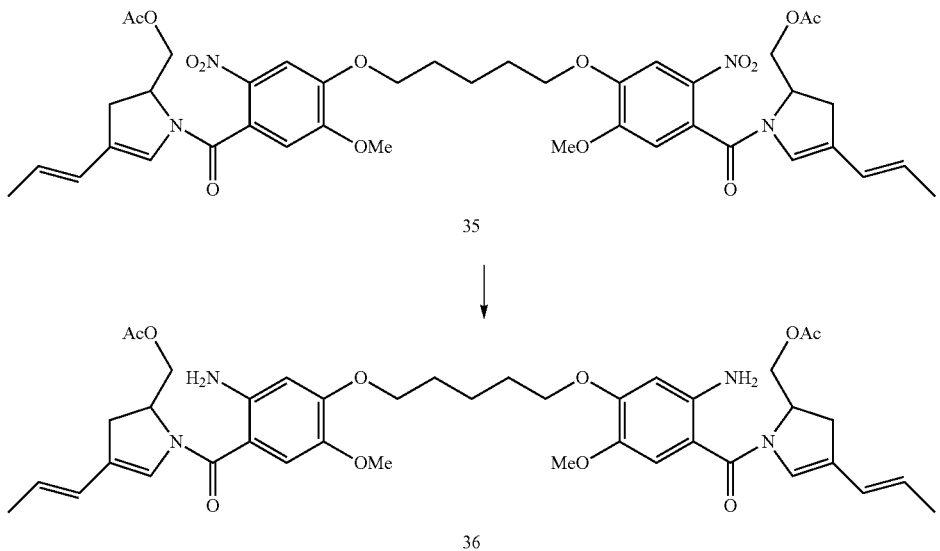

Zinc powder (3.18 g, 48.66 mmol, 30 eq.) was added to a solution of the nitro-acetate 35 (1.33 g, 1.62 mmol, 1 eq.) in ethanol (30 mL) and acetic acid (7.5 mL). The stirred reaction mixture was heated at reflux, with the yellow solution becoming colourless. The reaction was allowed to continue for one hour at which point LCMS indicated that the reaction was complete. The reaction mixture was allowed to cool, filtered through celite and the filter pad washed with DCM. The filtrate was washed with water (3×150 mL), saturated aqueous sodium bicarbonate (2×100 mL), brine (150 mL) and dried (MgSO$_4$). Rotary evaporation under reduced pressure gave the crude product. Flash chromatography [gradient elution 1:3 n-hexane/ethylacetate] furnished the pure bis-pale yellow foam 36 (0.52 g, 42%).

$^1$H NMR (400 MHz, CD$_3$OD). δ 6.75 (s, 2H) 6.46 (s, 2H), 6.26 (s, 2H), 6.09-6.13 (d, 2H), 5.51-5.56 (m, 2H), 4.88-4.92 (m, 2H), 4.45-4.55 (s, 4H), 4.33-4.45 (m, 4H), 4.03 (t, 4H), 3.79 (s, 6H, OMe), 2.92-1.95 (m, 2H), 2.53-5.58 (dd, 2H), 2.08 (s, 6H, OAc), 1.92-1.97 (m, 4H, CH$_2$), 1.80-1.82 (d, 6H. OMe), 1.69-1.71 (m, 2H). Exact mass measurement (HRMS-ES$^+$) m/z: theoretical mass: 761.3762 [M+H]$^+$; measured mass: 761.3742 [M+H]$^+$.

Example 5

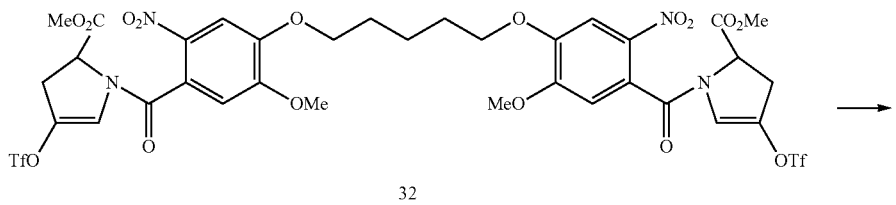

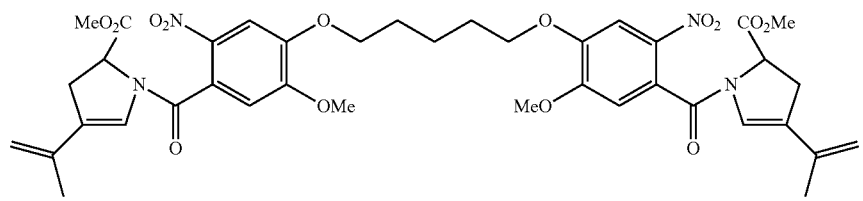

A catalytic amount of Pd(PPh₃)₄ (0.596 g, 0.515 mmol, 0.04 eq) was added to a solution of isopropenylboronic acid (6.5 g, 38.7 mmol, 3 eq), Na₂CO₃ (5.46 g, 51.55 mmol, 4 eq) and bis-triflate 32 (13 g, 12.9 mmol, 1 eq) in toluene (72 mL), water (144 mL), ethanol (72 mL). The reaction mixture was allowed to stir at room temperature for 36 hours under a N₂ atmosphere, at which point TLC and LC-MS revealed the absence of starting material. The residue was dissolved in EtOAc (200 mL), washed with brine (200 mL), water (200 mL). The organic phase was dried over MgSO₄ and excess solvent was removed by rotary evaporation under reduced pressure to afford the crude product, which was purified by flash column chromatography [30% EtOAc/70% n-hexane] to yield bis-ester 38 (6.2 g, 61%) as a yellow foam.

¹H NMR (400 MHz, CDCl₃). δ 7.74 (s, 2H) 6.94 (s, 2H), 5.98 (s, 2H), 5.12-5.16 (dd, 2H), 4.90 (s, 2H), 4.80 (s, 2H), 4.15-4.21 (m, 4H, CH₂), 4.00 (s, 6H, OCH₃), 3.87 (s, 6H, OCH₃), 3.27-3.34 (m, 2H), 2.83-2.88 (dd, 2H), 1.97-2.06 (m, 4H, CH₂), 1.74-1.81 (m, 8H, CH₂). Exact mass measurement (HRMS-ES⁺) m/z: theoretical mass: 793.2932 [M+H]⁺; measured mass: 793.31 [M+H]⁺.

Example 6

Part (i)

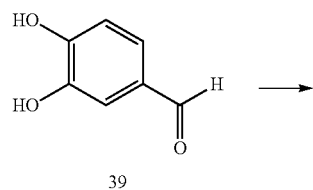

39

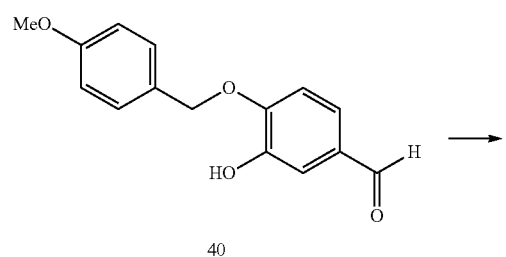

40

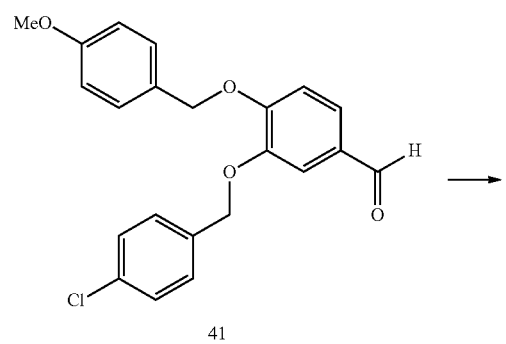

41

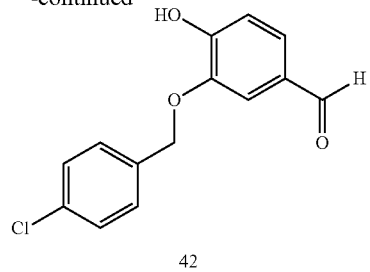

42

(a) 3-Hydroxy-4-(4-methoxy-benzyloxy)-benzaldehyde (40)

A solution of 4-methoxybenzyl chloride (100 g), 3,4-dihydroxy-benzaldehyde (88.2 g) and tetrabutylammonium iodide (23.6 g) was heated at 65° C. in acetone (0.5 L) over solid potassium carbonate (60 g) for 5 hours. The reaction mixture was poured into a mixture of ethyl acetate (2 L) and water (2 L). The organic phase was washed with aqueous potassium carbonate (1 L) and then extracted twice with 1N sodium hydroxide (3×300 mL). The sodium hydroxide was neutralised with dilute hydrochloric acid (1 N) and back extracted with ethyl acetate (2 L). Compound 40 (30 g) spontaneously precipitated during the work-up and was isolated by filtration. The organic layer was washed with water and brine and then dried over magnesium sulphate. Rotary evaporation under reduced pressure afforded the crude product as a gum which was digested from EtOAc/hexane/diethyl ether and collected by vacuum filtration and washed with a 50/50 mixture of hexane/diethyl ether (Total yield: 99 g, 59.9%, retention time 2.87 mins, ES⁻ 257.16).

(b) 3-(4-Chloro-benzyloxy)-4-(4-methoxy-benzyloxy)-benzaldehyde (41)

A solution of 4-chlorobenzyl chloride (67.9 g), 3-hydroxy-4-(4-methoxy-benzyloxy)-benzaldehyde (40) (99 g) and tetrabutylammonium iodide (14.1 g) was heated at reflux in acetone (0.4 L) over solid potassium carbonate (39.1 g) for 3 hours. Excess acetone was removed by rotary evaporation under reduced pressure and the resulting residue partitioned between ethyl acetate and dilute hydrochloric acid (0.5 N). The organic layer was washed with water and brine and then dried over magnesium sulphate. Ethyl acetate was removed by rotary evaporation under reduced pressure to afford the crude product. The crude oil was triturated with a 50/50 mixture of diethyl ether and hexane accompanied by vigorous stirring to afford the product as a colourless solid (108 g, 73% yield, retention time 3.70 mins, poor ionization, ES⁻ m/z 538.05). ¹H NMR (400 MHz, CDCl₃) δ 9.84 (s, 1H), 7.51-7.43 (m, 2H), 7.42-7.32 (m, 6H), 7.07 (d, J=8.1 Hz, 1H), 6.97-6.89 (m, 2H), 5.19 (s, 2H), 5.17 (s, 2H), 3.85 (s, 3H).

(c) 3-(4-Chloro-benzyloxy)-4-hydroxy-benzaldehyde (42)

A solution of 3-(4-chloro-benzyloxy)-4-(4-methoxy-benzyloxy)-benzaldehyde (41)(108 g) in acetic acid (500 mL) was heated at reflux overnight. Excess acetic acid was removed by rotary evaporation under reduced pressure (hard vacuum) and the resulting residue taken up in ethyl acetate. The organic layer was extracted with aqueous sodium hydroxide solution (1 N; 3×150 mL). The combined inorganic phases were neutralised with conc. hydrochloric acid and back extracted with ethyl acetate. The organic layer was washed with brine and dried over magnesium sulphate. The resulting oil was triturated with 50/50 diethyl ether/hexane, the solid product 42 collected by vacuum filtration and the precipitate washed with hexane (32.6 g, 44%, retention time 3.08 mins, ES⁻ 261.33).
Part (ii)
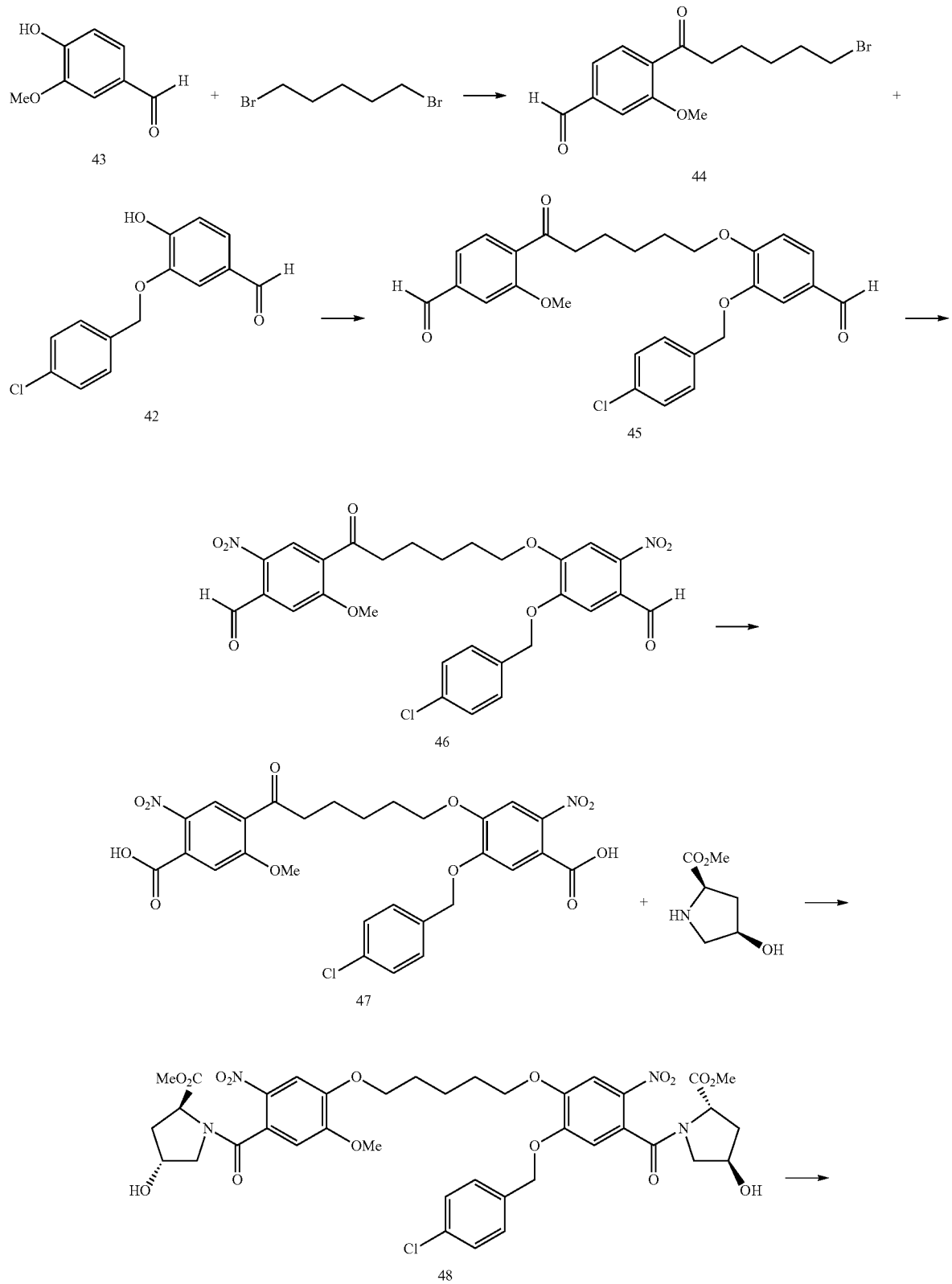

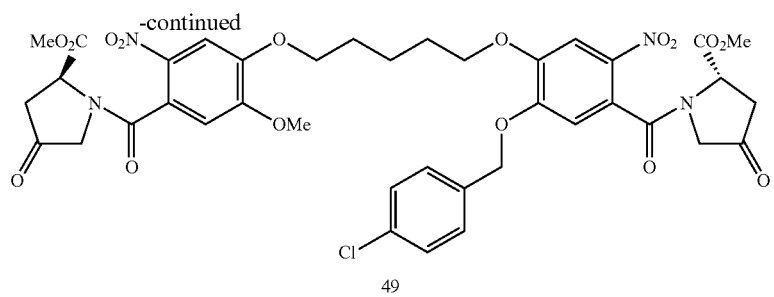

49

(a) 4-(6-bromo-hexanoyl)-3-methoxy-benzaldehyde (44)

An excess of 1,5-dibromopentane (100 g, 3 equivalents) was added to a suspension of vanillin (43) (22 g) and potassium carbonate (30 g) in acetone (700 mL). The reaction mixture was heated at reflux for 2.5 hours and then allowed to stir at room temperature overnight, at which time TLC and LC/MS showed the reaction to be complete. The suspension was subjected to vacuum filtration and the resulting acetone solution was evaporated to dryness under reduced pressure. The residue was applied to a pad of silica gel and washed with 10% ethyl acetate in hexane (2 L) followed by 25% ethyl acetate in hexane to elute the product, removal of excess solvent by rotary evaporation under reduced pressure afforded the product 44 as an oil which crystallised on standing in freezer (35 g, 80% yield).

LC/MS 3.30 mins, ES$^+$ 301 and 303.24 (arising from bromine isotopes).

(b) Compound 45

A solution of 4-(6-bromo-hexanoyl)-3-methoxy-benzaldehyde 44 (34.05 g), 3-(4-Chloro-benzyloxy)-4-hydroxy-benzaldehyde 42 (29.7 g) and tetrabutylammonium iodide (4.17 g) in acetone (500 mL) was heated over potassium carbonate (11.7 g) overnight at 50° C. The reaction mixture was then heated at reflux for 5 hours to bring the reaction to completion. Excess acetone was removed by rotary evaporation under reduced pressure and the resulting residue partitioned between ethyl acetate (500 mL) and water (300 mL). The organic phase was washed sequentially with aqueous sodium hydroxide (1 N; 2×100 mL), dilute hydrochloric acid (1 N; 2×100 mL), water, brine and then dried over magnesium sulphate. Removal of excess ethyl acetate by rotary evaporation under reduced pressure afforded the crude product 45 as an oil which was triturated with diethyl ether (100 mL) to afford a colourless solid which was collected by vacuum filtration (47.85 g, 88% yield, retention time 3.75, 483 ES$^+$ m/z).

(c) Compound 46

Fuming nitric acid (100 mL) was added dropwise to a suspension of compound 45 (45 g) in acetic acid (450 mL). The temperature of the reaction was maintained between 10 and 25° C. using an ice bath. Over the course of the reaction the suspension went into solution and TLC indicated that the reaction was complete. The reaction mixture was poured carefully onto a mixture of crushed ice and water, the resulting precipitate was collected by vacuum filtration, dissolved in dichloromethane and dried over magnesium sulphate. Removal of solvent by rotary evaporation under reduced pressure afforded the crude product which was purified by column chromatography (silica gel; gradient, 80% dichloromethane/ 20% hexane to 100% dichloromethane). The pure fractions were combined and excess eluent removed by rotary evaporation under reduced pressure to afford the pure product 46 (20 g, 37.4%). Poor ionisation by MS. Retention time 3.90 min. TLC: Rf 0.20 (DCM). $^1$H NMR (400 MHz, CDCl$_3$) δ 10.46 (s, 1H), 10.43 (s, 1H), 7.63 (s, 1H), 7.59 (s, 1H), 7.48 (s, 1H), 7.44-7.33 (m, 5H), 5.23 (s, 2H), 4.23 (t, J=6.4 Hz, 2H), 4.18 (t, J=6.4 Hz, 2H), 3.99 (s, 3H), 2.09-1.98 (m, 4H), 1.81-1.71 (m, 2H).

(d) Compound 47

A solution of sodium chlorite (15 g) and sodium dihydrogenphosphate (6.46 g) (NaH$_2$PO$_4$) in water (200 mL) was added to a solution of compound 46 (19 g) in THF (200 mL) and dichloromethane (10 mL) at room temperature. Hydrogen peroxide (60% w/w, 22.23 mL) was immediately added to the vigorously stirred biphasic mixture. The reaction was initiated by addition of hydrochloric acid (1N, 50 mL) sufficient to lower the pH of the reaction mixture to approximately 3.5. The reaction mixture evolved gas (oxygen), the starting material dissolved and the temperature of the reaction mixture rose to 35° C. After LC/MS revealed reaction to be complete, the reaction mixture was cooled in an ice bath and hydrochloric acid (1N) was added to lower the pH to between 1 and 2. The reaction mixture was then extracted with ethyl acetate (500 mL) and the organic phases washed with brine (300 mL) and a solution of sodium metabisulfite (20 g in 300 mL of water). The organic phase was dried over magnesium sulphate, filtered, and excess solvent removed by rotary evaporation under reduced pressure. The crude product was suspended in diethyl ether and the pure product collected by vacuum filtration (18 g, 90% yield, LC/MS 3.08 mins, m/z ES$^-$ 602.87).

(e) Compound 48

Dimethylformamide (1 mL) was carefully added to a solution of compound 47 (17.8 g) oxalyl chloride (7.7 mL) in dichloromethane (250 mL) and the reaction allowed to proceed overnight. The volatiles were removed by rotary evaporation under reduced pressure, followed by trituration with diethyl ether. The residue was redissolved in dichloromethane (200 mL) and was added drop wise to a suspension of 4-hydroxyproline methyl ester (22.3 g) in dichloromethane in the presence of triethylamine (20.5 mL) at −40° C. After addition, the reaction mixture was allowed to return slowly to room temperature by removal of the cooling bath. The reaction mixture was washed sequentially with aqueous hydrochloric acid (1N, 100 mL) saturated sodium bicarbonate (2×100 mL), brine (100 mL) and dried over magnesium sulphate. Removal of excess solvent afforded compound 48 (26.76 g, quantitative yield, LC/MS 2.80 mins, m/z ES+ 859.09).

(f) Compound 49

TCCA (10.1 g) was added to a stirred solution of compound 48 (26.76 g), TEMPO (195 mg) and sodium acetate (7.15 g) in dry dichloromethane (400 mL) at 10° C. The reaction mixture was vigorously stirred for 1.5 hours at room temperature, at which point TLC (ethyl acetate) revealed complete consumption of the material. The reaction mixture was filtered through celite and the filtrate washed with aqueous sodium metabisulphite (1N, 200 mL), water (200 mL), saturated sodium bicarbonate (150 mL), brine (100 mL) and dried over magnesium sulphate. Rotary evaporation under reduced pressure afforded product 11 (24 g, yield 90%, LC/MS 3.42 mins, m/z ES+ 854.97).

Part (iii)

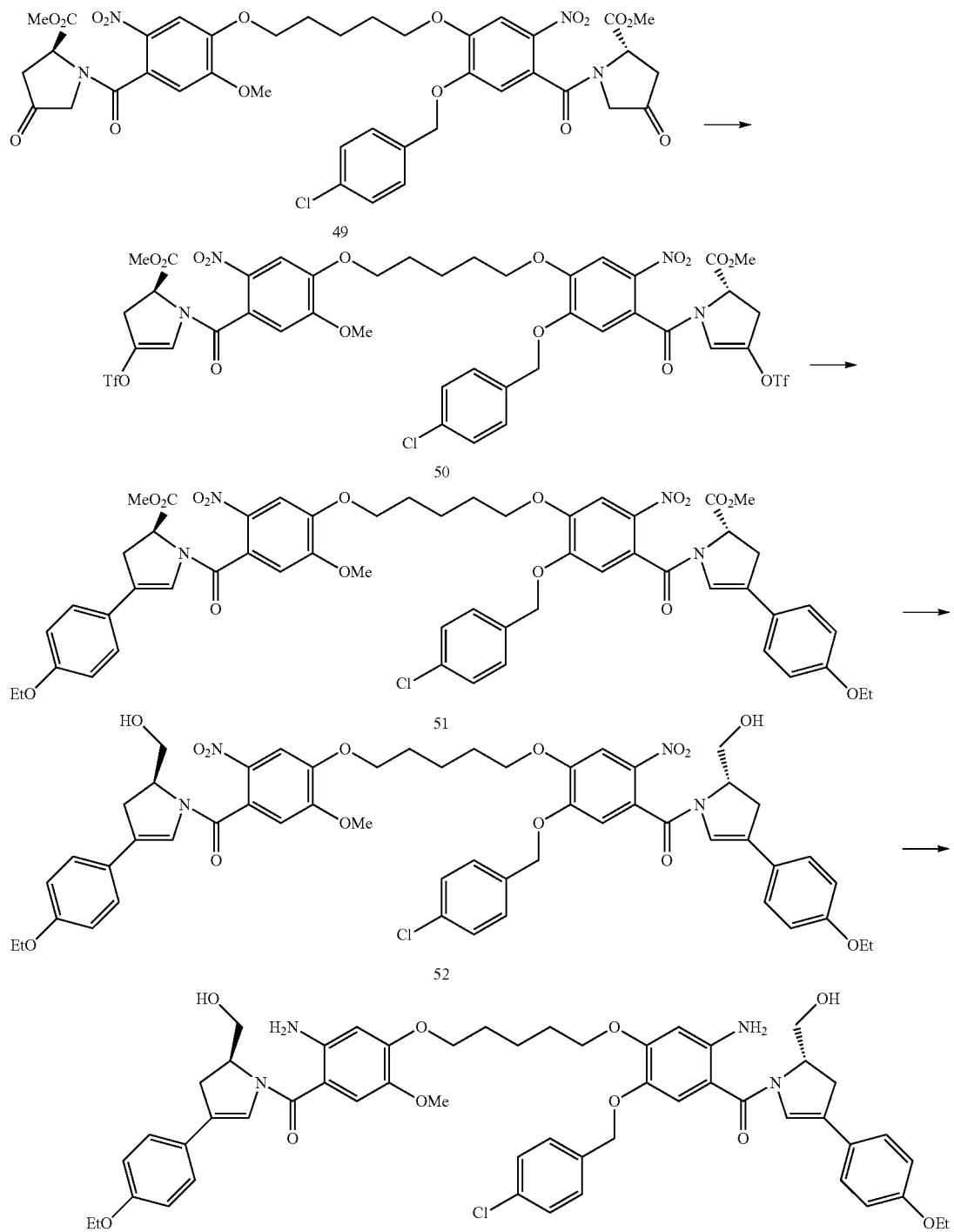

(a) Compound 50

Triflic anhydride (45.5 g) was added drop wise over 10 minutes to a vigorously stirred suspension of compound 49 (23 g) in dry dichloromethane (350 mL) in the presence of 2,6-lutidine (19.3 mL) at −60° C. (acetone/dry ice bath). The temperature of the reaction mixture was carefully allowed to rise to between −50° C. and −45° C. Reaction was observed to take place in this temperature range over a period of 40 minutes. The reaction was quenched by the addition of water directly to the reaction flask. The cold reaction mixture was washed with water (300 mL), followed by citric acid (0.5 N, 200 mL) saturated sodium bicarbonate (200 mL) and saturated brine (100 mL). The dichloromethane layer was dried over magnesium sulphate and rotary evaporation under reduced pressure afforded the crude product. The crude product was purified by flash chromatography (silica gel; gradient elution: 20% ethyl acetate/80% hexane to 50% ethyl acetate/50% hexane). Pure fractions were combined and removal of excess eluent afforded pure product 50 (11 g, 36% yield, retention time 3.67, ES$^+$ 1119 m/z)

None of the corresponding 1,2 unsaturated compound was visible by NMR.

(b) Compound 51

Tetrakis(triphenylphosphine)palladium(0) (682 mg) was added to triflate 50 (11 g), 4-ethoxybenzeneboronic acid (4.24 g) and sodium carbonate (5.4 g) in a mixture of toluene (220 mL), ethanol (110 mL) and water (110 mL). The reaction mixture was allowed to stir for 5 hours under an argon atmosphere at 32° C. During this time the product was observed to precipitate from the reaction mixture. The reaction mixture was diluted with ethyl acetate and washed with water, brine and dried over magnesium sulphate. After filtration excess ethyl acetate was removed by rotary evaporation under reduced pressure. The crude coupling product was purified by flash column chromatography (silica gel; gradient 50/50 ethyl acetate/hexane to 70/30 ethyl acetate/hexane). Pure fractions were combined and removal of excess eluent afforded the pure product 51 as an orange solid (8.6 g, 82% yield, LC/MS 3.72 mins, m/z ES$^+$ 1063.25).

(c) Compound 52

Lithium borohydride (6.4 mg) was added in one portion to a suspension of the methyl ester 51 (100 mg) in dry THF (5 mL) at room temperature. The suspension went into solution and the formation of a new orange precipitate was observed. After 30 mins an aliquot of the reaction mixture was removed from the flask and subjected to a mini work-up, TLC of this material revealed that the reaction was complete. The bulk reaction mixture was cooled (ice bath) and excess lithium borohydride was quenched by the addition of acetone (1 mL). The quenched reaction mixture was extracted with ethyl acetate and washed with water and brine. The organic phase was dried over magnesium sulphate, filtered and excess ethyl acetate was removed by rotary evaporation under reduced pressure to afford the product 52 (75 mg; 79%, LC/MS 3.52 mins, m/z ES$^+$ 1007.25).

(d) Compound 53

Zinc powder (5 g) was added to a solution of bis nitro alcohol 52 (1 g) in ethanol (15 mL), followed by a solution of formic acid in ethanol (5% v/v; 40 mL). The reaction mixture was allowed to stir at room temperature and closely monitored by TLC and LC/MS. After 15 minutes, the reaction was deemed complete as no trace of starting material, or intermediates were detected. The mixture was decanted and filtered through cotton wool. The filtrate was partitioned between ethyl acetate (300 mL) and saturated aqueous NaHCO$_3$ (300 mL). The pH was adjusted to basic. The organic layer was further washed with brine (200 mL) and dried over magnesium sulphate. Excess solvents were removed by rotary evaporation under reduced pressure to afford the product 53 (600 mg; 64%, LC/MS 3.45 mins, m/z ES$^+$ 947.29).

Example 7

Part (i)

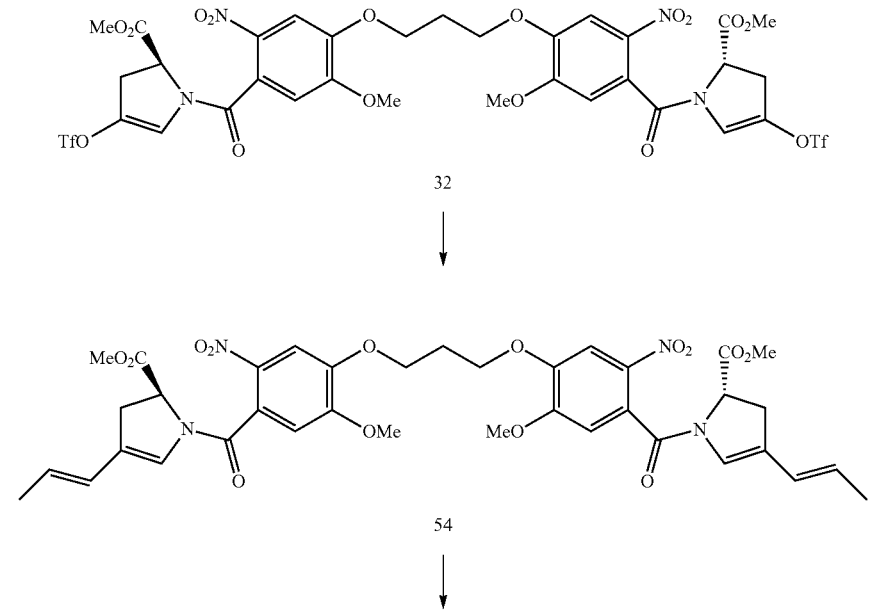

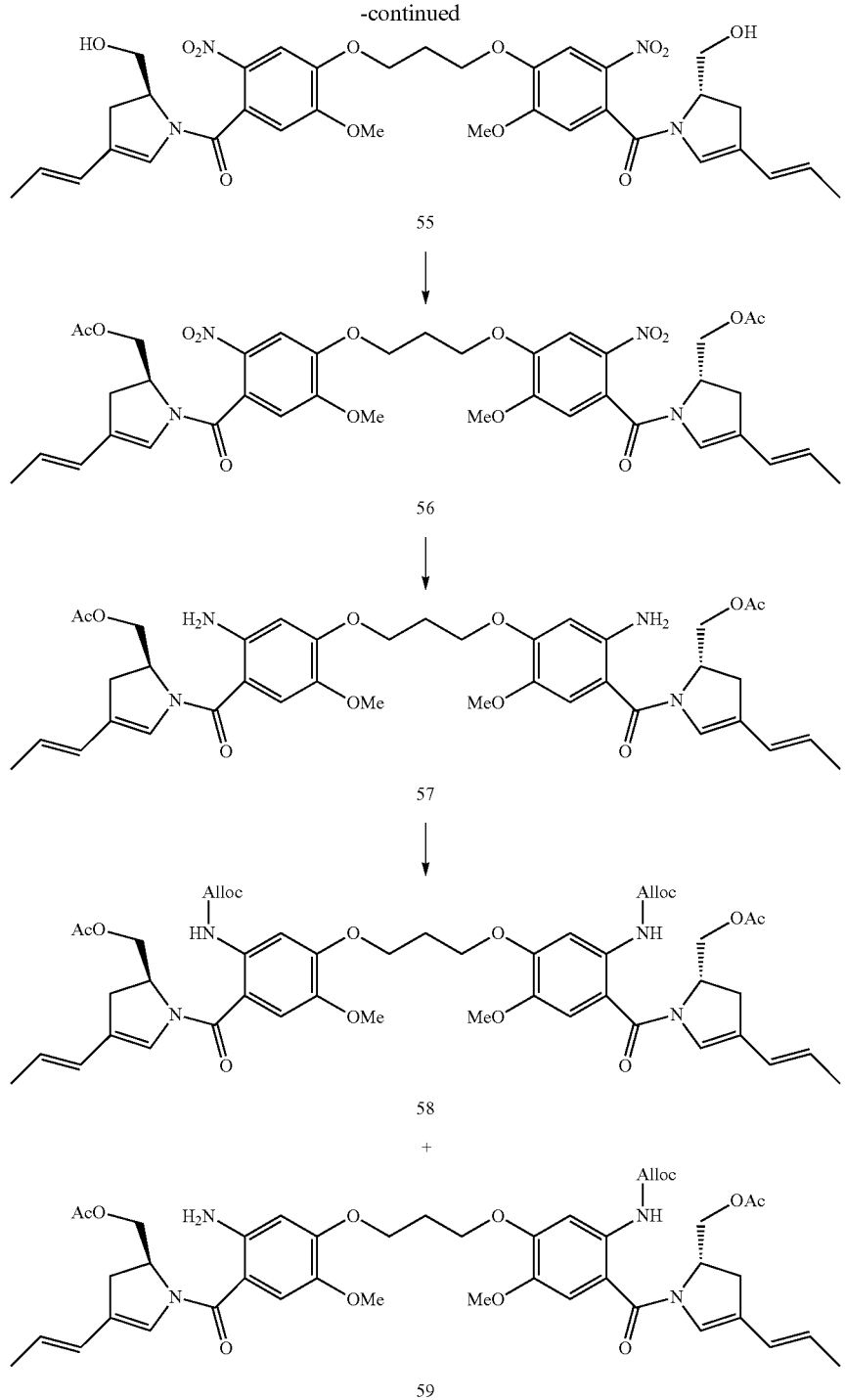

(a) (2S,2'S,E)-dimethyl 1,1'-(4,4'-(propane-1,3-diyl-bis(oxy))bis(5-methoxy-2-nitrobenzoyl))bis(4-((E)-prop-1-en-1-yl)-2,3-dihydro-1H-pyrrole-2-carboxylate) (54)

Tetrakis(triphenylphosphine)palladium(0) (21.6 mg) was added to triflate 32 (230 mg), trans-propenylboronic acid (52.3 mg) and sodium carbonate (129 mg) in a mixture of toluene (5 mL), ethanol (2.5 mL) and water (2.5 mL). The reaction mixture was allowed to stir for 3 hours under an argon atmosphere at 32° C. The reaction mixture was diluted with ethyl acetate and washed with water, brine and dried over magnesium sulphate. After filtration excess ethyl acetate was removed by rotary evaporation under reduced pressure. The crude coupling product was purified by flash column chromatography (silica gel; gradient 50%/50% ethyl acetate/hexane to 80%/20% ethyl acetate/hexane). Pure fractions were combined and removal of excess eluent afforded the pure product 54 as an orange solid (110 mg, 61.4% yield, LC/MS 3.52 mins, m/z ES+ 764.92). The reaction was repeated on a larger scale to afford 7.21 g of the Suzuki coupling product. $^1$H NMR (400 MHz, CD$_3$OD). δ 7.78 (s, 2H) 6.92 (s, 2H), 5.98 (d, 2H), 5.89 (s, 2H), 5.46-5.55 (m, 2H), 5.10 (dd, 2H), 4.37 (t, 4H), 3.93-4.00 (m, 6H), 3.86 (s, 6H), 3.19-3.26 (m, 2H), 2.80 (dd, 2H), 2.45-2.51 (m, 2H), 1.77 (d, 6H OCH$_3$).

(b) (S,E)-((propane-1,3-diylbis(oxy))bis(5-methoxy-2-nitro-4,1-phenylene))bis(((S)-2-(hydroxymethyl)-4-((E)-prop-1-en-1-yl)-2,3-dihydro-1H-pyrrol-1-yl)methanone) (55)

The bis-ester 54 (7.21 g) was added in one portion as a solid to a solution of lithium borohydride (622 mg) in dry tetrahydrofuran (300 mL), at 0° C. (ice bath). The ice bath was removed and the reaction mixture allowed to reach room temperature. After 1 hour, TLC (following mini work up with ethyl acetate water) revealed that the reaction was not complete and so additional lithium borohydride (0.75 equivalents) was added. The reaction mixture was allowed to stir for a further 2.5 hours at which time TLC (following mini work up) revealed the reaction to be complete, Remaining lithium borohydride was quenched with a large excess of ethyl acetate (ice bath) and the reaction mixture was allowed to stir for 50 mins. The organic phase was washed with water, brine and dried over magnesium sulphate. Magnesium sulphate was removed by vacuum filtration and the ethyl acetate removed by rotary evaporation under reduced pressure to afford the diol 55 (5.46 g, 82% yield) which was used in the next reaction without further purification (LC/MS 3.17 mins, m/z ES$^+$ 708.84). $^1$H NMR (400 MHz, CD$_3$OD). δ 7.78 (s, 2H) 6.85 (s, 2H), 5.97 (d, 2H), 5.77 (s, 2H), 5.61-5.53 (m, 2H), 4.75-4.82 (m, 2H), 4.38 (t, 4H), 3.89-4.00 (m, 12H), 3.01-3.08 (m, 2H) 2.46-2.51 (m, 4H), 1.77 (d, 6H OCH$_3$).

(c) ((2S,2'S,E)-1,1'-(4,4'-(propane-1,3-diylbis(oxy))bis(5-methoxy-2-nitrobenzoyl))bis(4-((E)-prop-1-en-1-yl)-2,3-dihydro-1H-pyrrole-2,1-diyl))bis(methylene)diacetate (56)

A solution of acetyl chloride (1.64 mL) in dry dichloromethane (40 mL) was added dropwise to a solution of the bis alcohol 55 (6.2 g) in dichloromethane (200 mL) in the presence of triethylamine (3.68 mL) at 0° C. The reaction mixture was allowed to warm to room temperature and the reaction was monitored by TLC and LC/MS. Once reaction was complete the organic phase was washed sequentially with water, citric acid (0.5 N), saturated sodium bicarbonate and brine. The organic layer was dried over magnesium sulphate, filtered and excess dichloromethane removed by rotary evaporation under reduced pressure. The residue was subjected to column chromatography (silica gel; gradient, 60% ethyl acetate/40% hexane to 70% ethyl acetate/30% hexane). Pure fractions were combined and removal of excess eluent afforded the bis-acetate 56 (2.50 g, 36% yield, LC/MS 3.60 mins, m/z ES$^+$ 792.63), $^1$H NMR (400 MHz, CDCl$_3$) δ 7.77 (d, J=3.4 Hz, 2H), 6.89 (s, 2H), 5.99 (d, J=15.2 Hz, 2H), 5.78 (s, 2H), 5.65-5.45 (m, J=15.4, 6.8 Hz, 2H), 5.02-4.86 (m, J=9.7, 5.5 Hz, 2H), 4.57 (s, 2H), 4.37 (t, J=5.9 Hz, 4H), 4.00 (s, 6H), 3.10-2.92 (m, J=10.7 Hz, 2H), 2.60 (dd, J=16.3, 3.1 Hz, 2H), 2.52-2.43 (m, 2H), 2.10 (s, 6H), 1.78 (d, J=6.7 Hz, 4H).

(d) ((2S,2'S,E)-1,1'-(4,4'-(propane-1,3-diylbis(oxy))bis(2-amino-5-methoxybenzoyl))bis(4-((E)-prop-1-en-1-yl)-2,3-dihydro-1H-pyrrole-2,1-diyl))bis(methylene)diacetate (57)

Zinc powder (10 g) was added to a solution of bis-nitro compound 56 (2.5 g) in ethanol (20 mL) and ethyl acetate (20 mL), followed by a solution of formic acid in ethanol (5% v/v; 100 mL). The reaction was exothermic with the temperature rising to 33° C., the temperature was brought down to 15° C. with an ice bath and the reaction mixture was allowed to stir whilst being closely monitored by TLC and LC/MS. After 30 mins, the reaction was deemed complete as no trace of starting material, or intermediates were detected. The mixture was decanted and filtered through cotton wool. The filtrate was partitioned between ethyl acetate (300 mL) and saturated aqueous NaHCO$_3$ (300 mL). The organic layer was further washed with brine (200 mL) and dried over magnesium sulphate. Excess solvents were removed by rotary evaporation under reduced pressure to afford the product 57 (2.09 g; 90% yield, LC/MS 3.35 mins, m/z ES$^+$ 732.06). $^1$H NMR (400 MHz, CDCl$_3$) δ 6.76 (s, 2H), 6.45 (s, 2H), 6.33 (s, 2H), 6.12 (d, J=15.3 Hz, 2H), 5.54 (dq, J=13.2, 6.6 Hz, 2H), 4.90 (td, J=9.6, 4.5 Hz, 2H), 4.48 (s, 4H), 4.42-4.33 (m, 4H), 4,23 (t, J=6.1 Hz, 4H), 3.79 (s, 6H), 2.95 (dd, J=16.0, 10.4 Hz, 2H), 2.55 (dd, J=16.2, 3.5 Hz, 2H), 2.42-2.32 (m, 2H), 2.07 (s, 6H), 1.81 (d, J=6.6 Hz, 6H).

(e) ((2S,2'S,E)-1,1'-(4,4'-(propane-1,3-diylbis(oxy))bis(2-(((allyloxy)carbonyl)amino)-5-methoxybenzoyl))bis(4-((E)-prop-1-en-1-yl)-2,3-dihydro-1H-pyrrole-2,1-diyl))bis(methylene)diacetate (58) and ((S)-1-(4-(3-(4-((S)-2-(acetoxymethyl)-4-((E)-prop-1-en-1-yl)-2,3-dihydro-1H-pyrrole-1-carbonyl)-5-(((allyloxy)carbonyl)amino)-2-methoxyphenoxy)propoxy)-2-amino-5-methoxybenzoyl)-4-((E)-prop-1-en-1-yl)-2,3-dihydro-1H-pyrrol-2-yl)methyl acetate (59)

A solution of allyl choloroformate in dry dichloromethane was added drop wise to a solution of the his-aniline 57 and pyridine in dry dichloromethane at −78° C. The reaction mixture was allowed to stir at −78° C. for 2 hours and then allowed to return to room temperature. The reaction mixture was washed sequentially with aqueous copper II sulphate, water, saturated sodium bicarbonate and brine. The organic layer was dried over magnesium sulphate, filtered under vacuum and excess dichloromethane was removed by rotary evaporation under reduced pressure. TLC and LC/MS revealed the presence of both the desired mono Alloc product 59 and the bis-Alloc product 58. The product mixture was subjected to column chromatography (silica gel; gradient 40% ethyl acetate/60% hexane to 70% ethyl acetate/30% hexane). Pure fractions containing the bis-alloc product were collected and excess eluent was removed by rotary evaporation under reduced pressure afforded compound 58 (956 mg, 37% yield). Pure fractions containing the desired mono Alloc product 59 were also collected and combined, excess eluent was removed by rotary evaporation under reduced pressure to afford the product (580 mL, 25% yield). Compound 59 LC/MS 3.58 mins, ES$^+$ 817.02), compound 58 LC/MS 3.80 mins, ES$^+$ 901.14. $^1$H NMR (58) (400 MHz, CDCl$_3$) δ 8.60 (s, 2H), 7.83 (s, 2H), 6.78 (s, 2H), 6.38 (s, 2H), 6.08 (d, J=15.4 Hz, 2H), 5.94 (ddt, J=17.1, 10.5, 5.7 Hz, 2H), 5.54 (dq, J=13.5, 6.7 Hz, 2H), 5.34 (dq, J=17.2, 1.5 Hz, 2H), 5.27-5.17 (m, 2H), 4.90 (td, J=9.5, 4.6 Hz, 2H), 4.62 (dd, J=5.7, 1.2 Hz, 4H), 4.46-4.20 (m, 8H), 3.81 (s, 6H), 2.94 (dd, J=15.7, 10.5 Hz, 2H), 2.52 (dd, J=16.1, 3.5 Hz, 2H), 2.40 (p, J=6.0 Hz, 2H), 2.06 (s, 6H), 1.78 (dd, J=6.7, 0.9 Hz, 6H). $^1$H NMR (59) (400 MHz, CDCl$_3$) δ 8.60 (s, 1H), 7.85 (s, 1H), 6.80 (s, 1H), 6.72 (s, 1H), 6.42 (s, 1H), 6.37 (s, 1H), 6.33 (s, 1H), 6.08 (dd, J=15.4, 6.1 Hz, 2H), 6.00-5.87 (m, 1H), 5.62-5.44 (m, 2H), 5.34 (dd, J=17.2, 1.4 Hz, 1H), 5.23 (dd, J=10.4, 1.2 Hz, 1H), 4.88 (qd, J=9.5, 4.5 Hz, 2H), 4.67-4.57 (m, 2H), 4.50-4.25 (m, 8H), 4.22 (t, J=6.3 Hz, 2H), 3.82 (s, 3H), 3.76 (s, 3H), 3.00-2.85 (m, 2H), 2.58-2.47 (m, 2H), 2.37 (p, J=6.1 Hz, 2H), 2.06 (s, 6H), 1.81-1.73 (m, 6H).

Part (ii)

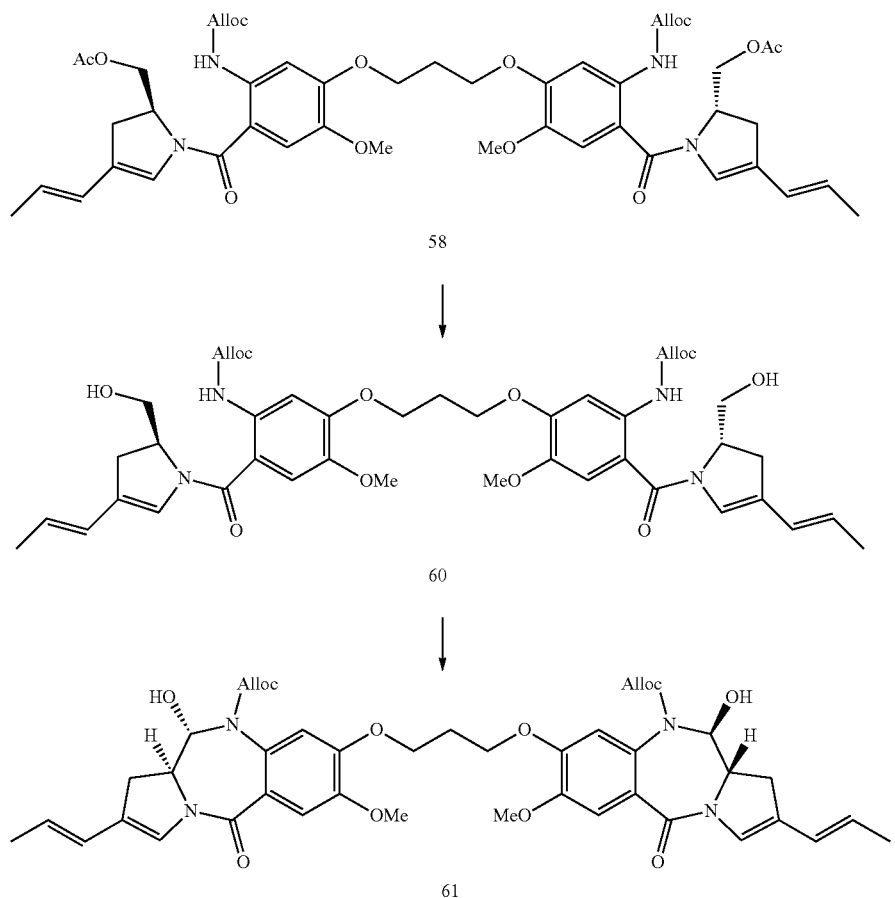

(a) Diallyl ((S,E)-(propane-1,3-diylbis(oxy))bis(2-((S)-2-(hydroxymethyl)-4-((E)-prop-1-en-1-yl)-2,3-dihydro-1H-pyrrole-1-carbonyl)-4-methoxy-5,1-phenylene))dicarbamate (60)

An aqueous solution of potassium carbonate (10 equivalents in 6.6 mL) was added to a solution of acetate 58 in methanol (40 mL). LC/MS and TLC revealed that the reaction was complete after 1 hour. The reaction mixture was washed sequentially with dichloromethane, water, citric acid (0.5 N) and brine. The organic layer was dried over magnesium sulphate. The product mixture was subjected to column chromatography (silica gel; gradient 80% ethyl acetate/20% hexane to 90% ethyl acetate/10% hexane). Pure fractions were combined and removal of excess eluent afforded compound 60 (66 mg, 79% yield) LC/MS 3.35 mins, ES$^+$ 816.88. $^1$H NMR (400 MHz, CDCl$_3$) δ 8.57 (s, 2H), 7.76 (s, 2H), 6.82 (s, 2H), 6.36 (s, 2H), 6.10 (d, J=15.3 Hz, 2H), 5.97 (ddt, J=17.2, 10.5, 5.7 Hz, 2H), 5.59 (dq, J=13.6, 6.8 Hz, 2H), 5.36 (dq, J=17.2, 1.5 Hz, 2H), 5.26 (ddd, J=10.5, 2.5, 1.2 Hz, 2H), 4.78 (td, J=10.4, 4.5 Hz, 2H), 4.64 (dt, J=5.7, 1.4 Hz, 4H), 4.43 (s, 2H), 4.32 (t, J=6.0 Hz, 4H), 3.92-3.74 (m, J=8.0 Hz, 10H), 3.03 (dd, J=15.8, 10.8 Hz, 2H), 2.47-2.37 (m, 4H), 1.81 (dd, J=6.7, 1.0 Hz, 6H).

(b) 1S,11aS,11'S,11a'S, E)-diallyl 8,8'-(propane-1,3-diylbis(oxy))bis(11-hydroxy-7-methoxy-5-oxo-2-((E)-prop-1-en-1-yl)-11,11a-dihydro-pyrrolo[2,1-c][1,4]diazepine-10(5H)-carboxylate) (61)

Dess-Martin periodinane (57 mg, 0.13 mmol, 2.2 eq.) was added in one portion to a solution of the bis-alloc (60) (50 mg, 0.061 mmol, 1 eq.) and anhydrous pyridine (31 mg, 32 µL 0.31 mmol, 5 eq.) in anhydrous DCM (2 mL) under an argon atmosphere at room temperature. The reaction mixture was allowed to stir at room temperature for 20 minutes. The reaction mixture was then diluted with DCM and washed with aq. Na$_2$S$_5$O$_2$ (50 mL), sat. NaHCO$_3$ (50 mL), water (50 mL), brine (50 mL) and dried (MgSO$_4$). DCM was removed by rotary evaporation under reduced pressure. The residue was dissolved in anhydrous DCM (4 mL) and treated with a catalytic amount of DMAP (0.75 mg, 0.0061 mmol, 0.1 eq.) and stirred at room temperature for 2 hours. DCM was removed by rotary evaporation under reduced pressure to give the crude product. Flash chromatography [gradient elution 1:3 n-hexane/ethylacetate] furnished the pure cyclised product as a white solid (2) (3.3 mg, 7%). $^1$H NMR (400 MHz, CD$_3$OD). δ 7.25 (s, 2H) 6.90 (s, 2H), 6.72-6.78 (m, 2H), 6.24-6.28 (d, 2H), 5.72-5.83 (m, 4H), 5.53-5.62 (m, 2H), 5.11-5.20 (m, 4H), 4.62-4.67 (m, 2H), 4.42-4.48 (m, 6H), 3.81-3.92 (m, 10H), 3.07-3.13 dd, 2H), 2.79-2.82 (d, 2H), 2.32-2.38 (m, 2H), 1.83-1.85 (d, 6H OCH$_3$). Analytical Data: RT 6.65 min; MS (ES$^-$) 811.

Part (iii)
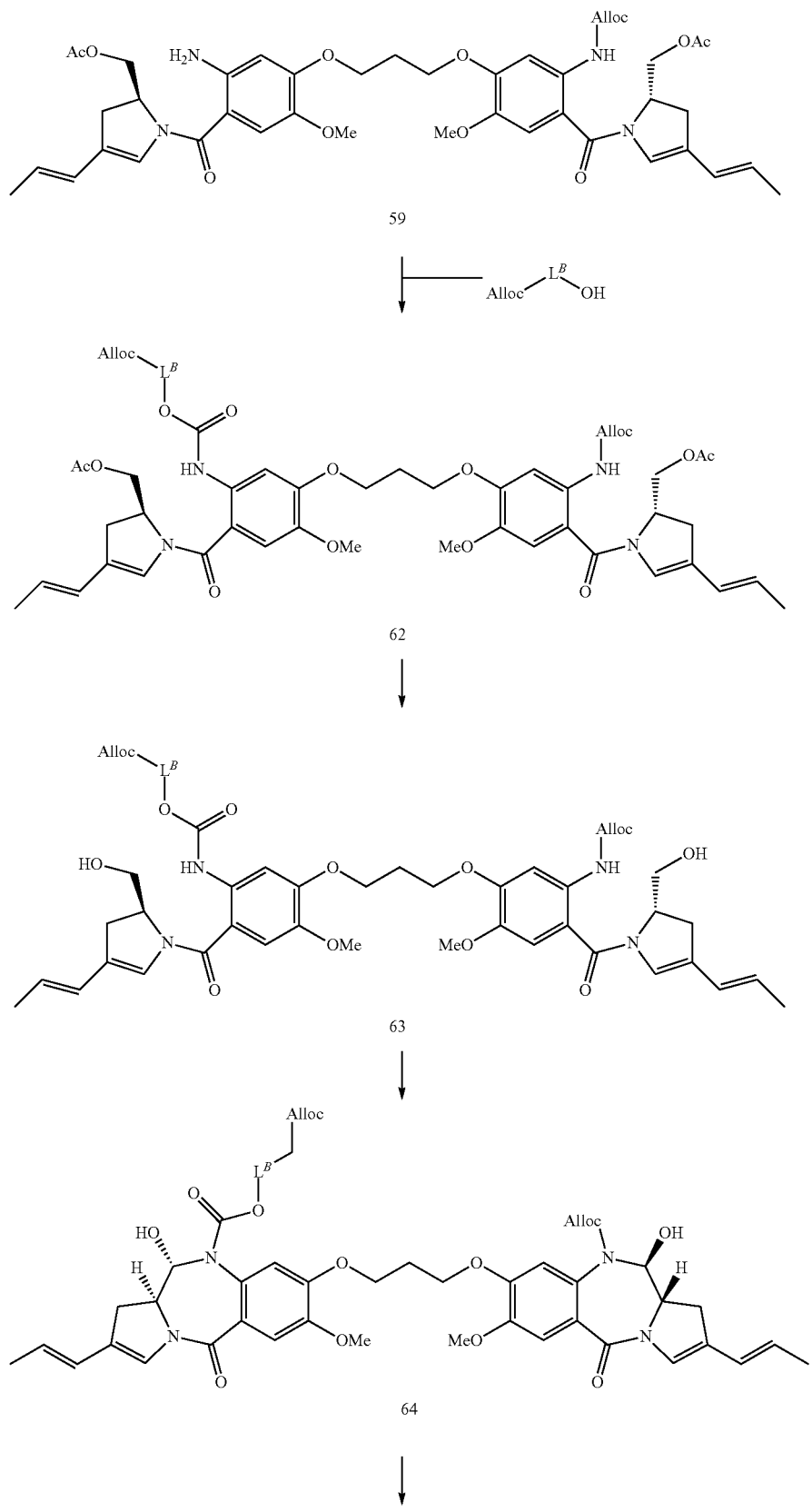

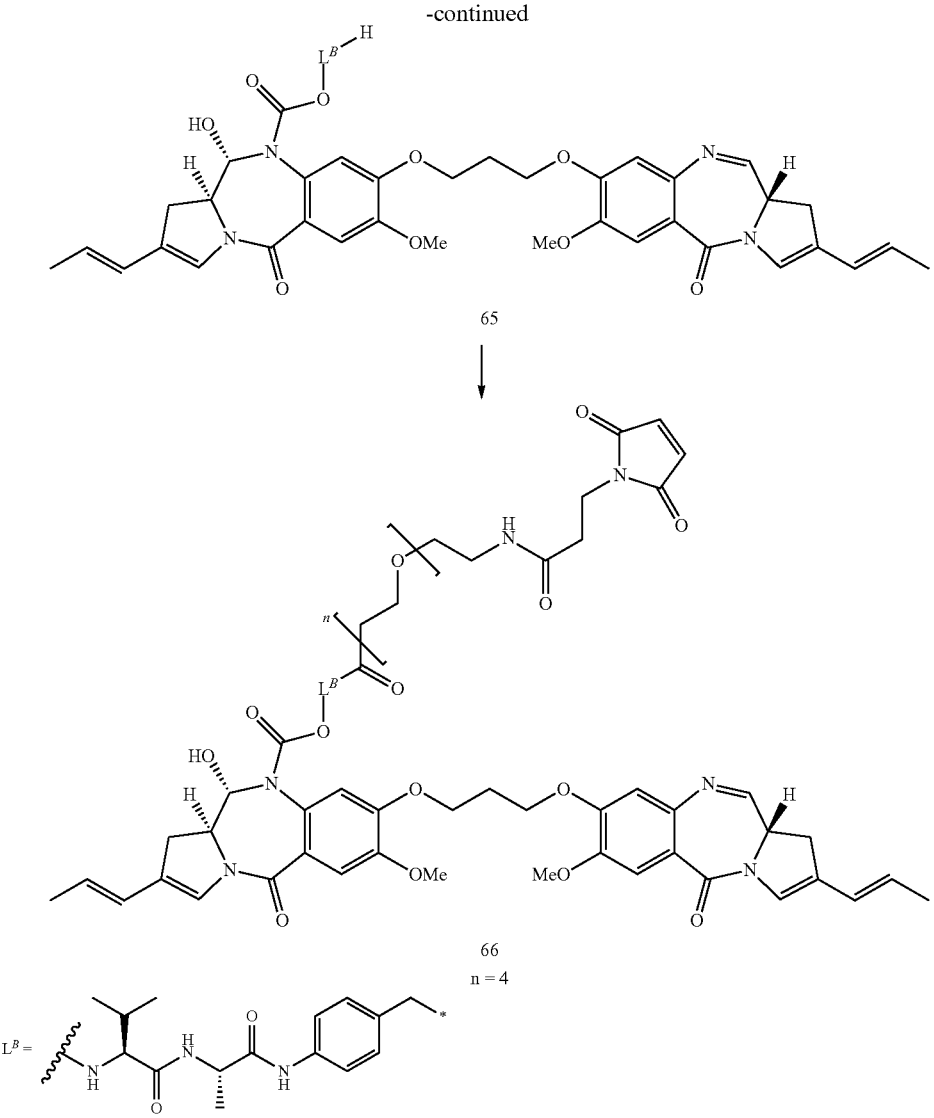

(a) ((2S)-1-(4-(3-(4-(((S)-2-(acetoxymethyl)-4-((E)-prop-1-en-1-yl)-2,3-dihydro-1H-pyrrole-1-carbonyl)-5-(((((4-(2-(2-(((allyloxy)carbonyl)amino)-3-methylbutanamido)propanamido)benzyl)oxy)carbonyl)amino)-2-methoxyphenoxy)propoxy)-2-(((allyloxy)carbonyl)amino)-5-methoxybenzoyl)-4-((E)-prop-1-en-1-yl)-2,3-dihydro-1H-pyrrol-2-yl)methyl acetate (62)

Dry triethylamine (0.206 mL) was added to a stirred solution of the mono-alloc protected bis-aniline 59 (560 mg) and triphosgene (72 mg) in dry tetrahydrofuran (20 mL) under an inert atmosphere. The reaction mixture was heated at 40° C. and a sample was removed and treated with methanol. LC/MS revealed complete conversion to the methyl carbamate indicating that the free amine group had been successfully converted to the reactive isocyanate intermediate. A solution of the alloc-val-ala-PABOH (381 mg) and triethylamine (0.14 mL) in dry tetrahydrofuran (20 mL) was rapidly injected into the reaction vessel at 40° C. The reaction mixture was allowed to stir at room temperature over night after which time a sample was removed and treated with methanol. LC/MS revealed no trace of methyl carbamate indicating that all the isocyanate had been consumed. The reaction mixture was evaporated to dryness to afford the crude product which was purified by column chromatography (silica gel; gradient chloroform to 2% methanol/98% chloroform). Pure fractions were collected and combined and removal of excess eluent by rotary evaporation under reduces pressure afforded the pure product 62 (691 mg, 84% yield). LC/MS 3.73 mins, ES$^+$ 1220.21.

(b) Allyl 4-(2-(2-(((allyloxy)carbonyl)amino)-3-methylbutanamido)propanamido)benzyl ((S,E)-(propane-1,3-diylbis(oxy))bis(2-((S)-2-(hydroxymethyl)-4-((E)-prop-1-en-1-yl)-2,3-dihydro-1H-pyrrole-1-carbonyl)-4-methoxy-5,1-phenyleneDdicarbamate (63)

An aqueous solution of potassium carbonate (770 mg in 4.8 mL water) was added to a solution of the bis-acetate 62 (680 mg) in methanol (29 mL) at room temperature. The deacetylation was complete within 30 minutes as monitored by LC/MS. The reaction mixture was diluted with dichloromethane (200 mL) and the organic phase washed sequentially with citric acid (0.5 N, 100 mL), water (200 mL) and brine (100 mL). The organic phase was dried over magnesium sulphate, the suspension was filtered (vacuum filtration) and excess solvent removed by rotary evaporation under reduced pressure. The residue was subjected to column chromatography (silica gel; gradient 1.5% methanol/98.5% chloroform to 3.5% methanol 96.5% chloroform). Pure fractions were combined and removal of excess eluent by rotary evaporation under reduced pressure afforded the diol 63 (530 mg, 84% yield). LC/MS 3.40 mins, ES⁺ 1136.49.

(c) (11S,11aS)-allyl 8-(3-(((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-5-oxo-2-((E)-prop-1-en-1-yl)-5,10,11,11a-tetrahydro-pyrrolo[2,1-c][1,4]benzodiazepin-8-yl)oxy)propoxy)-11-hydroxy-7-methoxy-5-oxo-2-((E)-prop-1-en-1-yl)-11,11a-dihydro-pyrrolo[2,1-c][1,4]benzodiazepine-10(5H)-carboxylate (64)

Dess-Martin periodinane (373 mg, 4 eq.) was added in one portion to a solution of 63 (250 mg) and pyridine (0.36 mL, 20 eq.) in dry dichloromethane (10 mL) at room temperature. Close monitoring by TLC (5% methanol/chloroform) revealed the disappearance of starting material after 30 minutes. The reaction was worked up with a solution of sodium metabisulphite and sodium hydrogen carbonate, followed by brine. The dichloromethane layer was dried over magnesium sulphate and vacuum filtered. The dichloromethane solution was then treated with a catalytic amount of DMAP (c. 10 mg), causing the main product spot to coalesce into one as observed by TLC/LC/MS. The solution was filtered and the dichloromethane removed by rotary evaporation under reduced pressure. The resulting residue was subjected to column chromatography (silica gel; gradient 1.5% methanol/98.5% chloroform to 3% methanol/97% chloroform). Pure fractions were collected and removal of eluent by rotary evaporation under reduced pressure afforded the desired cyclised product 64 (62 mg, 25% yield). LC/MS 3.35 mins, ES⁺ 1132.19, ES⁻ 1130.25.

(d) (11S,11aS)-4-(S)-2-(S)-2-amino-3-methylbutanamido)propanamido)benzyl 11-hydroxy-7-methoxy-8-(3-(((S)-7-methoxy-5-oxo-2-((E)-prop-1-en-1-yl)-5,11a-dihydro-pyrrolo[2,1-c][1,4]benzodiazepin-8-yl)oxy)propoxy)-5-oxo-2-((E)-prop-1-en-1-yl)-11,11a-dihydro-pyrrolo[2,1-c][1,4]benzodiazepine-10(5H)-carboxylate (65)

Pd(PPh₃)₄ (1.9 mg) was added to a solution of the alloc compound (64) (62 mg) and pyrrolidine (22.6 µL) in dry DCM (3 mL) under an argon atmosphere. The solution was stirred at room temperature for 1.5 hours. The solvent was evaporated under reduced pressure. Purification by flash column chromatography [gradient elution 3% methanol/97% chloroform to 90% chloroform/10% methanol] gave the product as a white powder (26 mg, 50%). LC/MS: RT 2.70 min MS (ES⁺) 946.17.

(e) (11S,11aS)-4-((2S,5S)-25-(2,5-dioxo-2,5-dihydro-1H-pyrrol-1-yl)-5-isopropyl-2-methyl-4,7,23-trioxo-10,13,16,19-tetraoxa-3,6,22-triazapentacosanamido)benzyl 11-hydroxy-7-methoxy-8-(3-(((S)-7-methoxy-5-oxo-2-((E)-prop-1-en-1-yl)-5,11a-dihydro-pyrrolo[2,1-c][1,4]benzodiazepin-8-yl)oxy)propoxy)-5-oxo-2-((E)-prop-1-en-1-yl)-11,11a-dihydro-pyrrolo[2,1-c][1,4]benzodiazepine-10(5H)-carboxylate (66)

A solution of N,N-diisopropyldiethylamine i (2.6 µL) was added to a solution of amine dipeptide 65 (13 mg) and maleimide-dPeg®4—NHS ester (8.5 mg), in dry DCM (4 mL) The solution was stirred at room temperature for 24 h. The reaction mixture was evaporated under reduced pressure and the residue subjected to semi-preparative TLC (10% methanol/90% chloroform) to afford a pure sample of the desired maleimide 66. LC-MS retention time 2.87 min ES⁺ 1344.29.

The invention claimed is:
1. A compound of formula I:

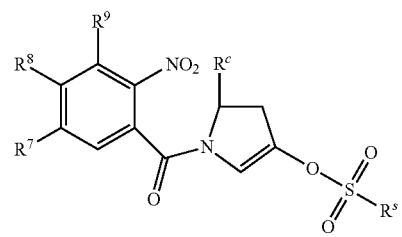

wherein:
R⁷ and R⁸ are independently selected from: OR^A, where R^A is selected from $C_{1-4}$ saturated alkyl, optionally substituted by phenyl, which may bear a chloro substituent, pyridyl and furanyl; chloro; NH₂; —CH₂—O—C(=O)Me;
or R⁷ and R⁸ together form a group —O—(CH₂)$_m$—O—, where m is 1 or 2;
or the compound is a dimer with each monomer independently being of formula (I), where the R⁷ groups or R⁸ groups of each monomer form together a dimer bridge having the formula —X—R"—X— linking the monomers, where R" is a $C_{3-12}$ saturated alkylene group, which group may be interrupted by O, S, NH, NMe, phenylene or pyridylene, where the phenylene and pyridylene groups are optionally substituted by NH₂, and each X is independently selected from O, S, or NH;
R⁹ is selected from H, methyl and methoxy;
R^s is selected from CF₃, (CF₂)₃CF₃, CH₃ and

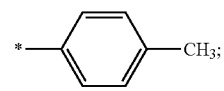 [SMILES: *c1ccc(C)cc1]

and
R^C is selected:
(i) —C(=O)—OR^{c1}, where R^{c1} is a saturated $C_{1-4}$ alkyl group;
(ii) —CH₂—O—C(=O)R^{c2}, where R^{c2} is methyl or phenyl;

103

(iii) —CH$_2$—O—Si—(R$^{Si1}$)(R$^{Si2}$)(R$^{Si3}$) where R$^{Si1}$, R$^{Si2}$, R$^{Si3}$ are independently selected from C$_{1-6}$ a saturated alkyl group and a phenyl group; and (iv) —C(—YR$^{C3}$)(—YR$^{C4}$) where each Y is independently O or S, and where R$^{C3}$ and R$^{C4}$ are independently a saturated C$_{1-4}$ alkyl group, or together form a C$_{2-3}$ alkylene, which is substantially free of any of the corresponding compound of formula IB:

IB

2. A compound according to claim 1, wherein R$^7$ and R$^8$ are independently OR$^A$, where R$^A$ is selected from C$_{1-4}$ saturated alkyl, optionally substituted by phenyl, pyridyl and furanyl.

3. A compound according to claim 1, wherein R$^A$ is unsubstituted C$_{1-4}$ saturated alkyl.

4. A compound according to claim 3, wherein R$^A$ is methyl.

5. A compound according to claim 1 which is a dimer, where each X is O.

6. A compound according to claim 1 which is a dimer, where R" is a C$_3$, C$_5$ or C$_7$ saturated alkylene group.

7. A compound according to claim 1, wherein R$^S$ is CF$_3$.

8. A compound according to claim 1, wherein R$^{C1}$ is methyl.

9. A compound according to claim 1, wherein —Si—(R$^{Si1}$)(R$^{Si2}$)(R$^{Si3}$) is TBDMS.

10. A method of synthesising a compound of formula I:

I as defined in claim 1, from a compound of formula II:

II comprising treating II with the appropriate anhydride and anhydrous 2,6-lutidine or anhydrous 2,6-tBu-pyridine at a temperature of –35° C. or lower in a dry organic solvent under a inert atmosphere.

104

11. The method according to claim 10, wherein the reaction is carried out at a temperature of –40° C. or lower.

12. A compound of formula III:

III wherein:

R$^7$ and R$^8$ are independently selected from: OR$^A$, where R$^A$ is selected from C$_{1-4}$ saturated alkyl, optionally substituted by phenyl, which may bear a chloro substituent, pyridyl and furanyl; chloro; NH$_2$; —CH$_2$—O—C(=O)Me;

or R$^7$ and R$^8$ together form a group —O—(CH$_2$)$_m$—O—, where m is 1 or 2;

or the compound is a dimer with each monomer independently being of formula (III), where the R$^7$ groups or R$^8$ groups of each monomer form together a dimer bridge having the formula —X—R"—X— linking the monomers, where R" is a C$_{3-12}$ saturated alkylene group, which group may be interrupted by O, S, NH, NMe, phenylene or pyridylene, where the phenylene and pyridylene groups are optionally substituted by NH$_2$, and each X is independently selected from O, S, or NH;

R$^9$ is selected from H, methyl and methoxy;

R$^c$ is selected from:

(i) —C(=O)—OR$^{c1}$, where R$^{c1}$ is a saturated C$_{1-4}$ alkyl group;

(ii) —CH$_2$—O—C(=O)R$^{C2}$, where R$^{C2}$ is methyl or phenyl;

(iii) —CH$_2$—O—Si—(R$^{Si1}$)(R$^{Si2}$)(R$^{Si3}$), where R$^{Si1}$, R$^{Si2}$, R$^{Si3}$, are independently selected from C$_{1-6}$ a saturated alkyl group and a phenyl group; and (iv) —C(—YR$^{C3}$)(—YR$^{C4}$) where each Y is independently O or S, and where R$^{C3}$ and R$^{C4}$ are independently a saturated C$_{1-4}$ alkyl group or together form a C$_{2-3}$ alkylene; and R$^2$ is selected from:

(i) an optionally substituted C$_{5-20}$ aryl group wherein the optional substituents are chosen from halo, C$_{1-7}$ alkoxy, di-C$_{1-4}$ alkylamino-C$_{1-7}$ alkoxy, C$_{1-7}$ alkyl, bis-ox-alkylene and N—C$_{1-4}$ alkyl piperazinyl; and (ii) an optionally substituted C$_{2-5}$ alkenyl group or C$_{2-5}$ alkynyl group, wherein the optional substituents are chosen from:

(i) optionally substituted C$_{5-20}$ aryl groups wherein the optional substituents are chosen from halo, C$_{1-7}$ alkoxy, di-C$_{1-4}$ alkylamino-C$_{1-7}$ alkoxy, C$_{1-7}$ alkyl, bis-oxy-alkylene and N—C$_{1-4}$ alkyl piperazinyl;

(ii) —CN;

(iii) —C(=O)—NR$^{N1}$R$^{N2}$, where R$^{N1}$ and R$^{N2}$ are C$_{1-7}$ alkyl groups;

(iv) —C(=O)—OR$^O$, where R$^O$ is a C$_{1-7}$ alkyl group;

(v) —OR$^O$;

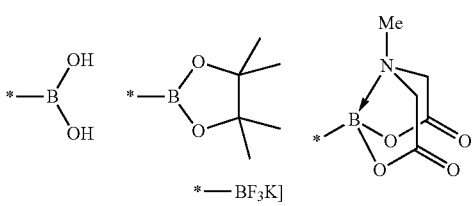

(vi) —Sn(R$^{SN}$)$_3$ where R$^{SN}$ is a C$_{1-7}$ alkyl group; and
wherein at least one of the unsaturated bonds is conjugated to the double bond present between C2 and C3; which is substantially free of any of the corresponding compound of formula IIIB:

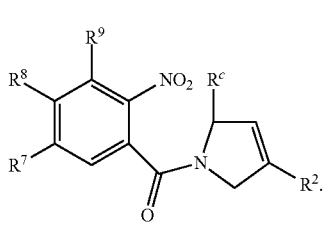

IIIB

13. A method of synthesising a compound of formula III:

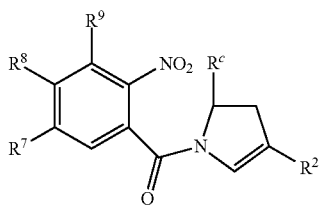

III wherein:
R$^7$ and R$^8$ are independently selected from: OR$^A$, where R$^A$ is selected from C$_{1-4}$ saturated alkyl, optionally substituted by phenyl, which may bear a chloro substituent, pyridyl and furanyl; chloro; NH$_2$; —CH$_2$—O—C(=O)Me;
or R$^7$ and R$^8$ together form a group —O—(CH$_2$)$_m$—O—, where m is 1 or 2;
or the compound is a dimer with each monomer independently being of formula (III), where the R$^7$ groups or R$^8$ groups of each monomer form together a dimer bridge having the formula —X—R"—X— linking the monomers where R" is a C$_{3-12}$ saturated alkylene group, which group may be interrupted by O, S, NH, NMe, phenylene or pyridylene, where the phenylene and pyridylene groups are optionally substituted by NH$_2$, and each X is independently selected from O, S, or NH; R$^9$ is selected from H, methyl and methoxy;
R$^C$ is selected from:
(i) —C(=O)—OR$^{C1}$, where R$^{C1}$ is a saturated C$_{1-4}$ alkyl group;
(ii) —CH$_2$—O—C(=O)R$^{C2}$, where R$^{C2}$ is methyl or phenyl;
(iii) —CH$_2$—O—Si—(R$^{Si1}$)(R$^{Si2}$)(R$^{Si3}$), where $^{Si1}$, R$^{Si2}$, R$^{Si3}$ are independently selected from C$_{1-6}$ a saturated alkyl group and a phenyl group; and (iv) —C(—YR$^{C3}$)(—YR$^{C4}$) where each Y is independently O or S, and where R$^{C3}$ and R$^{C4}$ are independently a saturated C$_{1-4}$ alkyl group, or together form a C$_{2-3}$ alkylene; and
R$^2$ is selected from:
(i) an optionall substituted C$_{5-20}$ aryl group wherein the optional substituents are chosen from halo, C$_{1-7}$ alkoxy, di-C$_{1-4}$ alkylamino-C$_{1-7}$ alkoxy, C$_{1-7}$ alkyl, bis-oxy-alkylene and N—C$_{1-4}$ alkyl piperazinyl; and
(ii) an optionally substituted C$_{2-5}$ alkenyl group or C$_{2-5}$ alkynyl group, wherein the optional substituents are chosen from:
(i) optionally substituted C$_{5-20}$ aryl groups wherein the optional substituents are chosen from halo, C$_{1-7}$ alkoxy, di-C$_{1-4}$ alkylamino-C$_{1-7}$ alkoxy, C$_{1-7}$ alkyl, bis-oxy-alkylene and N—C$_{1-4}$ alkyl piperazinyl;
(ii) —CN;
(iii) —C(=O)—NR$^{N1}$R$^{N2}$ where R$^{N1}$ and R$^{N2}$ are C$_{1-7}$ alkly groups;
(iv) —C(=O)—OR$^O$ is a C$_{1-7}$ alkyl group;
(v) —OR$^O$;

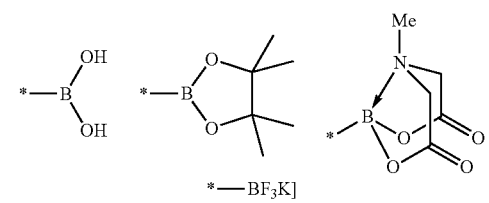

(vi) —Sn(R$^{SN}$)$_3$ where R$^{SN}$ is a C$_{1-7}$ alkyl group;
from a compound of formula I:

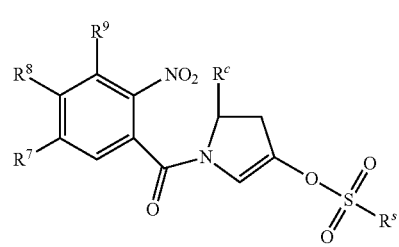

I wherein:
R$^S$ is selected from CF$_3$, (CF$_2$)$_3$CF$_3$, CH$_3$ and

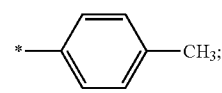 [SMILES: *c1ccc(C)cc1]

and
comprising one of the following:
(i) a Suzuki coupling between a compound of formula I and an appropriate aryl boron derivative;
(ii) a Heck coupling with an appropriate alkene, acrylamide or acrylate;
(iii) a Stille coupling with an appropriate organotin reagent;

(iv) a Sonagishira coupling with an appropriate alkyne; or
(v) a hydride transfer using a triethylsilane, wherein the compound of formula I is synthesised from a compound of formula II:

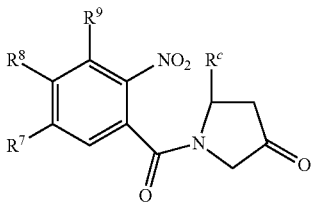

comprising treating II with the appropriate anhydride and anhydrous 2,6-lutidine or anhydrous 2,6-tBu-pyridine at a temperature of −35° C. or lower in a dry organic solvent under a inert atmosphere.

14. A compound of formula IV:

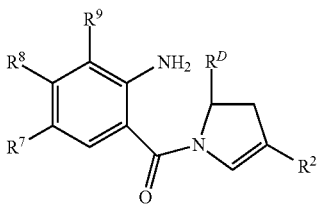

wherein $R^7$ and $R^8$ are independently selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
  or $R^7$ and $R^8$ together form a group —O—$(CH_2)_m$—O—, where m is 1 or 2;
  or the compound is a dimer with each monomer independently being of formula (IV), where the $R^7$ groups or $R^8$ groups of each monomer form together a dimer bridge having the formula —X—R"—X— linking the monomers, where R" is a $C_{3-12}$ saturated alkylene group, which group may be interrupted by O, S, NH, NMe, phenylene or pyridylene, where the phenylene and pyridylene groups are optionally substituted by $NH_2$, and each X is independently selected from O, S, or NH;
$R^9$ is selected from H, methyl and methoxy;
$R^2$ is selected from:
(i) an optionally substituted $C_{5-20}$ aryl group wherein the optional substituents are chosen from halo, $C_{1-7}$ alkoxy, di-$C_{1-4}$ alkylamino-$C_{1-7}$ alkoxy, $C_{1-7}$ alkyl, bis-oxy-alkylene and N—$C_{1-4}$ alkyl piperazinyl;
and
(ii) an optionally substituted $C_{2-5}$ alkenyl group or $C_{2-5}$ alkynyl group, wherein the optional substituents are chosen from:
  (i) optionally substituted $C_{5-20}$ aryl groups wherein the optional substituents are chosen from halo, $C_{1-7}$ alkoxy, di-$C_{1-4}$ alkylamino-$C_{1-7}$ alkoxy, $C_{1-7}$ alkyl, bis-oxy-alkylene and N—$C_{1-4}$ alkyl piperazinyl;
  (ii) —CN;
  (iii) —C(=O)—$NR^{N1}R^{N2}$ where $R^{N1}$ and $R^{N2}$ are $C_{1-7}$ alkly groups;
  (iv) —C(=O)—$OR^O$ is a $C_{1-7}$ alkyl group;
  (v) —$OR^O$;

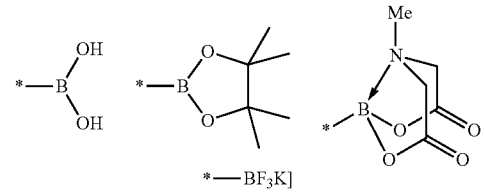

(vi) —Sn$(R^{SN})_3$ where $R^{SN}$ is a $C_{1-7}$ alkyl group; and
$R^D$ is selected from:
  (ii) —$CH_2$—O—C(=O)$R^{C2}$, where $R^{C2}$ is methyl or phenyl;
  (iii) —$CH_2$—O—Si—$(R^{Si1})(R^{Si2})(R^{Si3})$, where $R^{Si1}$, $R^{Si2}$, $R^{Si3}$ are independently selected from $C_{1-6}$ saturated alkyl group and a phenyl group; and
  (iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene,
  which is substantially free of any of the corresponding compound of formula IVB:

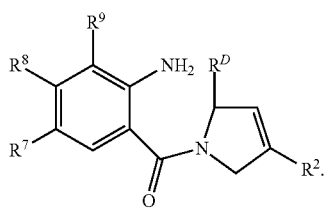

15. A compound according to claim 14, wherein —Si—$(R^{Si1})(R^{Si2})(R^{Si3})$ is TBDMS.
16. A compound according to claim 14, wherein $R^{C2}$ is methyl.
17. A method of synthesising a compound of formula IV:

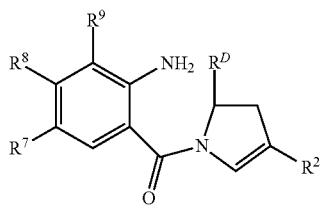

wherein $R^7$ and $R^8$ are independently selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
  or $R^7$ and $R^8$ together form a group —O—$(CH_2)_m$—O—, where m is 1 or 2;
  or the compound is a dimer with each monomer independently being of formula (IV), where the $R^7$ groups or $R^8$ groups of each monomer form together a dimer bridge having the formula —X—R"—X— linking the monomers, where R" is a $C_{3-12}$ saturated alkylene group, which group may be interrupted by O, S, NH, NMe, phenylene or pyridylene, where the phenylene and pyridylene groups are optionally substituted by $NH_2$, and each X is independently selected from O, S, or NH;
$R^9$ is selected from H, methyl and methoxy;
$R^c$ is selected from:
(i) an optionally substituted $C_{5-20}$ aryl group wherein the optional substituents are chosen from halo, $C_{1-7}$ alkoxy, di-$C_{1-4}$ alkylamino-$C_{1-7}$ alkoxy, $C_{1-7}$ alkyl, bis-ox-alkylene and N—$C_{1-4}$ alkyl piperazinyl; and
(ii) an optionally substituted $C_{2-5}$ alkenyl group or $C_{2-5}$ alkynyl group, wherein the optional substituents are chosen from:
(i) optionally substituted $C_{5-20}$ aryl groups wherein the optional substituents are chosen from halo, $C_{1-7}$ alkoxy, di-$C_{1-4}$ alkylamino-$C_{1-7}$ alkoxy, $C_{1-7}$ alkyl, bis-oxy-alkylene and N—$C_{1-4}$ alkyl piperazinyl;
(ii) —CN;
(iii) —C(=O)—$NR^{N1}R^{N2}$, where $R^{N1}$ and $R^{N2}$ are $C_{1-7}$ alkyl groups;
(iv) —C(=O)—$OR^O$, where $R^O$ is a $C_{1-7}$ alkyl group;
(v) —$OR^O$;

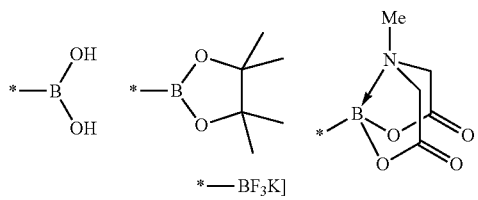

—Sn($R^{SN}$)$_3$ where $R^{SN}$ is a $C_{1-7}$ alkyl group; and
$R^D$ is selected from:
(ii) —$CH_2$—O—C(=O)$R^{C2}$, where $R^{C2}$ is methyl or phenyl;
(iii) —$CH_2$—O—Si—($R^{Si1}$)($R^{Si2}$)($R^{Si3}$), where $R^{Si1}$, $R^{Si2}$, $R^{Si3}$ are independently selected from $C_{1-6}$ saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene, from a compound of formula III:

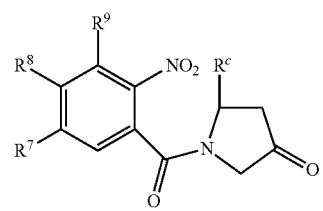

wherein:
$R^C$ is selected from:
(i) —C(=O)—$OR^{C1}$, where $R^{C1}$ is a saturated $C_{1-4}$ alkyl group;
(ii) —$CH_2$—O—C(=O)$R^{C2}$, where $R^{C2}$ is methyl or phenyl;
(iii) —$CH_2$—O—Si—($R^{Si1}$)($R^{Si2}$)($R^{Si3}$), where $^{Si1}$, $R^{Si2}$, $R^{Si3}$ are independently selected from $C_{1-6}$ a saturated alkyl group and a phenyl group; and
(iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene; and by one of the following:
(i) if $R^C$ is —C(=O)—$OR^{C1}$, conversion of —C(=O)—$OR^{C1}$ to —$CH_2$—O—C(=O)$R^{C2}$ or —$CH_2$—O—Si—($R^{Si1}$)($R^{Si2}$)($R^{Si3}$), followed by:
(ii) if $R^C$ is —$CH_2$—O—C(=O)$R^{C2}$, reduction of the nitro group by zinc in acetic acid or if $R^C$ is —$CH_2$—O—Si—($R^{Si1}$)($R^{Si2}$)($R^{Si3}$), reduction of the nitro group using zinc in 5% formic acid in ethanol;
(iii) if $R^C$ is —C(—$YR^{C3}$)(—$YR^{C4}$), reduction of the nitro group using Cd/Pb couple, sodium dithionite or tin II chloride, wherein the compound of formula III is synthesised from a compound of formula II:

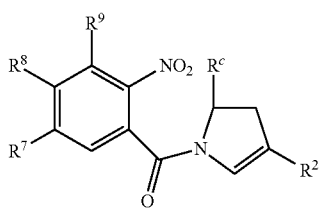

comprising treating II with the appropriate anhydride and anhydrous 2,6-lutidine or anhydrous 2,6-tBu-pyridine at a temperature of –35° C. or lower in a dry organic solvent under a inert atmosphere.

18. A compound of formula V:

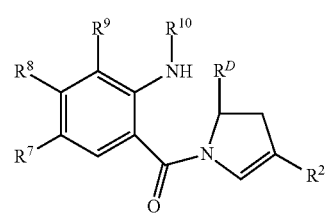

wherein $R^7$ and $R^8$ are independently selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;
or $R^7$ and $R^8$ together form a group —O—$(CH_2)_m$—O—, where m is 1 or 2;
or the compound is a dimer with each monomer independently being of formula (V), where the $R^7$ groups or $R^8$ groups of each monomer form together a dimer bridge having the formula —X—R"—X— linking the monomers, where R" is a $C_{3-12}$ saturated alkylene group, which group may be interrupted by O, S, NH, NMe, phenylene or pyridylene, where the phenylene and pyridylene groups are optionally substituted by $NH_2$, and each X is independently selected from O, S, or NH;
$R^9$ is selected from H, methyl and methoxy;
$R^2$ is selected from:
(i) an optionally substituted $C_{5-20}$ aryl group wherein the optional substituents are chosen from halo, $C_{1-7}$ alkoxy, di-$C_{1-4}$ alkylamino-$C_{1-7}$ alkoxy, $C_{1-7}$ alkyl, bis-ox-alkylene and N—$C_{1-4}$ alkyl piperazinyl; and
(ii) an optionally substituted $C_{2-5}$ alkenyl group or $C_{2-5}$ alkynyl group, wherein the optional substituents are chosen from:
(i) optionally substituted $C_{5-20}$ aryl groups wherein the optional substituents are chosen from halo, $C_{1-7}$ alkoxy, di-$C_{1-4}$ alkylamino-$C_{1-7}$ alkoxy, $C_{1-7}$ alkyl, bis-oxy-alkylene and N—$C_{1-4}$ alkyl piperazinyl;

(ii) —CN;

(iii) —C(=O)—NR$^{N1}$R$^{N2}$, where R$^{N1}$ and R$^{N2}$ are $C_{1-7}$ alkyl groups;

(iv) —C(=O)—OR$^O$, where R$^O$ is a $C_{1-7}$ alkyl group;

(v) —OR$^O$;

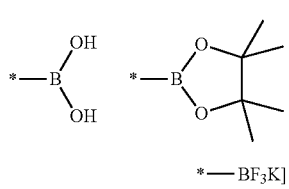

(vi) —Sn(R$^{SN}$)$_3$ where R$^{SN}$ is a $C_{1-7}$ alkyl group; and

R$^D$ is selected from:

(ii) —CH$_2$—O—C(=O)R$^{C2}$, where R$^{C2}$ is methyl or phenyl;

(iii) —CH$_2$—O—Si—(R$^{Si1}$)(R$^{Si2}$)(R$^{Si3}$), where R$^{Si1}$, R$^{Si2}$, R$^{Si3}$ are independently selected from $C_{1-6}$ saturated alkyl group and a phenyl group; and (iv) —C(—YR$^{C3}$)(—YR$^{C4}$) where each Y is independently O or S, and where R$^{C3}$ and R$^{C4}$ are independently a saturated $C_{1-4}$ alkyl group, or together form a $C_{2-3}$ alkylene; and R$^{10}$ is a carbamate-based nitrogen protecting group, which is palladium-labile and/or labile under the conditions used to add the group:

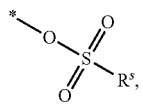

or contains a moiety which is palladium-labile and/or is labile under the conditions used to add the group:

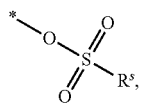

which is substantially free of any of the corresponding compound of formula VB:

VB

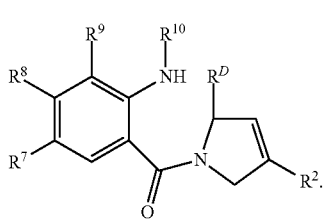

19. A compound according to claim 18, wherein R$^{10}$ is selected from one of:

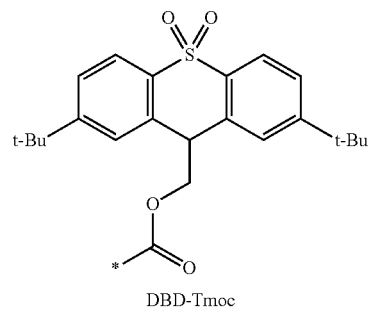

DBD-Tmoc

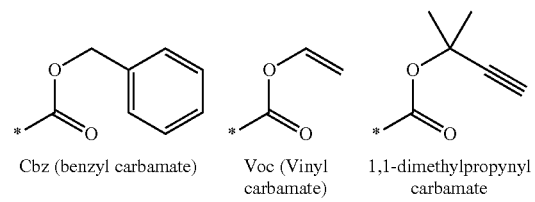

Cbz (benzyl carbamate)   Voc (Vinyl carbamate)   1,1-dimethylpropynyl carbamate

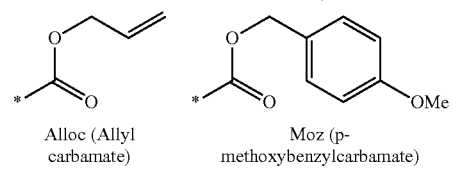

Alloc (Allyl carbamate)   Moz (p-methoxybenzylcarbamate)

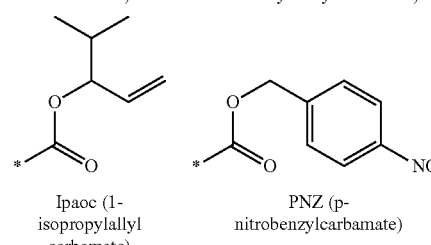

Ipaoc (1-isopropylallyl carbamate)   PNZ (p-nitrobenzylcarbamate)

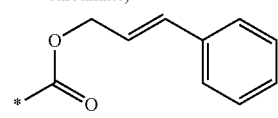

Coc (Cinnamyl carbamate)

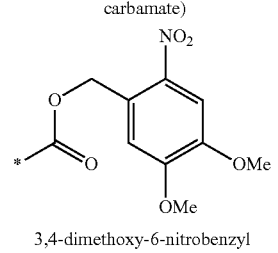

3,4-dimethoxy-6-nitrobenzyl carbamate

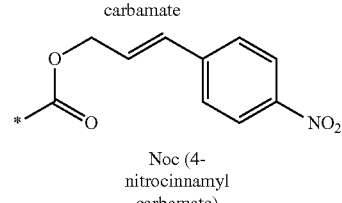

Noc (4-nitrocinnamyl carbamate)

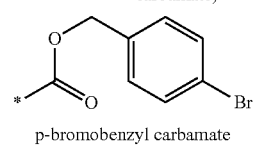

p-bromobenzyl carbamate

-continued

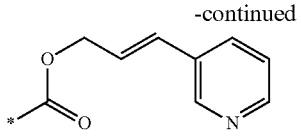
Paloc (3-(3'-pyridyl)prop-2-enyl carbamate)

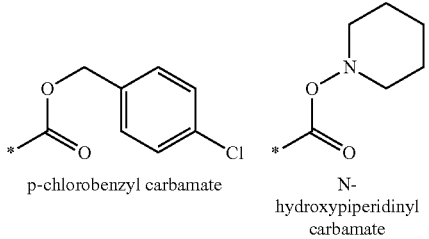 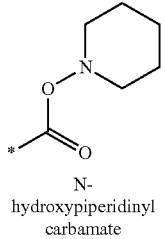
p-chlorobenzyl carbamate     N-hydroxypiperidinyl carbamate

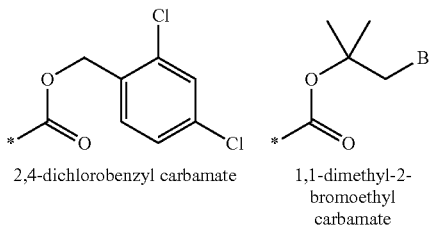 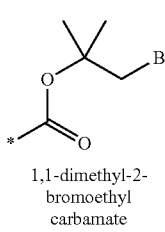
2,4-dichlorobenzyl carbamate     1,1-dimethyl-2-bromoethyl carbamate

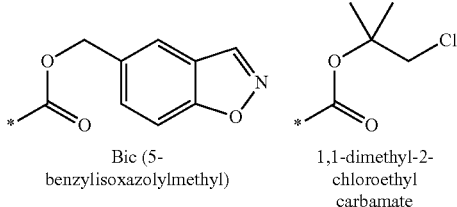 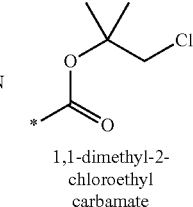
Bic (5-benzylisoxazolylmethyl)     1,1-dimethyl-2-chloroethyl carbamate

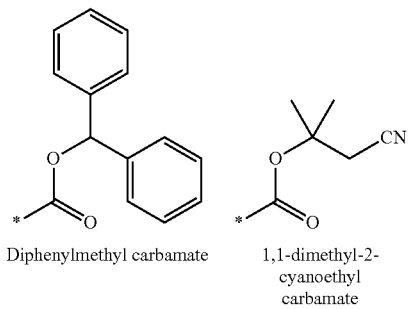 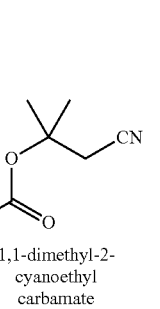
Diphenylmethyl carbamate     1,1-dimethyl-2-cyanoethyl carbamate

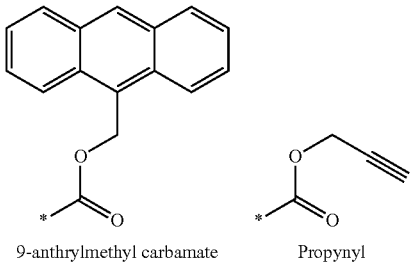 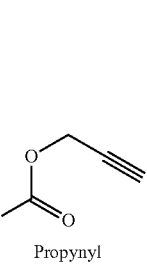
9-anthrylmethyl carbamate     Propynyl carbamate

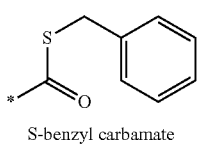
S-benzyl carbamate where the asterisk indicates the point of attachment to the N10 position.

20. A compound according to claim 18, wherein $R^{10}$ is of the formula:

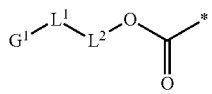

where the asterisk indicates the point of attachment to the N10 position, $G^1$ is a functional group to form a connection to a cell binding agent, $L^1$ is a cleavable linker, $L^2$ is a covalent bond or together with —OC(=O)— forms a self-immolative linker.

21. A method of synthesising a compound of formula V:

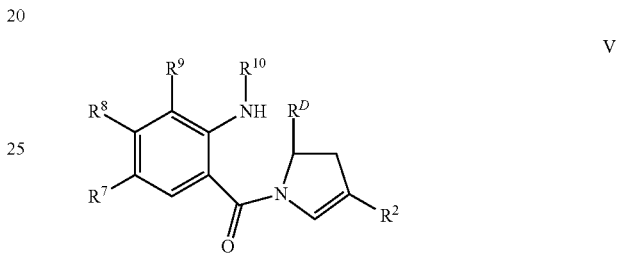

wherein $R^7$ and $R^8$ are independently selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me;

or $R^7$ and $R_8$ together form a group —O—$(CH_2)_m$—O—, where m is 1 or 2;

or the compound is a dimer with each monomer independently being of formula (V), where the $R^7$ groups or $R^8$ groups of each monomer form together a dimer bridge having the formula —X—R"—X— linking the monomers where R" is a $C_{3-12}$ saturated alkylene group, which group may be interrupted by O, S, NH, NMe, phenylene or pyridylene, where the phenylene and pyridylene groups are optionally substituted by $NH_2$, and each X is independently selected from O, S, or NH;

$R^9$ is selected from H, methyl and methoxy;

$R^2$ is selected from:

(i) an optionally substituted $C_{5-20}$ aryl group wherein the optional substituents are chosen from halo, $C_{1-7}$ alkoxy, di-$C_{1-4}$alkylamino-$C_{1-7}$alkoxy, $C_{1-7}$alkyl, bis-oxy-alkylene and N—$C_{1-4}$ alkyl piperazinyl; and (ii) an optionally substituted $C_{2-5}$ alkenyl group or $C_{2-5}$ alkynyl group, wherein the optional substituents are chosen from:

(i) optionally substituted $C_{5-20}$ aryl groups wherein the optional substituents are chosen from halo, $C_{1-7}$ alkoxy, di-$C_{1-4}$ alkylamino-$C_{1-7}$alkoxy, $C_{1-7}$alkyl, bis-oxy-alkylene and N—$C_{1-4}$ alkyl piperazinyl;

(ii) —CN;

(iii) —C(=O)—$NR^{N1}R^{N2}$, where $R^{N1}$ and $R^{N2}$ are $C_{1-7}$ alkyl groups;

(iv) —C(=O)—$OR^O$, where $R^O$ is a $C_{1-7}$ alkyl group;

(v) —OR$^O$;

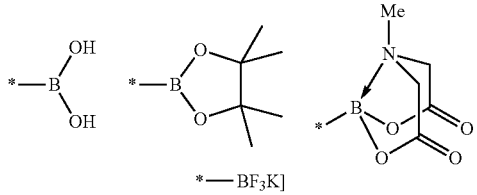

*—BF$_3$K]

(vi) —Sn(R$^{SN}$)$_3$ where R$^{SN}$ is a C$_{1-7}$ alkyl group; and R$^D$ is selected from:
  (ii) —CH$_2$—O—C(=O)R$^{C2}$, where R$^{C2}$ is methyl or phenyl;
  (iii) —CH$_2$—O—Si—(R$^{Si1}$)(R$^{Si2}$)(R$^{Si3}$), where R$^{Si1}$, R$^{Si2}$, R$^{Si3}$ are independently selected from C$_{1-6}$ saturated alkyl group and a phenyl group; and
  (iv) —C(—YR$^{C3}$)(—YR$^{C4}$) where each Y is independently O or S, and where R$^{C3}$ and R$^{C4}$ are independently a saturated C$_{1-4}$ alkyl group, or together form a C$_{2-3}$ alkylene; and R$^{10}$ is a carbamate-based nitrogen protecting group, which is palladium-labile and/or labile under the conditions used to add the group:

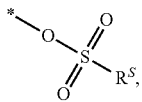

or contains a moiety which is palladium-labile and/or is labile under the conditions used to add the group:

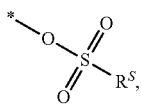

from a compound of formula IV:

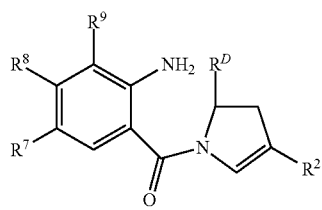

by reaction of IV with triphosgene to obtain the isocyanate followed by reaction with R$^{10}$—OH, wherein the compound of formula IV is synthesised from a compound of formula II:

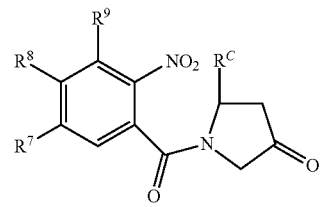

including the method comprising treating II with the appropriate anhydride and anhydrous 2,6-lutidine or anhydrous 2,6-tBu-pyridine at a temperature of −35° C. or lower in a dry organic solvent under a inert atmosphere.

22. A compound of formula VI:

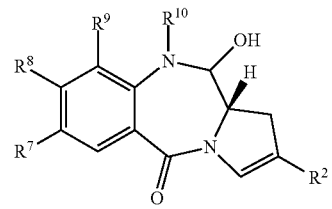

wherein R$^7$ and R$^8$ are independently selected from: OR$^A$, where R$^A$ is selected from C$_{1-4}$ saturated alkyl, optionally substituted by phenyl, which may bear a chloro substituent, pyridyl and furanyl; chloro; NH$_2$; —CH$_2$—O—C(=O)Me;

or R$^7$ and R$_8$ together form a group —O—(CH$_2$)$_m$—O—, where m is 1 or 2;

or the compound is a dimer with each monomer independently being of formula (VI), where the R$^7$ groups or R$^8$ groups of each monomer form together a dimer bridge having the formula —X—R"—X— linking the monomers where R" is a C$_{3-12}$ saturated alk lene rou which group may be interrupted by O, S, NH, NMe, phenylene or pyridylene, where the phenylene and pyridylene groups are optionally substituted by NH$_2$, and each X is independently selected from O, S, or NH;

R$^9$ is selected from H, methyl and methoxy;

R$^2$ is selected from:
  (i) an optionally substituted C$_{5-20}$ aryl group wherein the optional substituents are chosen from halo, C$_{1-7}$ alkoxy, di-C$_{1-4}$alkylamino-C$_{1-7}$alkoxy, C$_{1-7}$alkyl, bis-oxy-alkylene and N—C$_{1-4}$ alkyl piperazinyl; and
  (ii) an optionally substituted C$_{2-5}$ alkenyl group or C$_{2-5}$ alkynyl group, wherein the optional substituents are chosen from:
    (i) optionally substituted C$_{5-20}$ aryl groups wherein the optional substituents are chosen from halo, C$_{1-7}$ alkoxy, di-C$_{1-4}$ alkylamino-C$_{1-7}$alkoxy, C$_{1-7}$alkyl, bis-oxy-alkylene and N—C$_{1-4}$ alkyl piperazinyl;
    (ii) —CN;
    (iii) —C(=O)—NR$^{N1}$R$^{N2}$, where R$^{N1}$ and R$^{N2}$ are C$_{1-7}$ alkyl groups;
    (iv) —C(=O)—OR$^O$, where R$^O$ is a C$_{1-7}$ alkyl group;
    (v) —OR$^O$;

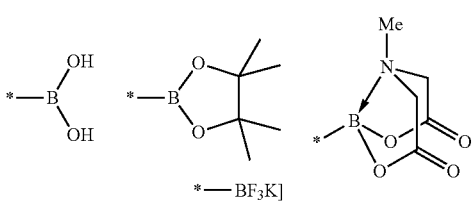

(vi) —Sn($R^{SN}$)$_3$ where $R^{SN}$ is a $C_{1-7}$ alkyl group; and $R^{10}$ is a carbamate-based nitrogen protecting group, which is palladium-labile and/or labile under the conditions used to add the group:

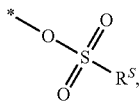

or contains a moiety which is palladium-labile and/or is labile under the conditions used to add the group:

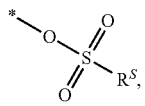

which is substantially free of any of the corresponding compound of formula VIB:

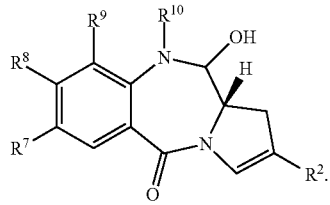

VIB

23. A method of synthesising a compound of formula VI:

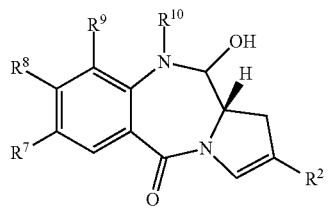

VI wherein $R^7$ and $R^8$ are independently selected from: $OR^A$, where $R^A$ is selected from $C_{1-4}$ saturated alkyl, optionally substituted by phenyl, which may bear a chloro substituent, pyridyl and furanyl; chloro; $NH_2$; —$CH_2$—O—C(=O)Me; or $R^7$ and $R_8$ together form a group —O—($CH_2$)$_m$—O—, where m is 1 or 2; or the compound is a dimer with each monomer independently being of formula (VI), where the $R^7$ groups or $R^8$ groups of each monomer form together a dimer bridge having the formula —X—R"—X— linking the monomers where R" is a $C_{3-12}$ saturated alkylene group, which group may be interrupted by O, S, NH, NMe, phenylene or pyridylene, where the phenylene and pyridylene groups are optionally substituted by $NH_2$, and each X is independently selected from O, S, or NH;

$R^9$ is selected from H, methyl and methoxy;

$R^2$ is selected from:

(i) an optionally substituted $C_{5-20}$ aryl group wherein the optional substituents are chosen from halo, $C_{1-7}$ alkoxy, di-$C_{1-4}$alkylamino-$C_{1-7}$alkoxy, $C_{1-7}$alkyl, bis-oxy-alkylene and N—$C_{1-4}$ alkyl piperazinyl; and (ii) an optionally substituted $C_{2-5}$ alkenyl group or $C_{2-5}$ alkynyl group, wherein the optional substituents are chosen from:

(i) optionally substituted $C_{5-20}$ aryl groups wherein the optional substituents are chosen from halo, $C_{1-7}$ alkoxy, di-$C_{1-4}$ alkylamino-$C_{1-7}$alkoxy, $C_{1-7}$alkyl, bis-oxy-alkylene and N—$C_{1-4}$ alkyl piperazinyl;

(ii) —CN;

(iii) —C(=O)—$NR^{N1}R^{N2}$, where $R^{N1}$ and $R^{N2}$ are $C_{1-7}$ alkyl groups;

(iv) —C(=O)—$OR^O$, where $R^O$ is a $C_{1-7}$ alkyl group;

(v) —$OR^O$;

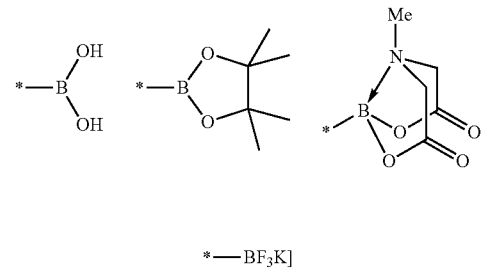

(vi) —Sn($R^{SN}$)$_3$ where $R^{SN}$ is a $C_{1-7}$ alkyl group; and $R^{10}$ is a carbamate-based nitrogen protecting group, which is palladium-labile and/or labile under the conditions used to add the group:

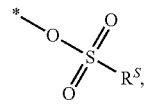

or contains a moiety which is palladium-labile and/or is labile under the conditions used to add the group:

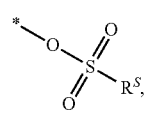

from a compound of formula V:

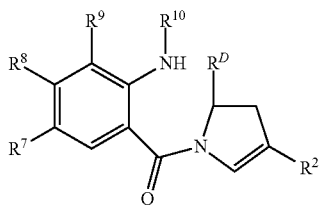

V wherein $R^D$ is selected from:
- (ii) —$CH_2$—O—C(=O)$R^{C2}$, where $R^{C2}$ is methyl or phenyl;
- (iii) —$CH_2$—O—Si—($R^{Si1}$)($R^{Si2}$)($R^{Si3}$), where $R^{Si1}$, $R^{Si2}$, $R^{Si3}$ are independently selected from $C_{1-6}$ saturated alkyl group and a phenyl group; and
- (iv) —C(—$YR^{C3}$)(—$YR^{C4}$) where each Y is independently O or S, and where $R^{C3}$ and $R^{C4}$ are independently a saturated $C_{1-4}$ alkyl group, or together form a $C_{2-3}$ alkylene by one of the following:

(a) (i) where $R^D$ is —$CH_2$—O—C(=O)Me, removal of the acetate protecting group, with potassium carbonate in aqueous methanol, or with lithium triethylborohydride;
(ii) where $R^D$ is —$CH_2$—O—Si—($R^{Si1}$)($R^{Si2}$)($R^{Si3}$), removal of the silyl ether protecting group using: TBAF in THF; acetic acid in aqueous THF; CsF in DMF; or HF in pyridine; and
(b) oxidation of the product of step (a); or
(c) where $R^D$ is —C(—$YR^{C3}$)(—$YR^{C4}$), removal of the acetal or thioacetal protecting groups, respectively with acid or reaction with Hg (II) salts, wherein the compound of formula V is synthesised from a compound of formula II:

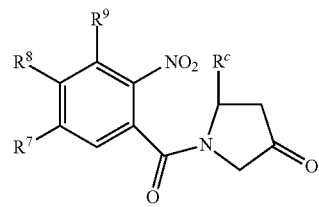

II including the method comprising treating II with the appropriate anhydride and anhydrous 2,6-lutidine or anhydrous 2,6-tBu-pyridine at a temperature of −35° C. or lower in a dry organic solvent under a inert atmosphere.

24. A method according to claim 23, wherein the oxidation is carried out with Dess-Martin periodinane.

* * * * *